(12) United States Patent
Vidlund et al.

(10) Patent No.: US 11,253,359 B2
(45) Date of Patent: Feb. 22, 2022

(54) PROXIMAL TAB FOR SIDE-DELIVERED TRANSCATHETER HEART VALVES AND METHODS OF DELIVERY

(71) Applicant: VDyne, Inc., Maple Grove, MN (US)

(72) Inventors: Robert Vidlund, Forest Lake, MN (US); Mark Christianson, Plymouth, MN (US); Neelakantan Saikrishnan, Plymouth, MN (US); Scott Kramer, Minneapolis, MN (US)

(73) Assignee: VDyne, Inc., Maple Grove, MN (US)

( * ) Notice: Subject to any disclaimer, the term of this patent is extended or adjusted under 35 U.S.C. 154(b) by 0 days.

(21) Appl. No.: 17/221,547

(22) Filed: Apr. 2, 2021

(65) Prior Publication Data

US 2021/0220127 A1    Jul. 22, 2021

Related U.S. Application Data

(63) Continuation-in-part of application No. 16/877,457, filed on May 18, 2020, and a continuation of
(Continued)

(51) Int. Cl.
*A61F 2/24*    (2006.01)

(52) U.S. Cl.
CPC .......... *A61F 2/2418* (2013.01); *A61F 2/2433* (2013.01); *A61F 2/2436* (2013.01);
(Continued)

(58) Field of Classification Search
CPC .................. A61F 2/2409; A61F 2/2418; A61F 2250/0008–0016
See application file for complete search history.

(56) References Cited

U.S. PATENT DOCUMENTS

| 3,744,060 A | 7/1973 | Bellhouse et al. |
| 4,079,468 A | 3/1978 | Liotta et al. |

(Continued)

FOREIGN PATENT DOCUMENTS

| AU | 2006203686 B2 | 11/2008 |
| AU | 2009219415 A1 | 9/2009 |

(Continued)

OTHER PUBLICATIONS

Office Action for U.S. Appl. No. 16/435,687, dated Aug. 7, 2019, 19 pages.

(Continued)

*Primary Examiner* — Rebecca S Preston

(57) ABSTRACT

A prosthetic heart valve includes a valve frame defining an aperture that extends along a central axis and a flow control component mounted within the aperture. The valve frame includes a distal anchoring element and a proximal anchoring element. The valve frame has a compressed configuration to allow the prosthetic heart valve to be delivered to a heart of a patient via a delivery catheter. The valve frame is configured to transition to an expanded configuration when released from the delivery catheter. The prosthetic heart valve is configured to be seated in a native annulus when the valve frame is in the expanded configuration. The distal and proximal anchoring elements configured to be inserted through the native annulus prior to seating the prosthetic heart valve. The proximal anchoring element is ready to be deployed subannularly or is optionally configured to be transitioned from a first configuration to a second configuration after the prosthetic valve is seated.

22 Claims, 28 Drawing Sheets

Related U.S. Application Data application No. PCT/US2019/067010, filed on Dec. 18, 2019, said application No. 16/877,457 is a continuation of application No. 16/455,417, filed on Jun. 27, 2019, now Pat. No. 10,653,522, said application No. PCT/US2019/067010 is a continuation-in-part of application No. 16/455,417, filed on Jun. 27, 2019, now Pat. No. 10,653,522.

(60) Provisional application No. 62/782,350, filed on Dec. 20, 2018.

(52) U.S. Cl.
CPC .......... *A61F 2/2439* (2013.01); *A61F 2/2412* (2013.01); *A61F 2/2442* (2013.01); *A61F 2210/0014* (2013.01); *A61F 2220/0008* (2013.01); *A61F 2220/0016* (2013.01); *A61F 2220/0025* (2013.01); *A61F 2250/0008* (2013.01); *A61F 2250/0039* (2013.01); *A61F 2250/0069* (2013.01)

(56) References Cited

U.S. PATENT DOCUMENTS

| | | |
|---|---|---|
| 5,397,351 A | 3/1995 | Pavcnik et al. |
| 5,509,428 A | 4/1996 | Dunlop |
| 5,554,185 A | 9/1996 | Block et al. |
| 6,006,134 A | 12/1999 | Hill et al. |
| 6,197,013 B1 | 3/2001 | Reed et al. |
| 6,290,719 B1 | 9/2001 | Garberoglio |
| 6,449,507 B1 | 9/2002 | Hill et al. |
| 6,458,153 B1 | 10/2002 | Bailey et al. |
| 6,532,388 B1 | 3/2003 | Hill et al. |
| 6,582,467 B1 | 6/2003 | Teitelbaum et al. |
| 6,628,987 B1 | 9/2003 | Hill et al. |
| 6,669,724 B2 | 12/2003 | Park et al. |
| 6,718,208 B2 | 4/2004 | Hill et al. |
| 6,769,434 B2 | 8/2004 | Liddicoat et al. |
| 6,890,330 B2 | 5/2005 | Streeter et al. |
| 6,896,690 B1 | 5/2005 | Lambrecht et al. |
| 6,904,318 B2 | 6/2005 | Hill et al. |
| 6,929,653 B2 | 8/2005 | Strecter |
| 7,074,189 B1 | 7/2006 | Montegrande |
| 7,125,418 B2 | 10/2006 | Duran et al. |
| 7,175,660 B2 | 2/2007 | Cartledge et al. |
| 7,201,761 B2 | 4/2007 | Woolfson et al. |
| 7,225,019 B2 | 5/2007 | Jahns et al. |
| 7,269,457 B2 | 9/2007 | Shafer et al. |
| 7,331,991 B2 | 2/2008 | Kheradvar et al. |
| 7,361,189 B2 | 4/2008 | Case et al. |
| 7,374,571 B2 | 5/2008 | Pease et al. |
| 7,442,204 B2 | 10/2008 | Schwammenthal et al. |
| 7,449,027 B2 | 11/2008 | Hunt et al. |
| 7,621,948 B2 | 11/2009 | Herrmann et al. |
| 7,648,527 B2 | 1/2010 | Agnew |
| 7,717,952 B2 | 5/2010 | Case et al. |
| 7,749,245 B2 | 7/2010 | Cohn et al. |
| 7,753,949 B2 | 7/2010 | Lamphere et al. |
| 7,811,316 B2 | 10/2010 | Kalmann et al. |
| 7,828,840 B2 | 11/2010 | Biggs et al. |
| 7,846,199 B2 | 12/2010 | Paul, Jr. et al. |
| 8,303,648 B2 | 11/2012 | Grewe et al. |
| 8,366,768 B2 | 2/2013 | Zhang |
| 8,491,650 B2 | 7/2013 | Wiemeyer et al. |
| 8,568,474 B2 | 10/2013 | Yeung et al. |
| 8,628,571 B1 | 1/2014 | Hacohen et al. |
| 8,641,752 B1 | 2/2014 | Holm et al. |
| 8,696,743 B2 | 4/2014 | Holecek et al. |
| 8,728,153 B2 | 5/2014 | Bishop et al. |
| 8,758,395 B2 | 6/2014 | Kleshinski et al. |
| 8,846,390 B2 | 9/2014 | Dove et al. |
| 8,876,892 B2 | 11/2014 | Tran et al. |
| 8,900,295 B2 | 12/2014 | Migliazza et al. |
| 8,915,958 B2 | 12/2014 | Braido |
| 8,926,690 B2 | 1/2015 | Kovalsky |
| 8,926,692 B2 | 1/2015 | Dwork |
| 8,926,694 B2 | 1/2015 | Costello |
| 8,940,044 B2 | 1/2015 | Hammer et al. |
| 8,956,404 B2 | 2/2015 | Bortlein et al. |
| 8,986,370 B2 | 3/2015 | Annest et al. |
| 9,011,524 B2 | 4/2015 | Eberhardt |
| 9,017,399 B2 | 4/2015 | Gross et al. |
| 9,050,188 B2 | 6/2015 | Schweich, Jr. et al. |
| 9,072,604 B1 | 7/2015 | Melnick et al. |
| 9,119,714 B2 | 9/2015 | Shandas et al. |
| 9,216,076 B2 | 12/2015 | Mitra et al. |
| 9,232,995 B2 | 1/2016 | Kovalsky et al. |
| 9,241,792 B2 | 1/2016 | Benichou et al. |
| 9,248,016 B2 | 2/2016 | Oba et al. |
| 9,259,215 B2 | 2/2016 | Chou et al. |
| 9,277,990 B2 | 3/2016 | Klima et al. |
| 9,289,282 B2 | 3/2016 | Olson et al. |
| 9,289,296 B2 | 3/2016 | Braido et al. |
| 9,295,547 B2 | 3/2016 | Costello et al. |
| 9,301,839 B2 | 4/2016 | Stante et al. |
| 9,308,086 B2 | 4/2016 | Ho |
| 9,339,367 B2 | 5/2016 | Carpenter et al. |
| 9,370,418 B2 | 6/2016 | Pintor et al. |
| 9,381,083 B2 | 7/2016 | Costello |
| 9,387,075 B2 | 7/2016 | Bortlein et al. |
| 9,393,111 B2 | 7/2016 | Ma et al. |
| 9,414,915 B2 | 8/2016 | Lombardi et al. |
| 9,433,500 B2 | 9/2016 | Chau et al. |
| 9,440,054 B2 | 9/2016 | Bishop et al. |
| 9,456,899 B2 | 10/2016 | Yeung et al. |
| 9,468,525 B2 | 10/2016 | Kovalsky et al. |
| 9,474,604 B2 | 10/2016 | Centola et al. |
| 9,486,306 B2 | 11/2016 | Tegels et al. |
| 9,510,941 B2 | 12/2016 | Bishop et al. |
| 9,554,902 B2 | 1/2017 | Braido et al. |
| 9,579,196 B2 | 2/2017 | Morriss et al. |
| 9,579,200 B2 | 2/2017 | Lederman et al. |
| 9,610,159 B2 | 4/2017 | Christianson et al. |
| 9,615,925 B2 | 4/2017 | Subramanian et al. |
| 9,629,719 B2 | 4/2017 | Rothstein |
| 9,636,222 B2 | 5/2017 | Oslund |
| 9,649,191 B2 | 5/2017 | Savage et al. |
| 9,662,202 B2 | 5/2017 | Quill et al. |
| 9,662,203 B2 | 5/2017 | Sheahan et al. |
| 9,662,209 B2 | 5/2017 | Gross et al. |
| 9,675,454 B2 | 6/2017 | Vidlund et al. |
| 9,675,485 B2 | 6/2017 | Essinger et al. |
| 9,687,343 B2 | 6/2017 | Bortlein et al. |
| 9,707,076 B2 | 7/2017 | Stack et al. |
| 9,713,530 B2 | 7/2017 | Cabiri et al. |
| 9,750,607 B2 | 9/2017 | Ganesan et al. |
| 9,763,778 B2 | 9/2017 | Eidenschink et al. |
| 9,763,779 B2 | 9/2017 | Bortlein et al. |
| 9,788,946 B2 | 10/2017 | Bobo, Jr. et al. |
| 9,839,511 B2 | 12/2017 | Ma et al. |
| 9,849,011 B2 | 12/2017 | Zimmerman et al. |
| 9,855,384 B2 | 1/2018 | Cohen et al. |
| 9,861,464 B2 | 1/2018 | Azimpour et al. |
| 9,895,219 B2 | 2/2018 | Costello et al. |
| 9,901,330 B2 | 2/2018 | Akpinar |
| 9,918,838 B2 | 3/2018 | Ring |
| 9,943,409 B2 | 4/2018 | Kim et al. |
| 9,949,825 B2 | 4/2018 | Braido et al. |
| 9,968,444 B2 | 5/2018 | Millwee et al. |
| 9,968,445 B2 | 5/2018 | Kheradvar |
| 9,980,815 B2 | 5/2018 | Nitzan et al. |
| 9,987,121 B2 | 6/2018 | Blanzy |
| 10,010,411 B2 | 7/2018 | Peter |
| 10,010,412 B2 | 7/2018 | Taft et al. |
| 10,022,054 B2 | 7/2018 | Najafi et al. |
| 10,022,222 B2 | 7/2018 | Groothuis et al. |
| 10,022,223 B2 | 7/2018 | Bruchman |
| 10,028,821 B2 | 7/2018 | Centola et al. |
| 10,028,831 B2 | 7/2018 | Morin et al. |
| 10,034,667 B2 | 7/2018 | Morris et al. |
| 10,034,747 B2 | 7/2018 | Harewood |
| 10,039,638 B2 | 8/2018 | Bruchman et al. |

(56) References Cited

U.S. PATENT DOCUMENTS

| | | |
|---|---|---|
| 10,058,315 B2 | 8/2018 | Rafiee et al. |
| 10,058,411 B2 | 8/2018 | Fifer et al. |
| 10,058,421 B2 | 8/2018 | Eberhardt et al. |
| 10,058,426 B2 | 8/2018 | Barbarino |
| 10,064,405 B2 | 9/2018 | Dale et al. |
| 10,080,653 B2 | 9/2018 | Conklin et al. |
| 10,085,835 B2 | 10/2018 | Thambar et al. |
| 10,105,224 B2 | 10/2018 | Buchbinder et al. |
| 10,117,741 B2 | 11/2018 | Schweich, Jr. et al. |
| 10,123,874 B2 | 11/2018 | Khairkhahan et al. |
| 10,130,331 B2 | 11/2018 | Stigall et al. |
| 10,130,467 B2 | 11/2018 | Braido et al. |
| 10,149,685 B2 | 12/2018 | Kizuka |
| 10,154,905 B2 | 12/2018 | Duffy |
| 10,179,043 B2 | 1/2019 | Cohen-Tzemach et al. |
| 10,182,908 B2 | 1/2019 | Tubishevitz et al. |
| 10,182,911 B2 | 1/2019 | Hillukka |
| 10,206,775 B2 | 2/2019 | Kovalsky et al. |
| 10,219,895 B2 | 3/2019 | Wagner et al. |
| 10,219,896 B2 | 3/2019 | Sandstrom et al. |
| 10,220,192 B2 | 3/2019 | Drasler et al. |
| 10,226,178 B2 | 3/2019 | Cohen et al. |
| 10,226,335 B2 | 3/2019 | Cartledge et al. |
| 10,245,142 B2 | 4/2019 | Bonhoeffer |
| 10,258,467 B2 | 4/2019 | Hou et al. |
| 10,265,173 B2 | 4/2019 | Griffin et al. |
| 10,321,987 B2 | 6/2019 | Wang et al. |
| 10,321,995 B1 | 6/2019 | Christianson et al. |
| 10,327,895 B2 | 6/2019 | Lozonschi et al. |
| 10,327,899 B2 | 6/2019 | Sandstrom et al. |
| 10,329,066 B2 | 6/2019 | Kruetzfeldt et al. |
| 10,350,047 B2 | 7/2019 | Rajpara et al. |
| 10,357,361 B2 | 7/2019 | Rafi et al. |
| 10,368,989 B2 | 8/2019 | Duffy et al. |
| 10,398,550 B2 | 9/2019 | Chalekian et al. |
| 10,426,611 B2 | 10/2019 | Hariton et al. |
| 10,433,957 B2 | 10/2019 | Khouengboua et al. |
| 10,433,960 B1 | 10/2019 | Sutherland et al. |
| 10,463,489 B2 | 11/2019 | Christianson et al. |
| 10,485,976 B2 | 11/2019 | Streeter et al. |
| 10,595,994 B1 | 3/2020 | Christianson et al. |
| 10,631,983 B1 | 4/2020 | Christianson et al. |
| 10,653,522 B1 | 5/2020 | Vidlund et al. |
| 10,758,346 B1 | 9/2020 | Christianson et al. |
| 11,071,627 B2 | 7/2021 | Saikrishnan et al. |
| 11,076,956 B2 | 8/2021 | Christianson et al. |
| 11,109,969 B2 | 9/2021 | Vidlund et al. |
| 11,166,814 B2 | 11/2021 | Vidlund et al. |
| 11,173,027 B2 | 11/2021 | Christianson et al. |
| 2003/0040772 A1 | 2/2003 | Hyodoh et al. |
| 2003/0040808 A1 | 2/2003 | Stack et al. |
| 2003/0153901 A1 | 8/2003 | Herweck et al. |
| 2003/0166990 A1 | 9/2003 | Trauthen et al. |
| 2003/0171801 A1 | 9/2003 | Bates |
| 2004/0049207 A1 | 3/2004 | Goldfarb et al. |
| 2004/0088047 A1 | 5/2004 | Spence et al. |
| 2004/0093060 A1 | 5/2004 | Seguin et al. |
| 2004/0116996 A1 | 6/2004 | Freitag |
| 2004/0199209 A1 | 10/2004 | Hill et al. |
| 2004/0225352 A1 | 11/2004 | Osborne et al. |
| 2005/0010246 A1 | 1/2005 | Streeter et al. |
| 2005/0075659 A1 | 4/2005 | Realyvasquez et al. |
| 2005/0075725 A1 | 4/2005 | Rowe |
| 2005/0107811 A1 | 5/2005 | Starksen et al. |
| 2005/0137686 A1 | 6/2005 | Salahieh et al. |
| 2005/0228495 A1 | 10/2005 | Macoviak |
| 2006/0015167 A1 | 1/2006 | Armstrong et al. |
| 2006/0190075 A1 | 8/2006 | Jordan et al. |
| 2006/0195180 A1 | 8/2006 | Kheradvar et al. |
| 2006/0229708 A1 | 10/2006 | Powell et al. |
| 2006/0241745 A1 | 10/2006 | Solem |
| 2006/0271098 A1 | 11/2006 | Peacock, III |
| 2006/0276887 A1 | 12/2006 | Brady et al. |
| 2007/0016286 A1 | 1/2007 | Herrmann et al. |
| 2007/0027535 A1 | 2/2007 | Purdy, Jr. et al. |
| 2007/0032850 A1 | 2/2007 | Ruiz et al. |
| 2007/0038295 A1 | 2/2007 | Case et al. |
| 2007/0100427 A1 | 5/2007 | Perouse |
| 2007/0162102 A1 | 7/2007 | Ryan et al. |
| 2007/0208417 A1 | 9/2007 | Agnew |
| 2007/0213805 A1 | 9/2007 | Schaeffer et al. |
| 2007/0233176 A1 | 10/2007 | Gilson et al. |
| 2007/0233228 A1 | 10/2007 | Eberhardt et al. |
| 2007/0239271 A1 | 10/2007 | Nguyen |
| 2007/0288087 A1 | 12/2007 | Fearnot et al. |
| 2008/0004686 A1 | 1/2008 | Hunt et al. |
| 2008/0020013 A1 | 1/2008 | Reyes et al. |
| 2008/0065204 A1 | 3/2008 | Macoviak et al. |
| 2008/0071287 A1 | 3/2008 | Goto |
| 2008/0132999 A1 | 6/2008 | Mericle et al. |
| 2008/0140181 A1 | 6/2008 | Reynolds et al. |
| 2008/0154355 A1 | 6/2008 | Benichou et al. |
| 2008/0183279 A1 | 7/2008 | Bailey et al. |
| 2008/0200977 A1 | 8/2008 | Paul et al. |
| 2008/0200980 A1 | 8/2008 | Robin et al. |
| 2008/0208332 A1 | 8/2008 | Lamphere et al. |
| 2008/0221672 A1 | 9/2008 | Lamphere et al. |
| 2008/0262592 A1 | 10/2008 | Jordan et al. |
| 2008/0262609 A1 | 10/2008 | Gross et al. |
| 2008/0275550 A1 | 11/2008 | Kheradvar et al. |
| 2009/0005863 A1 | 1/2009 | Goetz et al. |
| 2009/0054976 A1 | 2/2009 | Tuval et al. |
| 2009/0094189 A1 | 4/2009 | Stephens |
| 2009/0192586 A1 | 7/2009 | Tabor et al. |
| 2009/0254174 A1 | 10/2009 | Case et al. |
| 2009/0264991 A1 | 10/2009 | Paul, Jr. et al. |
| 2009/0287290 A1 | 11/2009 | Macaulay et al. |
| 2010/0049294 A1 | 2/2010 | Zukowski et al. |
| 2010/0049313 A1 | 2/2010 | Alon et al. |
| 2010/0121434 A1 | 5/2010 | Paul et al. |
| 2010/0160773 A1 | 6/2010 | Cohen et al. |
| 2010/0161043 A1 | 6/2010 | Maisano et al. |
| 2010/0168844 A1 | 7/2010 | Toomes et al. |
| 2010/0174363 A1 | 7/2010 | Castro |
| 2010/0179583 A1 | 7/2010 | Carpenter et al. |
| 2010/0179584 A1 | 7/2010 | Carpenter et al. |
| 2010/0179647 A1 | 7/2010 | Carpenter et al. |
| 2010/0280591 A1 | 11/2010 | Shin et al. |
| 2010/0298929 A1 | 11/2010 | Thornton et al. |
| 2010/0305685 A1 | 12/2010 | Millwee et al. |
| 2011/0004237 A1 | 1/2011 | Schneider et al. |
| 2011/0029071 A1 | 2/2011 | Zlotnick et al. |
| 2011/0029072 A1 | 2/2011 | Gabbay |
| 2011/0066233 A1 | 3/2011 | Thornton et al. |
| 2011/0071613 A1 | 3/2011 | Wood et al. |
| 2011/0098804 A1 | 4/2011 | Yeung et al. |
| 2011/0125145 A1 | 5/2011 | Mody et al. |
| 2011/0137397 A1 | 6/2011 | Chau et al. |
| 2011/0160836 A1 | 6/2011 | Behan |
| 2011/0172764 A1 | 7/2011 | Badhwar |
| 2011/0224785 A1 | 9/2011 | Hacohen et al. |
| 2011/0245911 A1 | 10/2011 | Quill et al. |
| 2011/0245917 A1 | 10/2011 | Savage et al. |
| 2011/0251675 A1 | 10/2011 | Dwork |
| 2011/0257721 A1 | 10/2011 | Tabor |
| 2011/0264191 A1 | 10/2011 | Rothstein |
| 2012/0022605 A1 | 1/2012 | Jahns et al. |
| 2012/0022633 A1 | 1/2012 | Olson et al. |
| 2012/0022639 A1 | 1/2012 | Hacohen et al. |
| 2012/0022640 A1 | 1/2012 | Gross et al. |
| 2012/0022644 A1 | 1/2012 | Reich et al. |
| 2012/0035701 A1 | 2/2012 | To |
| 2012/0065723 A1 | 3/2012 | Drasler et al. |
| 2012/0083874 A1 | 4/2012 | Dale et al. |
| 2012/0123531 A1 | 5/2012 | Tsukashima et al. |
| 2012/0137521 A1 | 6/2012 | Millwee et al. |
| 2012/0165928 A1 | 6/2012 | Nitzan et al. |
| 2012/0172981 A1 | 7/2012 | DuMontelle |
| 2012/0203336 A1 | 8/2012 | Annest |
| 2012/0209375 A1 | 8/2012 | Madrid et al. |
| 2012/0232574 A1 | 9/2012 | Kim et al. |
| 2012/0277853 A1 | 11/2012 | Rothstein |
| 2012/0310327 A1 | 12/2012 | McHugo |
| 2012/0310328 A1 | 12/2012 | Olson et al. |

(56) References Cited

U.S. PATENT DOCUMENTS

| | | |
|---|---|---|
| 2013/0035759 A1 | 2/2013 | Gross et al. |
| 2013/0055941 A1 | 3/2013 | Holecek et al. |
| 2013/0131714 A1 | 5/2013 | Wang et al. |
| 2013/0131792 A1 | 5/2013 | Miller et al. |
| 2013/0166017 A1 | 6/2013 | Cartledge et al. |
| 2013/0184742 A1 | 7/2013 | Ganesan et al. |
| 2013/0190857 A1 | 7/2013 | Mitra et al. |
| 2013/0190861 A1 | 7/2013 | Chau et al. |
| 2013/0197621 A1 | 8/2013 | Ryan et al. |
| 2013/0226289 A1 | 8/2013 | Shaolian et al. |
| 2013/0238010 A1 | 9/2013 | Johnson et al. |
| 2013/0238089 A1 | 9/2013 | Lichtenstein et al. |
| 2013/0253570 A1 | 9/2013 | Bates |
| 2013/0274618 A1 | 10/2013 | Hou et al. |
| 2013/0274855 A1 | 10/2013 | Stante et al. |
| 2013/0282110 A1 | 10/2013 | Schweich, Jr. et al. |
| 2013/0297010 A1 | 11/2013 | Bishop et al. |
| 2013/0304197 A1 | 11/2013 | Buchbinder et al. |
| 2013/0304200 A1 | 11/2013 | McLean et al. |
| 2013/0331929 A1 | 12/2013 | Mitra et al. |
| 2013/0338764 A1 | 12/2013 | Thornton et al. |
| 2014/0000112 A1 | 1/2014 | Braido et al. |
| 2014/0005540 A1 | 1/2014 | Merhi |
| 2014/0005768 A1 | 1/2014 | Thomas et al. |
| 2014/0005778 A1 | 1/2014 | Buchbinder et al. |
| 2014/0012372 A1 | 1/2014 | Chau et al. |
| 2014/0018915 A1 | 1/2014 | Baidillah et al. |
| 2014/0039511 A1 | 2/2014 | Morris et al. |
| 2014/0039611 A1 | 2/2014 | Lane et al. |
| 2014/0052237 A1 | 2/2014 | Lane et al. |
| 2014/0081383 A1 | 3/2014 | Eberhardt et al. |
| 2014/0088680 A1 | 3/2014 | Costello et al. |
| 2014/0107758 A1 | 4/2014 | Glazier |
| 2014/0110279 A1 | 4/2014 | Kruetzfeldt et al. |
| 2014/0114403 A1 | 4/2014 | Dale et al. |
| 2014/0121763 A1 | 5/2014 | Duffy et al. |
| 2014/0135895 A1 | 5/2014 | Andress et al. |
| 2014/0135908 A1 | 5/2014 | Glozman et al. |
| 2014/0142695 A1 | 5/2014 | Gross et al. |
| 2014/0172070 A1 | 6/2014 | Seguin |
| 2014/0180069 A1 | 6/2014 | Millett |
| 2014/0180070 A1 | 6/2014 | Millett et al. |
| 2014/0194704 A1 | 7/2014 | Millett et al. |
| 2014/0194983 A1 | 7/2014 | Kovalsky et al. |
| 2014/0207231 A1 | 7/2014 | Hacohen et al. |
| 2014/0214069 A1 | 7/2014 | Franklin |
| 2014/0214159 A1 | 7/2014 | Vidlund et al. |
| 2014/0222136 A1 | 8/2014 | Geist et al. |
| 2014/0222137 A1 | 8/2014 | Miller et al. |
| 2014/0222142 A1* | 8/2014 | Kovalsky ............ A61F 2/2418 623/2.17 |
| 2014/0249566 A1 | 9/2014 | Quinn et al. |
| 2014/0257466 A1 | 9/2014 | Board et al. |
| 2014/0257467 A1 | 9/2014 | Lane et al. |
| 2014/0276616 A1 | 9/2014 | Smith et al. |
| 2014/0276971 A1 | 9/2014 | Kovach |
| 2014/0277342 A1 | 9/2014 | Roeder et al. |
| 2014/0277388 A1 | 9/2014 | Skemp |
| 2014/0277408 A1 | 9/2014 | Folan |
| 2014/0296962 A1 | 10/2014 | Cartledge et al. |
| 2014/0296969 A1 | 10/2014 | Tegels et al. |
| 2014/0303718 A1 | 10/2014 | Tegels et al. |
| 2014/0303724 A1 | 10/2014 | Bluestein et al. |
| 2014/0309732 A1 | 10/2014 | Solem |
| 2014/0324161 A1 | 10/2014 | Tegels et al. |
| 2014/0350662 A1 | 11/2014 | Vaturi |
| 2014/0358224 A1 | 12/2014 | Tegels et al. |
| 2014/0371789 A1 | 12/2014 | Hariton et al. |
| 2014/0379076 A1 | 12/2014 | Vidlund et al. |
| 2015/0005808 A1 | 1/2015 | Chouinard et al. |
| 2015/0005874 A1 | 1/2015 | Vidlund et al. |
| 2015/0039081 A1 | 2/2015 | Costello |
| 2015/0045880 A1 | 2/2015 | Hacohen |
| 2015/0051687 A1 | 2/2015 | Dickerhoff et al. |
| 2015/0094802 A1 | 4/2015 | Buchbinder et al. |
| 2015/0112188 A1 | 4/2015 | Stigall et al. |
| 2015/0119982 A1 | 4/2015 | Quill et al. |
| 2015/0127093 A1 | 5/2015 | Hosmer et al. |
| 2015/0142103 A1 | 5/2015 | Vidlund |
| 2015/0157457 A1 | 6/2015 | Hacohen |
| 2015/0173898 A1 | 6/2015 | Drasler et al. |
| 2015/0196390 A1 | 7/2015 | Ma et al. |
| 2015/0196391 A1 | 7/2015 | Dwork |
| 2015/0202044 A1 | 7/2015 | Chau et al. |
| 2015/0216661 A1 | 8/2015 | Hacohen et al. |
| 2015/0230919 A1 | 8/2015 | Chau et al. |
| 2015/0245934 A1 | 9/2015 | Lombardi et al. |
| 2015/0257878 A1 | 9/2015 | Lane et al. |
| 2015/0257880 A1 | 9/2015 | Bortlein et al. |
| 2015/0257882 A1 | 9/2015 | Bortlein et al. |
| 2015/0265400 A1 | 9/2015 | Eidenschink et al. |
| 2015/0272731 A1 | 10/2015 | Racchini et al. |
| 2015/0282922 A1 | 10/2015 | Hingston et al. |
| 2015/0282931 A1 | 10/2015 | Brunnett et al. |
| 2015/0289971 A1 | 10/2015 | Costello et al. |
| 2015/0289975 A1 | 10/2015 | Costello |
| 2015/0297241 A1 | 10/2015 | Yodfat et al. |
| 2015/0305867 A1 | 10/2015 | Liu et al. |
| 2015/0313701 A1 | 11/2015 | Krahbichler |
| 2015/0335424 A1 | 11/2015 | McLean et al. |
| 2015/0342717 A1 | 12/2015 | O'Donnell et al. |
| 2015/0351904 A1 | 12/2015 | Cooper et al. |
| 2015/0351906 A1 | 12/2015 | Hammer et al. |
| 2015/0351910 A1 | 12/2015 | Gilmore et al. |
| 2015/0359629 A1 | 12/2015 | Ganesan et al. |
| 2016/0008130 A1 | 1/2016 | Hasin |
| 2016/0008131 A1 | 1/2016 | Christianson et al. |
| 2016/0022417 A1 | 1/2016 | Karapetian et al. |
| 2016/0030165 A1 | 2/2016 | Mitra et al. |
| 2016/0030167 A1 | 2/2016 | Delaloye et al. |
| 2016/0038280 A1 | 2/2016 | Morriss et al. |
| 2016/0038283 A1 | 2/2016 | Divekar et al. |
| 2016/0045165 A1 | 2/2016 | Braido et al. |
| 2016/0045306 A1 | 2/2016 | Agrawal et al. |
| 2016/0045309 A1 | 2/2016 | Valdez et al. |
| 2016/0067031 A1 | 3/2016 | Kassab et al. |
| 2016/0081799 A1 | 3/2016 | Leo et al. |
| 2016/0095703 A1 | 4/2016 | Thomas et al. |
| 2016/0095704 A1 | 4/2016 | Whitman |
| 2016/0113764 A1 | 4/2016 | Sheahan et al. |
| 2016/0113766 A1 | 4/2016 | Ganesan et al. |
| 2016/0113768 A1 | 4/2016 | Ganesan et al. |
| 2016/0143721 A1 | 5/2016 | Rosenbluth et al. |
| 2016/0143730 A1 | 5/2016 | Kheradvar |
| 2016/0143735 A1 | 5/2016 | Subramanian et al. |
| 2016/0143739 A1 | 5/2016 | Horgan et al. |
| 2016/0158004 A1 | 6/2016 | Kumar et al. |
| 2016/0158007 A1 | 6/2016 | Centola et al. |
| 2016/0158008 A1 | 6/2016 | Miller et al. |
| 2016/0166382 A1 | 6/2016 | Nguyen |
| 2016/0184488 A1 | 6/2016 | Toyoda et al. |
| 2016/0194425 A1 | 7/2016 | Mitra et al. |
| 2016/0213470 A1 | 7/2016 | Ahlberg et al. |
| 2016/0213473 A1 | 7/2016 | Hacohen et al. |
| 2016/0220367 A1 | 8/2016 | Barrett |
| 2016/0220372 A1 | 8/2016 | Medema et al. |
| 2016/0220734 A1 | 8/2016 | Dyamenahalli et al. |
| 2016/0228250 A1 | 8/2016 | Casley et al. |
| 2016/0235530 A1 | 8/2016 | Thomas et al. |
| 2016/0256269 A1 | 9/2016 | Cahalane et al. |
| 2016/0256270 A1 | 9/2016 | Folan et al. |
| 2016/0270911 A1 | 9/2016 | Ganesan et al. |
| 2016/0303804 A1 | 10/2016 | Grbic et al. |
| 2016/0310274 A1 | 10/2016 | Gross et al. |
| 2016/0317301 A1 | 11/2016 | Quadri et al. |
| 2016/0324633 A1 | 11/2016 | Gross et al. |
| 2016/0324639 A1 | 11/2016 | Nguyen et al. |
| 2016/0331534 A1 | 11/2016 | Buchbinder et al. |
| 2016/0354201 A1 | 12/2016 | Keogh |
| 2016/0361169 A1 | 12/2016 | Gross et al. |
| 2016/0361184 A1 | 12/2016 | Tabor et al. |
| 2016/0367360 A1 | 12/2016 | Cartledge et al. |
| 2016/0367364 A1 | 12/2016 | Torrianni et al. |
| 2017/0000603 A1 | 1/2017 | Conklin et al. |

(56) References Cited

U.S. PATENT DOCUMENTS

| | | |
|---|---|---|
| 2017/0000604 A1 | 1/2017 | Conklin et al. |
| 2017/0020670 A1 | 1/2017 | Murray et al. |
| 2017/0035562 A1 | 2/2017 | Quadri et al. |
| 2017/0035568 A1 | 2/2017 | Lombardi et al. |
| 2017/0056166 A1 | 3/2017 | Ratz et al. |
| 2017/0056171 A1 | 3/2017 | Cooper et al. |
| 2017/0071733 A1 | 3/2017 | Ghione et al. |
| 2017/0071736 A1 | 3/2017 | Zhu et al. |
| 2017/0076014 A1 | 3/2017 | Bressloff |
| 2017/0079786 A1 | 3/2017 | Li et al. |
| 2017/0079795 A1 | 3/2017 | Morrissey |
| 2017/0100246 A1 | 4/2017 | Rust et al. |
| 2017/0112620 A1 | 4/2017 | Curley et al. |
| 2017/0128208 A1 | 5/2017 | Christianson et al. |
| 2017/0143488 A1 | 5/2017 | Lashinski |
| 2017/0143489 A1 | 5/2017 | Lashinski |
| 2017/0165065 A1 | 6/2017 | Rothstein et al. |
| 2017/0172737 A1 | 6/2017 | Kuetting et al. |
| 2017/0172738 A1 | 6/2017 | Kassas |
| 2017/0181851 A1 | 6/2017 | Annest |
| 2017/0181852 A1 | 6/2017 | Kassas |
| 2017/0189177 A1 | 7/2017 | Schweich, Jr. et al. |
| 2017/0196690 A1 | 7/2017 | Racchini et al. |
| 2017/0209266 A1 | 7/2017 | Lane et al. |
| 2017/0209268 A1 | 7/2017 | Cunningham et al. |
| 2017/0216026 A1 | 8/2017 | Quill et al. |
| 2017/0216030 A1 | 8/2017 | Jonsson |
| 2017/0224480 A1 | 8/2017 | Garde et al. |
| 2017/0224486 A1 | 8/2017 | Delaloye et al. |
| 2017/0231755 A1 | 8/2017 | Gloss et al. |
| 2017/0231760 A1 | 8/2017 | Lane et al. |
| 2017/0239047 A1 | 8/2017 | Quill et al. |
| 2017/0245993 A1 | 8/2017 | Gross et al. |
| 2017/0245994 A1 | 8/2017 | Khairkhahan et al. |
| 2017/0252163 A1 | 9/2017 | Kheradvar |
| 2017/0258584 A1 | 9/2017 | Chang et al. |
| 2017/0258585 A1 | 9/2017 | Marquez et al. |
| 2017/0273784 A1 | 9/2017 | Racchini et al. |
| 2017/0281337 A1 | 10/2017 | Campbell |
| 2017/0281341 A1 | 10/2017 | Lim et al. |
| 2017/0296340 A1 | 10/2017 | Gross et al. |
| 2017/0325948 A1 | 11/2017 | Wallace et al. |
| 2017/0325976 A1 | 11/2017 | Nguyen et al. |
| 2017/0333184 A1 | 11/2017 | Ryan |
| 2017/0333240 A1 | 11/2017 | Stangenes et al. |
| 2017/0348099 A1 | 12/2017 | Mendelson et al. |
| 2017/0348100 A1 | 12/2017 | Lane et al. |
| 2017/0360557 A1 | 12/2017 | Kheradvar et al. |
| 2017/0360558 A1 | 12/2017 | Ma |
| 2017/0360561 A1 | 12/2017 | Bell et al. |
| 2018/0014932 A1 | 1/2018 | Hammer et al. |
| 2018/0021130 A1 | 1/2018 | Danino |
| 2018/0035971 A1 | 2/2018 | Brenner et al. |
| 2018/0042549 A1 | 2/2018 | Ho et al. |
| 2018/0042723 A1 | 2/2018 | Yellin et al. |
| 2018/0043133 A1 | 2/2018 | Wong |
| 2018/0049875 A1 | 2/2018 | Iflah et al. |
| 2018/0049876 A1 | 2/2018 | Miraki |
| 2018/0055628 A1 | 3/2018 | Patel et al. |
| 2018/0055633 A1 | 3/2018 | Costello et al. |
| 2018/0056045 A1 | 3/2018 | Donoghue et al. |
| 2018/0056046 A1 | 3/2018 | Kiersey et al. |
| 2018/0071088 A1 | 3/2018 | Badhwar et al. |
| 2018/0078367 A1 | 3/2018 | Saar et al. |
| 2018/0078368 A1 | 3/2018 | Vidlund et al. |
| 2018/0078370 A1 | 3/2018 | Kovalsky et al. |
| 2018/0085219 A1 | 3/2018 | Krivoruchko |
| 2018/0098837 A1 | 4/2018 | Shahriari |
| 2018/0099124 A1 | 4/2018 | McLoughlin et al. |
| 2018/0116793 A1 | 5/2018 | Salahieh et al. |
| 2018/0116843 A1 | 5/2018 | Schreck et al. |
| 2018/0125642 A1 | 5/2018 | White et al. |
| 2018/0125654 A1 | 5/2018 | Duffy |
| 2018/0126127 A1 | 5/2018 | Devereux et al. |
| 2018/0133000 A1 | 5/2018 | Scheinblum et al. |
| 2018/0133006 A1 | 5/2018 | Jones et al. |
| 2018/0133011 A1 | 5/2018 | Perouse |
| 2018/0140417 A1 | 5/2018 | Sciscio et al. |
| 2018/0147041 A1 | 5/2018 | Chouinard et al. |
| 2018/0147055 A1 | 5/2018 | Vidlund et al. |
| 2018/0153689 A1 | 6/2018 | Maimon et al. |
| 2018/0161158 A1 | 6/2018 | Kovalsky et al. |
| 2018/0161161 A1 | 6/2018 | Yellin et al. |
| 2018/0168793 A1 | 6/2018 | Lees et al. |
| 2018/0177580 A9 | 6/2018 | Shemesh et al. |
| 2018/0177594 A1 | 6/2018 | Patel et al. |
| 2018/0185153 A1 | 7/2018 | Bishop et al. |
| 2018/0193138 A1 | 7/2018 | Vidlund |
| 2018/0200049 A1 | 7/2018 | Chambers et al. |
| 2018/0206983 A1 | 7/2018 | Noe et al. |
| 2018/0214141 A1 | 8/2018 | Mendez |
| 2018/0221016 A1 | 8/2018 | Conklin et al. |
| 2018/0243071 A1 | 8/2018 | Eigler et al. |
| 2018/0243532 A1 | 8/2018 | Willard et al. |
| 2018/0256322 A1 | 9/2018 | Zhang et al. |
| 2018/0256327 A1 | 9/2018 | Perszyk et al. |
| 2018/0256329 A1 | 9/2018 | Chambers et al. |
| 2018/0263767 A1 | 9/2018 | Chau et al. |
| 2018/0263773 A1 | 9/2018 | Poppe et al. |
| 2018/0280174 A1 | 10/2018 | Dwork |
| 2018/0289474 A1 | 10/2018 | Rajagopal et al. |
| 2018/0289475 A1 | 10/2018 | Chung et al. |
| 2018/0289485 A1 | 10/2018 | Rajagopal et al. |
| 2018/0296325 A1 | 10/2018 | McLean |
| 2018/0296335 A1 | 10/2018 | Miyashiro |
| 2018/0296337 A1 | 10/2018 | Duhay et al. |
| 2018/0296341 A1 | 10/2018 | Noe et al. |
| 2018/0303488 A1 | 10/2018 | Hill |
| 2018/0303612 A1* | 10/2018 | Pasquino ............... A61F 2/2418 |
| 2018/0311037 A1 | 11/2018 | Morriss et al. |
| 2018/0311474 A1 | 11/2018 | Tyler, II et al. |
| 2018/0318073 A1 | 11/2018 | Tseng et al. |
| 2018/0318078 A1 | 11/2018 | Willard |
| 2018/0325665 A1 | 11/2018 | Gurovich et al. |
| 2018/0325671 A1 | 11/2018 | Abunassar et al. |
| 2018/0338832 A1 | 11/2018 | Ganesan et al. |
| 2018/0344456 A1 | 12/2018 | Barash et al. |
| 2018/0353293 A1 | 12/2018 | Colavito et al. |
| 2018/0353295 A1 | 12/2018 | Cooper et al. |
| 2018/0360439 A1 | 12/2018 | Niland et al. |
| 2018/0360599 A1 | 12/2018 | Drasler et al. |
| 2019/0000619 A1 | 1/2019 | Quijano et al. |
| 2019/0008640 A1 | 1/2019 | Cooper et al. |
| 2019/0015188 A1 | 1/2019 | Eigler et al. |
| 2019/0021834 A1 | 1/2019 | Nir et al. |
| 2019/0029819 A1 | 1/2019 | Huber |
| 2019/0029823 A1 | 1/2019 | Nguyen et al. |
| 2019/0038404 A1 | 2/2019 | Iamberger et al. |
| 2019/0038405 A1 | 2/2019 | Iamberger et al. |
| 2019/0053894 A1 | 2/2019 | Levi et al. |
| 2019/0053895 A1 | 2/2019 | Levi |
| 2019/0053897 A1 | 2/2019 | Levi et al. |
| 2019/0053898 A1 | 2/2019 | Maimon et al. |
| 2019/0053899 A1 | 2/2019 | Levi |
| 2019/0060051 A1 | 2/2019 | Scheeff et al. |
| 2019/0060057 A1 | 2/2019 | Cohen et al. |
| 2019/0060059 A1 | 2/2019 | Delgado et al. |
| 2019/0060069 A1 | 2/2019 | Maimon et al. |
| 2019/0060071 A1 | 2/2019 | Lane et al. |
| 2019/0069995 A1 | 3/2019 | Levi et al. |
| 2019/0070003 A1 | 3/2019 | Siegel et al. |
| 2019/0076233 A1 | 3/2019 | Fish |
| 2019/0076249 A1 | 3/2019 | Khairkhahan et al. |
| 2019/0083085 A1 | 3/2019 | Gilmore et al. |
| 2019/0091005 A1 | 3/2019 | Fifer et al. |
| 2019/0091015 A1 | 3/2019 | Dienno et al. |
| 2019/0091018 A1 | 3/2019 | Hariton et al. |
| 2019/0091022 A1 | 3/2019 | Yellin et al. |
| 2019/0099265 A1 | 4/2019 | Braido et al. |
| 2019/0099270 A1 | 4/2019 | Morrissey et al. |
| 2019/0105153 A1 | 4/2019 | Barash et al. |
| 2019/0117223 A1 | 4/2019 | Abunassar et al. |
| 2019/0117387 A1 | 4/2019 | Li et al. |
| 2019/0117391 A1 | 4/2019 | Humair |

(56) References Cited

U.S. PATENT DOCUMENTS

| | | | |
|---|---|---|---|
| 2019/0117400 A1 | 4/2019 | Medema et al. |
| 2019/0117401 A1 | 4/2019 | Cortez, Jr. et al. |
| 2019/0125287 A1 | 5/2019 | Itou et al. |
| 2019/0125536 A1 | 5/2019 | Prabhu et al. |
| 2019/0133528 A1 | 5/2019 | Kassab et al. |
| 2019/0133756 A1 | 5/2019 | Zhang et al. |
| 2019/0133757 A1 | 5/2019 | Zhang et al. |
| 2019/0133765 A1 | 5/2019 | Yellin et al. |
| 2019/0142566 A1 | 5/2019 | Lansky et al. |
| 2019/0142582 A1 | 5/2019 | Drasler et al. |
| 2019/0150867 A1 | 5/2019 | Itou et al. |
| 2019/0151509 A1 | 5/2019 | Kheradvar et al. |
| 2019/0167423 A1 | 6/2019 | Hariton et al. |
| 2019/0167429 A1 | 6/2019 | Stearns et al. |
| 2019/0175338 A1 | 6/2019 | White et al. |
| 2019/0175339 A1 | 6/2019 | Vidlund |
| 2019/0175344 A1 | 6/2019 | Khairkhahan |
| 2019/0183639 A1 | 6/2019 | Moore |
| 2019/0183644 A1 | 6/2019 | Hacohen |
| 2019/0183648 A1 | 6/2019 | Trapp et al. |
| 2019/0192287 A1 | 6/2019 | Sandstrom et al. |
| 2019/0192296 A1 | 6/2019 | Schwartz et al. |
| 2019/0209317 A1 | 7/2019 | Zhang et al. |
| 2019/0209320 A1 | 7/2019 | Drasler et al. |
| 2019/0231523 A1 | 8/2019 | Lombardi et al. |
| 2019/0240020 A1 | 8/2019 | Rafiee et al. |
| 2019/0240022 A1 | 8/2019 | Rafiee et al. |
| 2019/0247050 A1 | 8/2019 | Goldsmith |
| 2019/0254815 A1 | 8/2019 | Bruchman et al. |
| 2019/0254816 A1 | 8/2019 | Anderson et al. |
| 2019/0262118 A1 | 8/2019 | Eigler et al. |
| 2019/0262129 A1 | 8/2019 | Cooper et al. |
| 2019/0269413 A1 | 9/2019 | Yodfat et al. |
| 2019/0269504 A1 | 9/2019 | Wang et al. |
| 2019/0269839 A1 | 9/2019 | Wilson et al. |
| 2019/0282360 A1 | 9/2019 | Colavito et al. |
| 2019/0290426 A1 | 9/2019 | Maimon et al. |
| 2019/0290427 A1 | 9/2019 | Mantanus et al. |
| 2019/0307563 A1 | 10/2019 | Sandstrom et al. |
| 2019/0307589 A1 | 10/2019 | Goldberg et al. |
| 2019/0365538 A1 | 12/2019 | Chambers et al. |
| 2019/0388219 A1 | 12/2019 | Lane et al. |
| 2020/0121452 A1 | 4/2020 | Saikrishnan et al. |
| 2020/0121458 A1 | 4/2020 | Vidlund et al. |
| 2020/0179146 A1 | 6/2020 | Christianson et al. |
| 2020/0188097 A1 | 6/2020 | Perrin et al. |
| 2020/0237506 A1 | 7/2020 | Christianson et al. |
| 2020/0289259 A1 | 9/2020 | Christianson et al. |
| 2020/0289263 A1 | 9/2020 | Christianson et al. |
| 2021/0000592 A1 | 1/2021 | Christianson et al. |
| 2021/0137677 A1 | 5/2021 | Christianson et al. |
| 2021/0154011 A1 | 5/2021 | Christianson et al. |
| 2021/0186693 A1 | 6/2021 | Vidlund et al. |
| 2021/0220126 A1 | 7/2021 | Perrin |
| 2021/0220134 A1 | 7/2021 | Christianson et al. |
| 2021/0228349 A1 | 7/2021 | Vidlund et al. |
| 2021/0236280 A1 | 8/2021 | Christianson et al. |
| 2021/0244533 A1 | 8/2021 | Vidlund et al. |
| 2021/0244536 A1 | 8/2021 | Christianson et al. |
| 2021/0290381 A1 | 9/2021 | Vidlund et al. |
| 2021/0290385 A1 | 9/2021 | Christianson et al. |
| 2021/0315694 A1 | 10/2021 | Vidlund et al. |
| 2021/0330459 A1 | 10/2021 | Christianson et al. |

FOREIGN PATENT DOCUMENTS

| | | |
|---|---|---|
| AU | 2011238752 A1 | 10/2012 |
| AU | 2011240940 A1 | 10/2012 |
| AU | 2012272855 A1 | 1/2014 |
| AU | 2011236036 B2 | 6/2014 |
| AU | 2011248657 B2 | 12/2014 |
| AU | 2016228261 A1 | 4/2017 |
| AU | 2017210659 A1 | 8/2017 |
| AU | 2013245201 B2 | 10/2017 |
| AU | 2014360294 B2 | 10/2017 |
| AU | 2016249819 A1 | 11/2017 |
| AU | 2016371525 A1 | 5/2018 |
| AU | 2016366783 A1 | 6/2018 |
| AU | 2017214672 B2 | 10/2018 |
| AU | 2017285993 A1 | 1/2019 |
| AU | 2014201920 B2 | 2/2019 |
| AU | 2015411406 B2 | 2/2019 |
| AU | 2019202290 A1 | 4/2019 |
| AU | 2017388857 A1 | 8/2019 |
| BR | PI0909379 B1 | 9/2019 |
| CA | 2531528 A1 | 1/2005 |
| CA | 2609800 A1 | 1/2007 |
| CA | 2822636 A1 | 10/2008 |
| CA | 2398948 C | 8/2009 |
| CA | 2813419 A1 | 4/2012 |
| CA | 2856088 A1 | 5/2013 |
| CA | 2866315 A1 | 9/2013 |
| CA | 2922123 A1 | 4/2015 |
| CA | 2504258 C | 6/2015 |
| CA | 2677648 C | 10/2015 |
| CA | 2815331 C | 10/2015 |
| CA | 2986584 A1 | 11/2015 |
| CA | 2975294 A1 | 8/2016 |
| CA | 2995603 A1 | 2/2017 |
| CA | 2753853 C | 4/2017 |
| CA | 2702615 C | 6/2017 |
| CA | 2744395 C | 8/2017 |
| CA | 3020238 A1 | 11/2017 |
| CA | 3033666 A1 | 2/2018 |
| CA | 3031572 A1 | 3/2018 |
| CA | 3022641 A1 | 5/2018 |
| CA | 3044062 A1 | 6/2018 |
| CA | 3048893 A1 | 7/2018 |
| CA | 3049792 A1 | 7/2018 |
| CA | 3046693 A1 | 8/2018 |
| CA | 2778944 C | 8/2019 |
| CN | 2855366 Y | 1/2007 |
| CN | 100584292 C | 1/2010 |
| CN | 101677820 A | 3/2010 |
| CN | 101677851 A | 3/2010 |
| CN | 102858272 A | 1/2013 |
| CN | 102869320 A | 1/2013 |
| CN | 102892384 A | 1/2013 |
| CN | 103118630 A | 5/2013 |
| CN | 103189015 A | 7/2013 |
| CN | 103228231 A | 7/2013 |
| CN | 103298426 A | 9/2013 |
| CN | 103370035 A | 10/2013 |
| CN | 103391756 A | 11/2013 |
| CN | 102245120 B | 8/2014 |
| CN | 104220027 A | 12/2014 |
| CN | 102917668 B | 1/2015 |
| CN | 104394803 A | 3/2015 |
| CN | 104582637 A | 4/2015 |
| CN | 102905647 B | 7/2015 |
| CN | 103648570 B | 9/2015 |
| CN | 104884000 A | 9/2015 |
| CN | 104160076 B | 12/2015 |
| CN | 105380730 A | 3/2016 |
| CN | 105451687 A | 3/2016 |
| CN | 105520792 A | 4/2016 |
| CN | 105530893 A | 4/2016 |
| CN | 102458309 B | 5/2016 |
| CN | 103200900 B | 5/2016 |
| CN | 105555232 A | 5/2016 |
| CN | 105578992 A | 5/2016 |
| CN | 103338709 B | 6/2016 |
| CN | 105658178 A | 6/2016 |
| CN | 105792780 A | 7/2016 |
| CN | 103347467 B | 8/2016 |
| CN | 103648439 B | 8/2016 |
| CN | 103889472 B | 8/2016 |
| CN | 105899150 A | 8/2016 |
| CN | 103153232 B | 9/2016 |
| CN | 106061437 A | 10/2016 |
| CN | 106068109 A | 11/2016 |
| CN | 106073946 A | 11/2016 |
| CN | 106255475 A | 12/2016 |
| CN | 103917194 B | 2/2017 |

(56) References Cited

FOREIGN PATENT DOCUMENTS

| | | |
|---|---|---|
| CN | 106456324 A | 2/2017 |
| CN | 106456325 A | 2/2017 |
| CN | 105073068 B | 3/2017 |
| CN | 106470641 A | 3/2017 |
| CN | 105451684 B | 4/2017 |
| CN | 106573129 A | 4/2017 |
| CN | 103945792 B | 5/2017 |
| CN | 106659394 A | 5/2017 |
| CN | 106716098 A | 5/2017 |
| CN | 106794063 A | 5/2017 |
| CN | 106890035 A | 6/2017 |
| CN | 106943207 A | 7/2017 |
| CN | 106999054 A | 8/2017 |
| CN | 106999281 A | 8/2017 |
| CN | 104114127 B | 9/2017 |
| CN | 107115161 A | 9/2017 |
| CN | 107249482 A | 10/2017 |
| CN | 107260366 A | 10/2017 |
| CN | 104918582 B | 11/2017 |
| CN | 107374783 A | 11/2017 |
| CN | 107427364 A | 12/2017 |
| CN | 106255476 B | 1/2018 |
| CN | 107530157 A | 1/2018 |
| CN | 107530167 A | 1/2018 |
| CN | 107530177 A | 1/2018 |
| CN | 107613908 A | 1/2018 |
| CN | 104869948 B | 2/2018 |
| CN | 107714240 A | 2/2018 |
| CN | 107920897 A | 4/2018 |
| CN | 104853696 B | 6/2018 |
| CN | 108135696 A | 6/2018 |
| CN | 108430392 A | 8/2018 |
| CN | 108472142 A | 8/2018 |
| CN | 106726007 B | 11/2018 |
| CN | 109124829 A | 1/2019 |
| CN | 109199641 A | 1/2019 |
| CN | 109561962 A | 4/2019 |
| CN | 109567991 A | 4/2019 |
| CN | 109862835 A | 6/2019 |
| CN | 109906063 A | 6/2019 |
| CN | 109996581 A | 7/2019 |
| CN | 110013358 A | 7/2019 |
| CN | 110290764 A | 9/2019 |
| DE | 102014102648 A1 | 9/2015 |
| DE | 102014102650 A1 | 9/2015 |
| DE | 102014102718 A1 | 9/2015 |
| DE | 102014102722 A1 | 9/2015 |
| DE | 202017104793 U1 | 11/2018 |
| DE | 202016008737 U1 | 4/2019 |
| DK | 2549953 T3 | 2/2017 |
| DK | 2254514 T3 | 12/2018 |
| EA | 027348 B1 | 7/2017 |
| EP | 0902704 A4 | 3/1999 |
| EP | 1301225 A2 | 4/2003 |
| EP | 1684666 A2 | 8/2006 |
| EP | 1996246 A2 | 12/2008 |
| EP | 2211779 A1 | 8/2010 |
| EP | 2254513 A1 | 12/2010 |
| EP | 2263605 A1 | 12/2010 |
| EP | 2273947 A1 | 1/2011 |
| EP | 2296744 A1 | 3/2011 |
| EP | 2379008 A2 | 10/2011 |
| EP | 2400926 A2 | 1/2012 |
| EP | 2427145 A2 | 3/2012 |
| EP | 1582178 B1 | 9/2012 |
| EP | 2542186 A2 | 1/2013 |
| EP | 2558030 A1 | 2/2013 |
| EP | 2560579 A1 | 2/2013 |
| EP | 2575681 A1 | 4/2013 |
| EP | 2603172 A2 | 6/2013 |
| EP | 2637607 A1 | 9/2013 |
| EP | 2651337 A2 | 10/2013 |
| EP | 2658476 A1 | 11/2013 |
| EP | 2699201 A1 | 2/2014 |
| EP | 2405966 B1 | 4/2014 |
| EP | 2055263 B1 | 6/2014 |
| EP | 2741711 A2 | 6/2014 |
| EP | 2793763 A1 | 10/2014 |
| EP | 2822503 A2 | 1/2015 |
| EP | 2538879 B1 | 4/2015 |
| EP | 2444031 B1 | 7/2015 |
| EP | 1702247 B1 | 8/2015 |
| EP | 2772228 B1 | 11/2015 |
| EP | 2943160 A2 | 11/2015 |
| EP | 2470098 B1 | 12/2015 |
| EP | 1991168 B1 | 1/2016 |
| EP | 2254512 B1 | 1/2016 |
| EP | 2964152 A1 | 1/2016 |
| EP | 2967853 A1 | 1/2016 |
| EP | 2967860 A1 | 1/2016 |
| EP | 2994073 A1 | 3/2016 |
| EP | 3001978 A1 | 4/2016 |
| EP | 3003187 A1 | 4/2016 |
| EP | 3007649 A1 | 4/2016 |
| EP | 3010447 A1 | 4/2016 |
| EP | 3017792 A1 | 5/2016 |
| EP | 3019092 A1 | 5/2016 |
| EP | 2563236 B1 | 6/2016 |
| EP | 3027143 A1 | 6/2016 |
| EP | 3037064 A1 | 6/2016 |
| EP | 2211758 B1 | 7/2016 |
| EP | 3052053 A1 | 8/2016 |
| EP | 3060140 A1 | 8/2016 |
| EP | 3062745 A1 | 9/2016 |
| EP | 3071149 A1 | 9/2016 |
| EP | 2282700 B1 | 11/2016 |
| EP | 2967854 A1 | 11/2016 |
| EP | 1998713 B1 | 12/2016 |
| EP | 3099271 A1 | 12/2016 |
| EP | 3100701 A1 | 12/2016 |
| EP | 3141219 A1 | 3/2017 |
| EP | 3157469 A1 | 4/2017 |
| EP | 2538880 B1 | 5/2017 |
| EP | 2967852 B1 | 6/2017 |
| EP | 3174503 A1 | 6/2017 |
| EP | 3182931 A1 | 6/2017 |
| EP | 2830536 B1 | 8/2017 |
| EP | 2830537 B1 | 9/2017 |
| EP | 2720642 B1 | 10/2017 |
| EP | 3232941 A1 | 10/2017 |
| EP | 3256076 A1 | 12/2017 |
| EP | 3281608 A1 | 2/2018 |
| EP | 2608815 B1 | 3/2018 |
| EP | 3310302 A1 | 4/2018 |
| EP | 3311778 A1 | 4/2018 |
| EP | 3337412 A1 | 6/2018 |
| EP | 3340931 A1 | 7/2018 |
| EP | 3344188 A1 | 7/2018 |
| EP | 3344197 A1 | 7/2018 |
| EP | 3345573 A1 | 7/2018 |
| EP | 2822473 B1 | 8/2018 |
| EP | 3354208 A1 | 8/2018 |
| EP | 3370649 A1 | 9/2018 |
| EP | 3372198 A1 | 9/2018 |
| EP | 3372199 A1 | 9/2018 |
| EP | 3375411 A1 | 9/2018 |
| EP | 2928538 B1 | 11/2018 |
| EP | 3399947 A1 | 11/2018 |
| EP | 3400913 A1 | 11/2018 |
| EP | 3406224 A1 | 11/2018 |
| EP | 2555709 B1 | 12/2018 |
| EP | 3417813 A1 | 12/2018 |
| EP | 3426188 A1 | 1/2019 |
| EP | 3429507 A1 | 1/2019 |
| EP | 3431040 A1 | 1/2019 |
| EP | 3432825 A1 | 1/2019 |
| EP | 3432834 A1 | 1/2019 |
| EP | 3437669 A1 | 2/2019 |
| EP | 3448312 A1 | 3/2019 |
| EP | 3454787 A1 | 3/2019 |
| EP | 2663259 B1 | 5/2019 |
| EP | 3302364 B1 | 5/2019 |
| EP | 3478224 A1 | 5/2019 |
| EP | 3484411 A1 | 5/2019 |

(56) References Cited

FOREIGN PATENT DOCUMENTS

| | | |
|---|---|---|
| EP | 3487420 A1 | 5/2019 |
| EP | 2560580 B1 | 6/2019 |
| EP | 3508113 A1 | 7/2019 |
| EP | 3518748 A1 | 8/2019 |
| EP | 3522830 A1 | 8/2019 |
| EP | 3528749 A1 | 8/2019 |
| EP | 3288495 B1 | 9/2019 |
| EP | 3538024 A1 | 9/2019 |
| EP | 3538025 A1 | 9/2019 |
| EP | 3019123 B1 | 10/2019 |
| EP | 3552584 A1 | 10/2019 |
| EP | 3552655 A1 | 10/2019 |
| ES | 2369241 T3 | 11/2011 |
| ES | 2647777 T3 | 12/2017 |
| ES | 2664243 T3 | 4/2018 |
| ES | 2675726 T3 | 7/2018 |
| GB | 2539444 A | 12/2016 |
| JP | 2003530956 A | 10/2003 |
| JP | 2005521513 A | 7/2005 |
| JP | 2008506459 A | 3/2008 |
| JP | 2008512211 A | 4/2008 |
| JP | 2009148579 A | 7/2009 |
| JP | 2009525138 A | 7/2009 |
| JP | 2009527316 A | 7/2009 |
| JP | 2009254864 A | 11/2009 |
| JP | 4426182 B2 | 3/2010 |
| JP | 2010518947 A | 6/2010 |
| JP | 2010537680 A | 12/2010 |
| JP | 2011510797 A | 4/2011 |
| JP | 2013503009 A | 1/2013 |
| JP | 2013505082 A | 2/2013 |
| JP | 2013508027 A | 3/2013 |
| JP | 2013512765 A | 4/2013 |
| JP | 2013523261 A | 6/2013 |
| JP | 2013527010 A | 6/2013 |
| JP | 2013543399 A | 12/2013 |
| JP | 2014501563 A | 1/2014 |
| JP | 2014505537 A | 3/2014 |
| JP | 5527850 B2 | 6/2014 |
| JP | 2014518697 A | 8/2014 |
| JP | 2014522678 A | 9/2014 |
| JP | 2015503948 A | 2/2015 |
| JP | 2015510819 A | 4/2015 |
| JP | 2015517854 A | 6/2015 |
| JP | 5767764 B2 | 8/2015 |
| JP | 5803010 B2 | 11/2015 |
| JP | 2015531283 A | 11/2015 |
| JP | 2015534887 A | 12/2015 |
| JP | 2016503710 A | 2/2016 |
| JP | 2016506794 A | 3/2016 |
| JP | 2016508858 A | 3/2016 |
| JP | 2016517748 A | 6/2016 |
| JP | 2016520391 A | 7/2016 |
| JP | 2016526438 A | 9/2016 |
| JP | 2016530046 A | 9/2016 |
| JP | 2016533787 A | 11/2016 |
| JP | 2016540617 A | 12/2016 |
| JP | 2017000729 A | 1/2017 |
| JP | 2017504410 A | 2/2017 |
| JP | 2017515609 A | 6/2017 |
| JP | 2017516536 A | 6/2017 |
| JP | 2017516609 A | 6/2017 |
| JP | 2017131738 A | 8/2017 |
| JP | 2017159055 A | 9/2017 |
| JP | 2017529908 A | 10/2017 |
| JP | 2018501001 A | 1/2018 |
| JP | 2018501901 A | 1/2018 |
| JP | 2018506412 A | 3/2018 |
| JP | 6329570 B2 | 5/2018 |
| JP | 2018515306 A | 6/2018 |
| JP | 2018118136 A | 8/2018 |
| JP | 2018532556 A | 11/2018 |
| JP | 2018535074 A | 11/2018 |
| JP | 2019500952 A | 1/2019 |
| JP | 2019501696 A | 1/2019 |
| JP | 2019501712 A | 1/2019 |
| JP | 6466853 B2 | 2/2019 |
| JP | 6480343 B2 | 3/2019 |
| JP | 2019507664 A | 3/2019 |
| JP | 6506813 B2 | 4/2019 |
| JP | 6526043 B2 | 6/2019 |
| JP | 2019103821 A | 6/2019 |
| JP | 2019514490 A | 6/2019 |
| JP | 2019516527 A | 6/2019 |
| JP | 2019517346 A | 6/2019 |
| JP | 6568213 B2 | 8/2019 |
| JP | 2019134972 A | 8/2019 |
| JP | 2019523090 A | 8/2019 |
| JP | 2019155178 A | 9/2019 |
| JP | 2019526303 A | 9/2019 |
| KR | 20010013991 A | 2/2001 |
| KR | 20120101625 A | 9/2012 |
| KR | 101223313 B1 | 1/2013 |
| KR | 101354189 B1 | 1/2014 |
| KR | 20140139060 A | 12/2014 |
| KR | 20150097757 A | 8/2015 |
| KR | 20160024992 A | 3/2016 |
| RU | 177405 U1 | 2/2018 |
| WO | WO-0044308 A2 | 8/2000 |
| WO | WO-03072287 A1 | 9/2003 |
| WO | WO-2004093728 A2 | 11/2004 |
| WO | WO-2006029062 A1 | 3/2006 |
| WO | WO-2006066150 A2 | 6/2006 |
| WO | WO-2007047945 A2 | 4/2007 |
| WO | WO-2007054015 A1 | 5/2007 |
| WO | WO-2007095233 A2 | 8/2007 |
| WO | WO-2007129220 A2 | 11/2007 |
| WO | WO-2008013915 A2 | 1/2008 |
| WO | WO-2008091925 A2 | 7/2008 |
| WO | WO-2008103280 A2 | 8/2008 |
| WO | WO-2009081396 A2 | 7/2009 |
| WO | WO-2009094188 A2 | 7/2009 |
| WO | WO-2009094189 A1 | 7/2009 |
| WO | WO-2009094197 A1 | 7/2009 |
| WO | WO-2009094501 A1 | 7/2009 |
| WO | WO-2009100242 A2 | 8/2009 |
| WO | WO-2010029190 A1 | 3/2010 |
| WO | WO-2010119110 A1 | 10/2010 |
| WO | WO-2011112706 A2 | 9/2011 |
| WO | WO-2011137531 A1 | 11/2011 |
| WO | WO-2012009558 A2 | 1/2012 |
| WO | WO 2012/035279 | 3/2012 |
| WO | WO-2012063228 A1 | 5/2012 |
| WO | WO-2012063242 A1 | 5/2012 |
| WO | WO-2012112469 A2 | 8/2012 |
| WO | WO-2012145545 A1 | 10/2012 |
| WO | WO-2012161786 A1 | 11/2012 |
| WO | WO-2012175483 A1 | 12/2012 |
| WO | WO-2012178115 A2 | 12/2012 |
| WO | WO-2013021375 A2 | 2/2013 |
| WO | WO-2013085719 A1 | 6/2013 |
| WO | WO-2013103612 A1 | 7/2013 |
| WO | WO-2013116785 A1 | 8/2013 |
| WO | WO-2013128436 A1 | 9/2013 |
| WO | WO-2013148019 A1 | 10/2013 |
| WO | WO-2013166356 A2 | 11/2013 |
| WO | WO-2013177684 A1 | 12/2013 |
| WO | WO-2013184945 A1 | 12/2013 |
| WO | WO-2014011330 A1 | 1/2014 |
| WO | WO-2014064695 A2 | 5/2014 |
| WO | WO-2014121042 A1 | 8/2014 |
| WO | WO-2014133667 A1 | 9/2014 |
| WO | WO-2014137805 A1 | 9/2014 |
| WO | WO-2014140230 A1 | 9/2014 |
| WO | WO-2014162306 A2 | 10/2014 |
| WO | WO-2014164151 A1 | 10/2014 |
| WO | WO-2014168655 A1 | 10/2014 |
| WO | WO-2015004173 A1 | 1/2015 |
| WO | WO-2015014960 A1 | 2/2015 |
| WO | WO-2015017075 A1 | 2/2015 |
| WO | WO-2015055605 A1 | 4/2015 |
| WO | WO-2015057735 A1 | 4/2015 |
| WO | WO-2015058039 A1 | 4/2015 |
| WO | WO-2015061021 A1 | 4/2015 |

(56) References Cited

FOREIGN PATENT DOCUMENTS

| | | |
|---|---|---|
| WO | WO-2015117025 A1 | 8/2015 |
| WO | WO-2015120122 A2 | 8/2015 |
| WO | WO-2015123607 A2 | 8/2015 |
| WO | WO-2015127264 A1 | 8/2015 |
| WO | WO-2015142834 A1 | 9/2015 |
| WO | WO-2015153755 A2 | 10/2015 |
| WO | WO-2016011267 A1 | 1/2016 |
| WO | WO-2016025733 A1 | 2/2016 |
| WO | WO-2016083351 A1 | 6/2016 |
| WO | WO-2016097337 A1 | 6/2016 |
| WO | WO-2016100799 A1 | 6/2016 |
| WO | WO-2016118851 A1 | 7/2016 |
| WO | WO-2016130913 A1 | 8/2016 |
| WO | WO-2016148777 A1 | 9/2016 |
| WO | WO-2016149083 A1 | 9/2016 |
| WO | WO-2016150806 A1 | 9/2016 |
| WO | WO-2016189391 A2 | 12/2016 |
| WO | WO-2017040684 A1 | 3/2017 |
| WO | WO-2017096157 A1 | 6/2017 |
| WO | WO-2017114928 A1 | 7/2017 |
| WO | WO-2017120404 A1 | 7/2017 |
| WO | WO-2017121193 A1 | 7/2017 |
| WO | WO-2017121194 A1 | 7/2017 |
| WO | WO-2017121195 A1 | 7/2017 |
| WO | WO-2017136596 A1 | 8/2017 |
| WO | WO-2017151292 A1 | 9/2017 |
| WO | WO-2017155892 A1 | 9/2017 |
| WO | WO-2017156352 A1 | 9/2017 |
| WO | WO-2017161204 A1 | 9/2017 |
| WO | WO-2017165842 A1 | 9/2017 |
| WO | WO-2017196511 A1 | 11/2017 |
| WO | WO-2017201082 A1 | 11/2017 |
| WO | WO-2017202042 A1 | 11/2017 |
| WO | WO-2017210356 A1 | 12/2017 |
| WO | WO-2017218375 A1 | 12/2017 |
| WO | WO-2018008019 A2 | 1/2018 |
| WO | WO-2018026445 A1 | 2/2018 |
| WO | WO-2018026904 A1 | 2/2018 |
| WO | WO-2018035105 A1 | 2/2018 |
| WO | WO-2018040244 A1 | 3/2018 |
| WO | WO-2018042439 A1 | 3/2018 |
| WO | WO-2018045156 A2 | 3/2018 |
| WO | WO-2018071115 A1 | 4/2018 |
| WO | WO-2018077143 A1 | 5/2018 |
| WO | WO-2018077146 A1 | 5/2018 |
| WO | WO-2018080328 A1 | 5/2018 |
| WO | WO-2018083493 A1 | 5/2018 |
| WO | WO-2018090576 A1 | 5/2018 |
| WO | WO-2018098032 A1 | 5/2018 |
| WO | WO-2018106460 A1 | 6/2018 |
| WO | WO-2018119304 A1 | 6/2018 |
| WO | WO-2018138658 A1 | 8/2018 |
| WO | WO-2018145055 A1 | 8/2018 |
| WO | WO-2018156767 A1 | 8/2018 |
| WO | WO-2018156922 A1 | 8/2018 |
| WO | WO-2018158747 A1 | 9/2018 |
| WO | WO-2018160790 A1 | 9/2018 |
| WO | WO-2018165358 A1 | 9/2018 |
| WO | WO-2018170149 A1 | 9/2018 |
| WO | WO-2018175220 A1 | 9/2018 |
| WO | WO-2018175619 A1 | 9/2018 |
| WO | WO-2018178208 A1 | 10/2018 |
| WO | WO-2018178977 A1 | 10/2018 |
| WO | WO-2018183832 A1 | 10/2018 |
| WO | WO-2018184225 A1 | 10/2018 |
| WO | WO-2018184226 A1 | 10/2018 |
| WO | WO-2018187495 A1 | 10/2018 |
| WO | WO-2018187753 A1 | 10/2018 |
| WO | WO-2018191681 A1 | 10/2018 |
| WO | WO-2018200531 A1 | 11/2018 |
| WO | WO-2018200942 A2 | 11/2018 |
| WO | WO-2018201111 A2 | 11/2018 |
| WO | WO-2018201212 A1 | 11/2018 |
| WO | WO-2018204106 A1 | 11/2018 |
| WO | WO-2018209302 A1 | 11/2018 |
| WO | WO-2018213209 A1 | 11/2018 |
| WO | WO-2018217525 A1 | 11/2018 |
| WO | WO-2018222799 A1 | 12/2018 |
| WO | WO-2018226628 A1 | 12/2018 |
| WO | WO-2019003221 A1 | 1/2019 |
| WO | WO-2019006383 A2 | 1/2019 |
| WO | WO-2019010458 A1 | 1/2019 |
| WO | WO-2019014473 A1 | 1/2019 |
| WO | WO-2019018319 A1 | 1/2019 |
| WO | WO-2019023385 A1 | 1/2019 |
| WO | WO-2019026059 A1 | 2/2019 |
| WO | WO-2019032992 A2 | 2/2019 |
| WO | WO-2019037579 A1 | 2/2019 |
| WO | WO-2019040357 A1 | 2/2019 |
| WO | WO-2019042472 A1 | 3/2019 |
| WO | WO-2019046099 A1 | 3/2019 |
| WO | WO-2019046205 A1 | 3/2019 |
| WO | WO-2019051168 A2 | 3/2019 |
| WO | WO-2019051180 A2 | 3/2019 |
| WO | WO-2019051587 A1 | 3/2019 |
| WO | WO-2019055577 A1 | 3/2019 |
| WO | WO-2019058178 A1 | 3/2019 |
| WO | WO-2019067219 A1 | 4/2019 |
| WO | WO-2019081689 A1 | 5/2019 |
| WO | WO-2019081985 A2 | 5/2019 |
| WO | WO-2019086958 A1 | 5/2019 |
| WO | WO-2019089136 A1 | 5/2019 |
| WO | WO-2019089821 A1 | 5/2019 |
| WO | WO-2019093387 A1 | 5/2019 |
| WO | WO-2019095049 A1 | 5/2019 |
| WO | WO-2019096033 A1 | 5/2019 |
| WO | WO-2019099722 A2 | 5/2019 |
| WO | WO-2019116322 A1 | 6/2019 |
| WO | WO-2019119674 A1 | 6/2019 |
| WO | WO-2019126518 A1 | 6/2019 |
| WO | WO-2019131148 A1 | 7/2019 |
| WO | WO-2019136162 A1 | 7/2019 |
| WO | WO-2019140293 A1 | 7/2019 |
| WO | WO-2019143775 A1 | 7/2019 |
| WO | WO-2019144036 A1 | 7/2019 |
| WO | WO-2019147585 A1 | 8/2019 |
| WO | WO-2019165213 A1 | 8/2019 |
| WO | WO-2019173475 A1 | 9/2019 |
| WO | WO 2019/195860 | 10/2019 |
| WO | WO-2019190800 A1 | 10/2019 |
| WO | WO-2019191102 A1 | 10/2019 |

OTHER PUBLICATIONS

International Search Report and Written Opinion for International Application No. PCT/US2019/051615, dated Mar. 2, 2020, 14 pages.
International Search Report and Written Opinion for International Application No. PCT/US2019/051957, dated Apr. 30, 2020, 16 pages.
Office Action for U.S. Appl. No. 16/155,890, dated Feb. 8, 2019, 13 pages.
Office Action for U.S. Appl. No. 16/448,108, dated Jan. 21, 2020, 14 pages.
Office Action for U.S. Appl. No. 16/448,108, dated Sep. 1, 2020, 14 pages.
Office Action for U.S. Appl. No. 16/455,417, dated Sep. 23, 2019, 11 pages.
International Search Report and Written Opinion for International Application No. PCT/US2019/067010, dated Mar. 10, 2020, 17 pages.
Office Action for U.S. Appl. No. 16/455,740, dated Jul. 24, 2020, 7 pages.
International Search Report and Written Opinion for International Application No. PCT/US2020/015231, dated Apr. 23, 2020, 10 pages.
International Search Report and Written Opinion for International Application No. PCT/US2020/021300, dated Oct. 7, 2020, 6 pages.
International Search Report and Written Opinion for International Application No. PCT/US2020/031390, dated Aug. 3, 2020, 10 pages.

(56) References Cited

OTHER PUBLICATIONS

International Search Report and Written Opinion for International Application No. PCT/US2020/013240, dated Jun. 3, 2020, 7 pages.
International Search Report and Written Opinion for International Application No. PCT/US2020/022828, dated May 19, 2020, 12 pages.
Office Action for U.S. Appl. No. 16/442,504, dated Jan. 14, 2020, 11 pages.
International Search Report and Written Opinion for International Application No. PCT/US2020/045195, dated Jan. 8, 2021, 18 pages.
International Search Report and Written Opinion for International Application No. PCT/US2020/047162, dated Dec. 30, 2020, 9 pages.
Office Action for U.S. Appl. No. 16/445,210, dated Jan. 28, 2021, 7 pages.
Office Action for U.S. Appl. No. 16/448,108, dated Mar. 8, 2021, 8 pages.
Office Action for U.S. Appl. No. 16/163,577, dated Mar. 8, 2021, 10 pages.
Office Action for U.S. Appl. No. 17/154,227, dated Mar. 29, 2021, 6 pages.
International Search Report and Written Opinion for International Application No. PCT/US2021/013570, dated Apr. 1, 2021, 9 pages.
International Search Report and Written Opinion for International Application No. PCT/US2019/028822, dated Oct. 24, 2019, 14 pages.
Office Action for U.S. Appl. No. 17/167,983, dated Apr. 13, 2021, 20 pages.
Office Action for U.S. Appl. No. 17/154,438, dated May 3, 2021, 16 pages.
Office Action for U.S. Appl. No. 17/193,936, dated May 27, 2021, 6 pages.
Office Action for U.S. Appl. No. 16/449,420, dated Sep. 1, 2021, 16 pages.
Office Action for U.S. Appl. No. 17/222,182, dated Sep. 2, 2021, 23 pages.
Office Action for U.S. Appl. No. 17/236,219, dated Aug. 4, 2021, 17 pages.
Office Action for U.S. Appl. No. 17/154,227, dated Jun. 18, 2021, 8 pages.
Office Action for U.S. Appl. No. 17/167,988, dated Sep. 22, 2021, 19 pages.
Office Action for U.S. Appl. No. 17/222,430, dated Oct. 7, 2021, 17 pages.
Office Action for U.S. Appl. No. 16/443,862, dated Nov. 12, 2021, 9 pages.

* cited by examiner

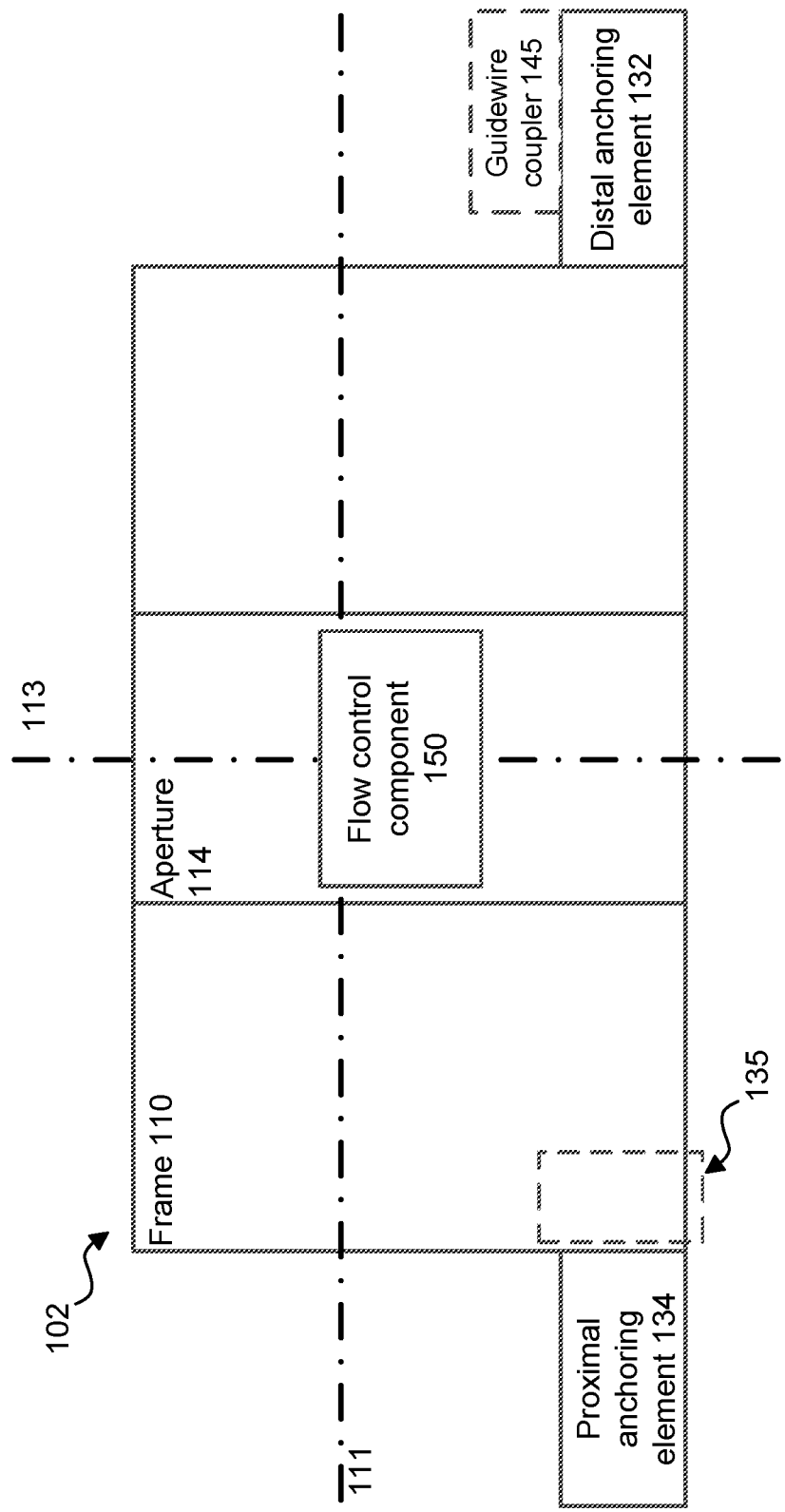

proximal view distal view anterior side septal side

Dispose adjacent to an annulus of a native valve a distal end of a delivery catheter having disposed in a lumen thereof a prosthetic heart valve in a compressed configuration
11

↓

Release the prosthetic heart valve from the lumen of the delivery catheter such that the prosthetic heart valve transitions from the compressed configuration to an expanded configuration
12

↓

Place a portion of a distal anchoring element on a ventricle side of the annulus of the native valve
13

↓

Seat the prosthetic heart valve in the annulus when a proximal anchoring element is in a first configuration
14

↓

Transition the proximal anchoring element from a first configuration to a second configuration after seating the prosthetic heart valve in the annulus
15

PROXIMAL TAB FOR SIDE-DELIVERED TRANSCATHETER HEART VALVES AND METHODS OF DELIVERY

CROSS-REFERENCE TO RELATED APPLICATIONS

This application is a continuation of International Patent Application No. PCT/US2019/067010, entitled "Proximal Tab for Side-Delivered Transcatheter Heart Valves and Methods of Delivery," filed Dec. 18, 2019, which is a continuation-in-part of U.S. application Ser. No. 16/455,417, entitled "Proximal Tab for Side-Delivered Transcatheter Heart Valve Prosthesis," filed Jun. 27, 2019, which claims priority to U.S. Provisional Application Ser. No. 62/782,350, entitled "Proximal Tab for Side-Delivered Transcatheter Heart Valve Prosthesis," filed Dec. 20, 2018. International Patent Application No. PCT/US2019/067010 also claims priority to U.S. Provisional Application Ser. No. 62/782,350. This application is also a continuation-in-part of U.S. application Ser. No. 16/877,457, entitled "Proximal Tab for Side-Delivered Transcatheter Heart Valve Prosthesis," filed May 18, 2020, which is a continuation of U.S. application Ser. No. 16/455,417, entitled "Proximal Tab for Side-Delivered Transcatheter Heart Valve Prosthesis," filed Jun. 27, 2019. The disclosure of each of the foregoing applications is incorporated herein by reference in its entirety.

BACKGROUND

Embodiments are described herein that relate to prosthetic heart valves, and devices and methods for use in the delivery and deployment of such valves.

Prosthetic heart valves can pose challenges for delivery and deployment within a heart, particularly for delivery by catheters through the patient's vasculature rather than through a surgical approach. Delivery of traditional transcatheter prosthetic valves generally includes compressing the valve in a radial direction and loading the valve into a delivery catheter such that a central annular axis of the valve is parallel to the lengthwise axis of the delivery catheter. The valves are deployed from the end of the delivery catheter and expanded outwardly in a radial direction from the central annular axis. The expanded size (e.g., diameter) of traditional valves, however, can be limited by the internal diameter of the delivery catheter. The competing interest of minimizing delivery catheter size presents challenges to increasing the expanded diameter of traditional valves (e.g., trying to compress too much material and structure into too little space).

Accordingly, a need exists for prosthetic valves with one or more anchoring features while maintaining a relatively small compressed size that allows for transcatheter delivery of the valve.

SUMMARY

The embodiments described herein relate generally to transcatheter prosthetic valves and methods for delivering transcatheter prosthetic valves. In some embodiments, a prosthetic heart valve includes a valve frame defining an aperture that extends along a central axis and a flow control component mounted within the aperture. The flow control component is configured to permit blood flow in a first direction approximately parallel to the central axis from an inflow end to an outflow end of the flow control component and block blood flow in a second direction, opposite the first direction. The valve frame includes a distal anchoring element and a proximal anchoring element. The valve frame has a compressed configuration to allow the prosthetic heart valve to be delivered to a heart of a patient via a delivery catheter. The valve frame is configured to transition from the compressed configuration to an expanded configuration when the prosthetic heart valve is released from the delivery catheter. The prosthetic heart valve is configured to be seated in an annulus of a native valve of the heart when in the expanded configuration. The distal anchoring element and the proximal anchoring element of the valve frame configured to be inserted through the annulus of the native valve prior to the prosthetic heart valve being seated therein. The proximal anchoring element is configured to be transitioned from a first configuration to a second configuration after the prosthetic valve is seated in the annulus of the native valve.

The embodiments described herein relate generally to transcatheter prosthetic valves configured for side/orthogonal delivery, which can have an increased expanded diameter relative to traditional valves. For example, in side delivery, the valve is compressed and loaded into a delivery catheter such that a central annular axis of the valve is substantially orthogonal to the lengthwise axis of the delivery catheter, which can allow the valve to be compressed laterally and extended longitudinally (e.g., in a direction parallel to the lengthwise axis of the delivery catheter. With traditional and/or orthogonally delivered transcatheter prosthetic valves it is also desirable to provide one or more ways of anchoring the valve in the native annuls without substantially increasing a compressed size of the valve.

BRIEF DESCRIPTION OF THE DRAWINGS

FIGS. 1A-1C are schematic illustrations of a transcatheter prosthetic valve according to an embodiment.

FIG. 33 is a flowchart illustrating a method of delivering a transcatheter prosthetic valve according to an embodiment.

DETAILED DESCRIPTION

Figure 1B:
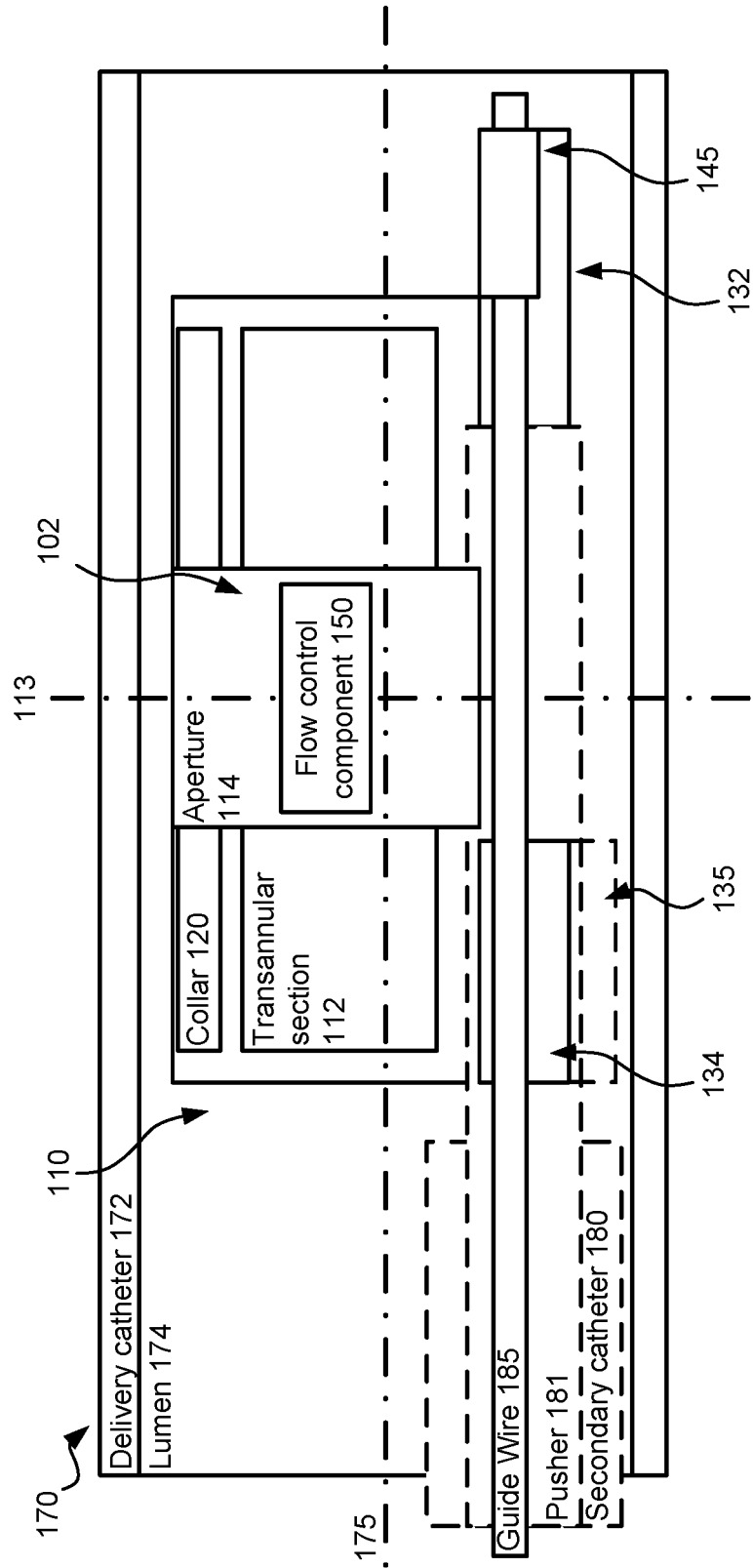

Disclosed embodiments are directed to transcatheter prosthetic heart valves and/or components thereof, and methods of manufacturing, loading, delivering, and/or deploying the transcatheter prosthetic valves and/or components thereof. The transcatheter prosthetic heart valves can have a valve frame and a flow control component mounted within a central lumen or aperture of the valve frame. The flow control component can be configured to permit blood flow in a first direction through an inflow end of the valve and block blood flow in a second direction, opposite the first direction, through an outflow end of the valve. The valves can be compressible and expandable along a long-axis substantially parallel to a lengthwise cylindrical axis of a delivery catheter. The valves can be configured to transition between a compressed configuration for introduction into the body using the delivery catheter, and an expanded configuration for implanting at a desired location in the body.

In some implementations, the embodiments described herein are directed to a dual-tab prosthetic heart valve that is a low profile, side delivered implantable prosthetic heart valve. The prosthetic heart valves can have at least a ring-shaped or annular valve frame, an inner flow control component (e.g., a 2-leaflet or 3-leaflet sleeve, and/or the like) mounted in the valve frame, a distal anchoring element (e.g., a sub-annular distal anchoring tab or the like) configured to extend into the right ventricular outflow tract (RVOT), and a proximal anchoring element (e.g., a sub-annular proximal anchoring tab) configured to extend into the proximal sub-annular space, preferably between the anterior and the posterior leaflets of the heart.

Any of the prosthetic heart valves described herein can be configured to transition between an expanded configuration and a compressed configuration. For example, any of the embodiments described herein can be a balloon-inflated prosthetic heart valve, a self-expanding prosthetic heart valve, and/or the like.

Any of the prosthetic heart valves described herein can be compressible—into the compressed configuration—in a lengthwise or orthogonal direction relative to the central axis of the flow control component that can allow a large diameter valve (e.g., having a height of about 5-60 mm and a diameter of about 20-80 mm) to be delivered and deployed from the inferior vena cava directly into the annulus of a native mitral or tricuspid valve using, for example, a 24-36Fr delivery catheter and without delivery and deployment from the delivery catheter at an acute angle of approach.

Any of the prosthetic heart valves described herein can have a central axis when in a compressed configuration that is co-axial or at least substantially parallel with blood flow direction through the valve. In some embodiments, the compressed configuration of the valve is orthogonal to the blood flow direction. In some embodiments, a long-axis is oriented at an intersecting angle of between 45-135 degrees to the first direction when in the compressed configuration and/or the expanded configuration.

Any of the prosthetic heart valves described herein can include an anchoring element extending from a distal side of the tubular frame, which can be used, for example, as a Right Ventricular Outflow Tract ("RVOT") tab or a Left Ventricular Outflow Tract ("LVOT"). The anchoring element can include and/or can be formed from a wire loop or wire frame, an integrated frame section, and/or a stent, extending from about 10-40 mm away from the tubular frame.

Any of the prosthetic heart valves described herein can include (i) an upper anchoring element attached to a distal upper edge of the tubular frame, the upper anchoring element can include or be formed from a wire loop or wire frame extending from about 2-20 mm away from the tubular frame, and (ii) a lower anchoring element (e.g., used as a RVOT tab) extending from a distal side of the tubular frame, the lower anchoring element can include and/or can be formed from a wire loop or wire frame extending from about 10-40 mm away from the tubular frame.

Any of the prosthetic heart valves described herein can include a distal lower anchoring element configured to be positioned into the RVOT of the right ventricle and a proximal lower anchoring element configured to be positioned into a sub-annular position in contact with and/or adjacent to sub-annular tissue of the right ventricle. The catheter prosthetic heart valve can also include a distal upper anchoring element configured to be positioned into a supra-annular position in contact with and/or adjacent to supra-annular tissue of the right atrium. The distal upper anchoring element can provide a supra-annular downward force in the direction of the right ventricle and the distal and proximal lower anchoring elements can provide a sub-annular upward force in the direction of the right atrium.

Any of the prosthetic heart valves described herein and/or any component, feature, and/or aspect thereof can be similar to and/or substantially the same as the prosthetic heart valves (or components, features, and/or aspects thereof) described in International Patent Application No. PCT/US2019/051957, entitled "Transcatheter Deliverable Prosthetic Heart Valves and Method of Delivery," filed Sep. 19, 2019 (referred to herein as "the '957 PCT"), the disclosure of which is incorporated herein by reference in its entirety.

Any method for delivering prosthetic heart valves described herein can include side/orthogonal delivery of the prosthetic heart valve to a desired location in the body that includes (i) advancing a delivery catheter to the desired location in the body and (ii) delivering the prosthetic heart valve to the desired location in the body by releasing the valve from the delivery catheter. The valve is in a compressed configuration when in the delivery catheter and transitions to an expanded configuration when released from the delivery catheter.

Any method for delivering prosthetic heart valves described herein can include attaching a pulling wire (e.g., a rigid elongated pulling/pushing rod or draw wire) to a sidewall or an anchoring element (e.g., a distal anchoring element) of the prosthetic heart valve and pulling the valve into and/or through a delivery catheter.

Any method for delivering prosthetic heart valves described herein can include releasing the valve from the delivery catheter by (i) pulling the valve out of the delivery catheter using a pulling wire or rod that is releasably connected to a sidewall or an anchoring element, wherein advancing the pulling wire away from the delivery catheter pulls the compressed valve out of the delivery catheter, or (ii) pushing the valve out of the delivery catheter using a pushing wire or rod that is releasably connected to a sidewall or an anchoring element, wherein advancing the pushing wire or rod out of from the delivery catheter pushes the compressed valve out of the delivery catheter.

Any method for delivering prosthetic heart valves described herein can include releasing the valve from a delivery catheter while increasing blood flow during deployment of the valve by (i) partially releasing the valve from the delivery catheter to establish blood flow around the partially released valve and blood flow through the flow control component; (ii) completely releasing the valve from the delivery catheter while maintaining attachment to the valve to transition to a state with increased blood flow through the flow control component and decreased blood flow around the valve; (iii) deploying the valve into a final mounted position in a native annulus to transition to a state with complete blood flow through the flow control component and minimal or no blood flow around the valve; and (iv) disconnecting and withdrawing a positioning catheter, pulling or pushing wire or rod, and/or the delivery catheter.

Any method for delivering prosthetic heart valves described herein can include orthogonal delivery of the prosthetic heart valve to a native annulus of a human heart that includes at least one of (i) advancing the delivery catheter to the tricuspid valve or pulmonary artery of the heart through the inferior vena cava (IVC) via the femoral vein, (ii) advancing to the tricuspid valve or pulmonary artery of the heart through the superior vena cava (SVC) via the jugular vein, or (iii) advancing to the mitral valve of the heart through a trans-atrial approach (e.g., fossa ovalis or lower), via the IVC-femoral or the SVC jugular approach; and (iv) delivering prosthetic heart valve to the native annulus by releasing the valve from the delivery catheter.

Any method for delivering prosthetic heart valves described herein and/or any portion thereof can be similar to and/or substantially the same as one or more methods for delivering prosthetic heart valves (or portion(s) thereof) described in the '957 PCT.

In some embodiments, a prosthetic heart valve includes a valve frame defining an aperture that extends along a central axis and a flow control component mounted within the aperture. The flow control component is configured to permit blood flow in a first direction approximately parallel to the central axis from an inflow end to an outflow end of the flow control component and block blood flow in a second direction, opposite the first direction. The valve frame includes a distal anchoring element and a proximal anchoring element. The valve frame has a compressed configuration to allow the prosthetic heart valve to be delivered to a heart of a patient via a delivery catheter. The valve frame is configured to transition from the compressed configuration to an expanded configuration when the prosthetic heart valve is released from the delivery catheter. The prosthetic heart valve is configured to be seated in an annulus of a native valve of the heart when in the expanded configuration. The distal anchoring element and the proximal anchoring element of the valve frame configured to be inserted through the annulus of the native valve prior to the prosthetic heart valve being seated therein. The proximal anchoring element is configured to be transitioned from a first configuration to a second configuration after the prosthetic valve is seated in the annulus of the native valve.

In some embodiments, a prosthetic heart valve includes a valve frame having a transannular section and an atrial collar attached around a top edge of the transannular section, a distal anchoring element coupled to the transannular section, a proximal anchoring element coupled to the transannular section, and a flow control component mounted within the valve frame. The flow control component is configured to permit blood flow in a first direction through an inflow end of the prosthetic heart valve and block blood flow in a second direction, opposite the first direction, through an outflow end of the prosthetic heart valve. The prosthetic heart valve has a compressed configuration for introduction into a heart of a patient via a delivery catheter and an expanded configuration when the prosthetic heart valve is released from the delivery catheter within an atrium of the heart. The prosthetic heart valve is configured to be seated in an annulus of a native valve of the heart when in the expanded configuration. The distal anchoring element is configured to be disposed in a ventricular outflow tract when the prosthetic heart valve is seated in the annulus of the native valve and the proximal anchoring element is configured to be transitioned from a first configuration to a second configuration after the prosthetic heart valve is seated in the annulus of the native valve.

In some embodiments, a method of delivering a prosthetic heart valve to an annulus of a native valve between an atrium and a ventricle of a heart of a patient includes disposing adjacent to the annulus of the native valve a distal end of a delivery catheter having disposed in a lumen thereof the prosthetic heart valve. The prosthetic heart valve includes a valve frame with a distal anchoring element and a proximal anchoring element, and a flow control component mounted within the valve frame. The prosthetic heart valve is in a compressed configuration within the lumen of the delivery catheter. The prosthetic heart valve is released from the lumen of the delivery catheter. The prosthetic heart valve is configured to transition from the compressed configuration to an expanded configuration in response to being released. A portion of the distal anchoring element is placed on the ventricle side of the annulus of the native valve. The prosthetic heart valve is seated in the annulus when the proximal anchoring element is in a first configuration and the proximal anchoring element is transitioned from the first configuration to a second configuration after the prosthetic heart valve is seated in the annulus.

In some embodiments, the invention comprises a side delivered transcatheter prosthetic heart valve having a distal anchoring tab and a proximal anchoring tab, having: (i) a self-expanding annular support frame, said annular support frame having a central channel and an outer perimeter wall circumscribing a central vertical axis in an expanded configuration, said annular support frame having a distal side and a proximal side; (ii) a flow control component mounted within the annular support frame and configured to permit blood flow in a first direction through an inflow end of the valve and block blood flow in a second direction, opposite the first direction, through an outflow end of the valve; (iii) a distal anchoring tab mounted on the distal side of the annular support frame; (iv) a proximal anchoring tab mounted on the proximal side of the annular support frame; wherein the valve is compressible to a compressed configuration for introduction into the body using a delivery catheter for implanting at a desired location in the body, said compressed configuration is oriented along a horizontal axis at an intersecting angle of between 45-135 degrees to the central vertical axis, and expandable to an expanded configuration having a horizontal axis at an intersecting angle of between 45-135 degrees to the central vertical axis; wherein the horizontal axis of the compressed configuration of the valve is substantially parallel to a length-wise cylindrical axis of the delivery catheter; wherein the valve has a height of about 5-60 mm and a diameter of about 25-80 mm.

In some embodiments, the proximal tab is fixed or unitary with the outer support frame. In other embodiments, the proximal tab is moveable from a first stowed position, i.e. held against the outer perimeter wall while the valve is positioned in the native annulus, and moveable to a second deployed position that extends away from the outer perimeter wall to provide a subannular anchor.

In some embodiments, the valve has a lower distal tab and a lower proximal tab. In other embodiments, the valve has a lower distal tab, a lower proximal tab, and an upper distal anchoring tab attached to a distal upper edge of the annular support frame, which may be comprised of wire loop, a wire frame, a laser cut frame, an integrated frame section, or a stent, and may extends from about 2-20 mm away from the annular support frame.

In some embodiments, the annular support frame is comprised of compressible wire cells selected from the group consisting of braided-wire cells, laser-cut wire cells, photolithography produced wire cells, 3D printed wire cells, wire cells formed from intermittently connected single strand wires in a wave shape, a zig-zag shape, or spiral shape, and combinations thereof.

In some embodiments, the invention provides a method for side delivery of an implantable prosthetic heart valve to a desired location in the body, the method comprising the step of advancing a delivery catheter to the desired location in the body and delivering an expandable prosthetic heart valve to the desired location in the body by releasing the valve from the delivery catheter, wherein the valve comprises an annular support frame having a flow control component mounted within the annular support frame and configured to permit blood flow in a first direction through an inflow end of the valve and block blood flow in a second direction, opposite the first direction, through an outflow end of the valve, a distal anchoring tab mounted on a distal side of the annular support frame, and a proximal anchoring tab mounted on a proximal side of the annular support frame, wherein the valve is compressible to a compressed configuration for introduction into the body using a delivery catheter for implanting at a desired location in the body, wherein the valve is compressible to a compressed configuration for introduction into the body using a delivery catheter for implanting at a desired location in the body, said compressed configuration has a height of 8-12 mm, a width of 8-12 mm, and a length of 25-80 mm, and wherein the horizontal axis of the compressed configuration of the valve is substantially parallel to a length-wise cylindrical axis of the delivery catheter, said expanded configuration has a height of about 5-60 mm and a diameter of about 25-80 mm.

In some embodiments, the said compressed configuration has a long-axis oriented at an intersecting angle of between 45-135 degrees to the first direction, and expandable to an expanded configuration having a long-axis oriented at an intersecting angle of between 45-135 degrees to the first direction, wherein the long-axis of the compressed configuration of the valve is substantially parallel to a length-wise cylindrical axis of the delivery catheter.

In some embodiments, the method includes a step wherein releasing the valve from the delivery catheter is selected from the steps consisting of: (i) pulling the valve out of the delivery catheter using a rigid elongated pushing rod/draw wire that is releasably connected to the distal side of the valve, wherein advancing the pushing rod away from the delivery catheter pulls the compressed valve out of the delivery catheter, or (ii) pushing the valve out of the delivery catheter using a rigid elongated pushing rod that is releasably connected to the proximal side of the valve, wherein advancing the pushing rod out of from the delivery catheter pushes the compressed valve out of the delivery catheter.

In some embodiments, the method comprises the additional step of anchoring one or more tissue anchors attached to the valve into native tissue.

In some embodiments, the method comprises the additional step of positioning the distal anchoring tab of the heart valve prosthesis into the right ventricular outflow tract of the right ventricle.

In some embodiments, the method comprises the additional steps of positioning the distal anchoring tab of the heart valve prosthesis into the right ventricular outflow tract of the right ventricle, and positioning an upper distal anchoring tab into a supra-annular position, and the upper distal anchoring tab providing a supra-annular downward force in the direction of the ventricle and distal anchoring tab providing a sub-annular upward force in the direction of the atrium.

In some embodiments, the method comprises the additional step of rotating the heart valve prosthesis using a steerable catheter along an axis parallel to the plane of the valve annulus.

In some embodiments, the invention provides a method for side delivery of implantable prosthetic heart valve in the body, the method comprising the steps: (i) advancing a distal end of a guide wire to a distal location, wherein the distal location is a pulmonary artery or a left ventricle of a heart, wherein the guide wire starts outside of a patient using femoral vein access or brachiocephalic vein access, and extends through an inferior vena cava or a superior vena cava to a right atrium, and extends from the right atrium through the tricuspid valve to the pulmonary artery or extends from the right atrium across the atrial septum in a transseptal access through the mitral valve and into a left ventricle; (ii) advancing a delivery catheter over the guide wire to a target location, where the target location is a right atrium of the tricuspid valve or a left atrium of the mitral valve; (iii) advancing and delivering an orthogonally compressed self-expandable prosthetic heart valve to the target location in the body, wherein a compressed configuration of the valve has a long-axis substantially parallel to a lengthwise cylindrical axis of the delivery catheter, wherein the expanded configuration of the valve has a height of about 5-60 mm and a diameter of about 25-80 mm, wherein the valve comprises an annular support frame having a flow control component mounted within the annular support frame and configured to permit blood flow in a first direction through an inflow end of the valve and block blood flow in a second direction, opposite the first direction, through an outflow end of the valve, a distal anchoring tab is mounted on a distal side of the annular support frame, the distal anchoring tab having a length of 10-40 mm and a width of 2-10 mm, wherein the guide wire is threaded through a threading aperture on or within the distal anchoring tab, at least one proximal anchoring tab is mounted on a proximal side of the annular support frame, the proximal anchoring tab having a length of 2-25 mm and a width of 2-10 mm, and a valve advancing tool comprising an elongated sheath wherein the guide wire is within a lumen of the sheath, wherein the outer diameter of the sheath is larger than the inner diameter of the threading aperture on the distal anchoring tab, wherein when the sheath is advanced over the guide wire in a distal direction, and a distal end of the sheath contacts a proximal surface of the threading aperture, the valve is advanced distally through the delivery catheter by the distally-directed pulling force that the sheath imparts to the distal anchoring tab; (iv) partially releasing the valve from the delivery catheter by advancing the sheath over the guide wire, and positioning the distal anchoring tab at a desired anchoring area of the target location, wherein the desired anchoring area is selected from a right ventricular outflow tract (RVOT) of a right ventricle, and a sub-annular area below an A1-P1 antero-lateral commissure of a mitral valve, wherein positioning the distal anchoring tab holds the valve at a raised angle of at least 30 degrees to a localized annular plane relative to the horizontal axis of the valve and the delivery catheter, wherein partially releasing the valve permits blood to flow partially around the prosthetic valve and through the native leaflets, and partially through the flow control component of the prosthetic valve to provide a gradual blood flow transition from flow through native leaflets to complete flow through the prosthetic valve; (v) completing release of the entire valve from the delivery catheter by advancing the sheath over the guide wire, seating the valve in the native annulus by applying a downward force in the direction of the ventricle; and (vi) seating the at least one proximal anchoring tab at a second desired anchoring area.

In some embodiments, the method comprises the additional step of anchoring one or more tissue anchors attached to the valve into native tissue.

In some embodiments, the invention provides a method for delivering a prosthetic heart valve to an annulus of a native valve between a ventricle and an atrium of a heart, the method comprising the steps: (i) disposing in the atrium of the heart a distal portion of a delivery catheter having a lumen and a longitudinal axis, with a distal end of the delivery catheter directed towards the annulus of the native valve, the distal portion of the delivery catheter having disposed within the lumen thereof the prosthetic heart valve in a compressed configuration, wherein the compressed configuration of the prosthetic heart valve has a long-axis substantially parallel to a length-wise cylindrical axis of the delivery catheter, wherein the expanded configuration of the prosthetic heart valve has a height of about 5-60 mm and a diameter of about 25-80 mm, wherein the prosthetic heart valve comprises an annular support frame having a flow control component mounted within the annular support frame and configured to permit blood flow in a first direction through an inflow end of the valve and block blood flow in a second direction, opposite the first direction, through an outflow end of the valve, wherein the annular support frame is self-expanding or balloon-expandable, a distal anchoring tab is mounted on a distal side of the annular support frame, the distal anchoring tab having a length of 10-40 mm, the distal anchoring tab extending laterally from the annular support frame and is configured to be disposed on a ventricle side of the annulus of the native valve when the annular support frame is disposed within the annulus, at least one proximal anchoring tab is mounted on a proximal side of the annular support frame, the proximal anchoring tab having a length of 2-25 mm, the at least one proximal anchoring tab extending laterally from the annular support frame and is configured to be disposed on the ventricle side of the annulus of the native valve when the annular support frame is disposed within the annulus; (ii) partially releasing the prosthetic heart valve from the delivery catheter, and positioning the distal anchoring tab at a distal subannular anchoring area, wherein the distal subannular anchoring area is a right ventricular outflow tract (RVOT) of a right ventricle or is a sub-annular area below an A1-P1 antero-lateral commissure of a mitral valve; (iii) completing release of the entire prosthetic heart valve from within the lumen of the delivery catheter, and seating the prosthetic heart valve in the native annulus by applying a downward force in the direction of the ventricle; and (iv) seating the proximal anchoring tab at a proximal subannular anchoring area.

In some embodiments, the method includes wherein positioning the distal anchoring tab holds the prosthetic heart valve at a raised angle of at least 30 degrees to a localized annular plane relative to a horizontal axis of the valve, and wherein partially releasing the prosthetic heart valve permits blood to flow partially around the prosthetic heart valve and through the native leaflets, and partially through the flow control component of the prosthetic valve to provide a gradual blood flow transition from flow through native leaflets to complete flow through the prosthetic valve.

In some embodiments, the method includes wherein seating the proximal anchoring tab comprises releasing the proximal anchoring tab from a compressed pre-release configuration to an expanded post-release configuration with the proximal anchoring tab extending into the proximal subannular anchoring area.

The terminology used herein is for the purpose of describing particular embodiments only and is not intended to limit the full scope of the claims. As used herein, the singular forms "a", "an" and "the" are intended to include the plural forms as well, unless the context clearly indicates otherwise. With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

In general, terms used herein, and especially in the appended claims (e.g., bodies of the appended claims) are generally intended as "open" terms (e.g., the term "including" should be interpreted as "including but not limited to," the term "having" should be interpreted as "having at least," etc.). Similarly, the terms "comprises" and/or "comprising," when used in this specification, specify the presence of stated features, integers (or fractions thereof), steps, operations, elements, and/or components, but do not preclude the presence or addition of one or more other features, integers (or fractions thereof), steps, operations, elements, components, and/or groups thereof. As used in this document, the term "comprising" means "including, but not limited to."

As used herein the term "and/or" or the phrase "selected from" or the phrase "selected from the group consisting of" or the phrase "selected from one or more of" includes any and all combinations of one or more of the associated listed items. It should be understood that virtually any disjunctive word and/or phrase presenting two or more alternative terms, whether in the description, claims, or drawings, should be understood to contemplate the possibilities of including one of the terms, either of the terms, or both/all terms. For example, the phrase "A or B" will be understood to include the possibilities of "A" or "B" or "A and B," and the phrase "selected from A, B, and C" will be understood to include the possibilities of "A", "B", "C", "A and B", "B and C", "A and C", and "A and B and C".

All ranges disclosed herein also encompass any and all possible subranges and combinations of subranges thereof unless expressly stated otherwise. Any listed range should be recognized as sufficiently describing and enabling the same range being broken down into at least equal subparts unless expressly stated otherwise. As will be understood by one skilled in the art, a range includes each individual member.

Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention.

The term "valve prosthesis," "prosthetic heart valve," and/or "prosthetic valve" can refer to a combination of a frame and a leaflet or flow control structure or component, and can encompass both complete replacement of an anatomical part (e.g., a new mechanical valve replaces a native valve), as well as medical devices that take the place of and/or assist, repair, or improve existing anatomical parts (e.g., the native valve is left in place).

The disclosed valves include a member (e.g., a frame) that can be seated within a native valve annulus and can be used as a mounting element for a leaflet structure, a flow control component, or a flexible reciprocating sleeve or sleeve-valve. It may or may not include such a leaflet structure or flow control component, depending on the embodiment. Such members can be referred to herein as an "annular support frame," "tubular frame," "wire frame," "valve frame," "flange," "collar," and/or any other similar terms.

The term "flow control component" can refer in a non-limiting sense to a leaflet structure having 2-, 3-, 4-leaflets of flexible biocompatible material such a treated or untreated pericardium that is sewn or joined to a annular support frame, to function as a prosthetic heart valve. Such a valve can be a heart valve, such as a tricuspid, mitral, aortic, or pulmonary, that is open to blood flowing during diastole from atrium to ventricle, and that closes from systolic ventricular pressure applied to the outer surface. Repeated opening and closing in sequence can be described as "reciprocating." The flow control component is contemplated to include a wide variety of (bio)prosthetic artificial heart valves, including ball valves (e.g., Starr-Edwards), bileaflet valves (St. Jude), tilting disc valves (e.g., Bjork-Shiley), stented pericardium heart-valve prosthesis' (bovine, porcine, ovine) (Edwards line of bioprostheses, St. Jude prosthetic valves), as well as homograft and autograft valves. Bioprosthetic pericardial valves can include bioprosthetic aortic valves, bioprosthetic mitral valves, bioprosthetic tricuspid valves, and bioprosthetic pulmonary valves.

Any of the disclosed valve embodiments may be delivered by a transcatheter approach. The term "transcatheter" is used to define the process of accessing, controlling, and/or delivering a medical device or instrument within the lumen of a catheter that is deployed into a heart chamber (or other desired location in the body), as well as an item that has been delivered or controlled by such as process. Transcatheter access is known to include cardiac access via the lumen of the femoral artery and/or vein, via the lumen of the brachial artery and/or vein, via lumen of the carotid artery, via the lumen of the jugular vein, via the intercostal (rib) and/or sub-xiphoid space, and/or the like. Transcatheter can be synonymous with transluminal and is functionally related to the term "percutaneous" as it relates to delivery of heart valves. As used herein, the term "lumen" can refer to the inside of a cylinder or tube. The term "bore" can refer to the inner diameter of the lumen.

The mode of cardiac access can be based at least in part on "body channel" may be used to define a blood conduit or vessel within the body, the particular application of the disclosed embodiments of prosthetic valves determines the body channel at issue. An aortic valve replacement, for example, would be implanted in, or adjacent to, the aortic annulus. Likewise, a tricuspid or mitral valve replacement would be implanted at the tricuspid or mitral annulus. Certain features are particularly advantageous for one implantation site or the other. However, unless the combination is structurally impossible, or excluded by claim language, any of the valve embodiments described herein could be implanted in any body channel.

The term "expandable" as used herein may refer to a component of the heart valve capable of expanding from a first, delivery diameter to a second, implantation diameter. An expandable structure, therefore, does not mean one that might undergo slight expansion from a rise in temperature, or other such incidental cause. Conversely, "non-expandable" should not be interpreted to mean completely rigid or a dimensionally stable, as some slight expansion of conventional "non-expandable" heart valves, for example, may be observed.

Any of the disclosed valve embodiments may be delivered via traditional transcatheter delivery techniques or via orthogonal delivery techniques. For example, traditional delivery of prosthetic valves can be such that a central cylinder axis of the valve is substantially parallel to a length-wise axis of the delivery catheter. Typically, the valves are compressed in a radial direction relative to the central cylinder axis and advanced through the lumen of the delivery catheter. The valves are deployed from the end of the delivery catheter and expanded outwardly in a radial direction from the central cylinder axis.

Side or orthogonal delivery of prosthetic valves can be such that the central cylinder axis of the valve is substantially orthogonal to the length-wise axis of the delivery catheter. With orthogonal delivery, the valves are compressed (or otherwise reduced in size) in a direction substantially parallel to the central cylinder axis and/or in a lateral direction relative to the central cylinder axis. As such, a length-wise axis of an orthogonally delivered valve is substantially parallel to the length-wise axis of the delivery catheter. In other words, an orthogonally delivered prosthetic valve is compressed and/or delivered at a roughly 90 degree angle compared to traditional processes of compressing and delivering transcatheter prosthetic valves. Moreover, prosthetic valves configured to be orthogonally delivered and the processes of delivering such valves are described in detail in the '957 PCT incorporated by reference hereinabove. As used herein the terms "side-delivered," "side-delivery," "orthogonal delivery," "orthogonally delivered," and/or so forth can be used interchangeably to such a delivery method and/or a valve delivered using such a method.

Mathematically, the term "orthogonal" refers to an intersecting angle of 90 degrees between two lines or planes. As used herein, the term "substantially orthogonal" refers to an intersecting angle of 90 degrees plus or minus a suitable tolerance. For example, "substantially orthogonal" can refer to an intersecting angle ranging from 75 to 105 degrees.

In some embodiments, components may be fabricated from a synthetic material(s) such a polyurethane or polytetrafluoroethylene (PTFE). Where a thin, durable synthetic material is contemplated (e.g., for a covering) synthetic polymer materials such expanded PTFE or polyester may optionally be used. Other suitable materials may optionally include thermoplastic polycarbonate urethane, polyether urethane, segmented polyether urethane, silicone polyether urethane, polyetheretherketone (PEEK), silicone-polycarbonate urethane, polypropylene, polyethylene, low-density polyethylene, high-density polyethylene, and ultra-high molecular weight polyethylene. Additional biocompatible polymers may optionally include elastomers, polyolefins, polyethylene-glycols, polyethersulphones, polysulphones, polyvinylpyrrolidones, polyvinylchlorides, other fluoropolymers, polyesters, polyethylene-terephthalate (PET) (e.g., Dacron), Poly-L-lactic acids (PLLA), polyglycolic acid (PGA), poly(D, L-lactide/glycolide) copolymer (PDLA), silicone polyesters, polyamides (Nylon), PTFE, elongated PTFE, expanded PTFE, polyurethanes, siloxane polymers and/or oligomers, and/or polylactones, and block co-polymers using the same.

In some embodiments, a valve frame and/or components thereof may be fabricated from biocompatible metals, metal alloys, polymer coated metals, and/or the like. Suitable biocompatible metals and/or metal alloys can include stainless steel (e.g., 316 L stainless steel), cobalt chromium (Co—Cr) alloys, nickel-titanium alloys (e.g., Nitinol®), and/or the like. Suitable polymer coatings can include poly-ethylene vinyl acetate (PEVA), poly-butyl methacrylate (PBMA), translute Styrene Isoprene Butadiene (SIBS) copolymer, polylactic acid, polyester, polylactide, D-lactic polylactic acid (DLPLA), and/or the like.

Any of the valve frames and/or portions or components thereof can be internally or externally covered, partially or completely, with a biocompatible material such as pericardium. A valve frame may also be optionally externally covered, partially or completely, with a second biocompatible material such as polyester or Dacron®. Disclosed embodiments may use tissue, such as a biological tissue that is a chemically stabilized pericardial tissue of an animal, such as a cow (bovine pericardium), sheep (ovine pericardium), pig (porcine pericardium), or horse (equine pericardium). Preferably, the tissue is bovine pericardial tissue. Examples of suitable tissue include that used in the products Duraguard®, Peri-Guard®, and Vascu-Guard®, all products currently used in surgical procedures, and which are marketed as being harvested generally from cattle less than 30 months old.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein. Rather, these embodiments are provided so that this disclosure will be thorough and complete, and will fully convey the scope of the inventive concepts to those skilled in the art. Like numbers refer to like elements throughout.

Figure 1C:
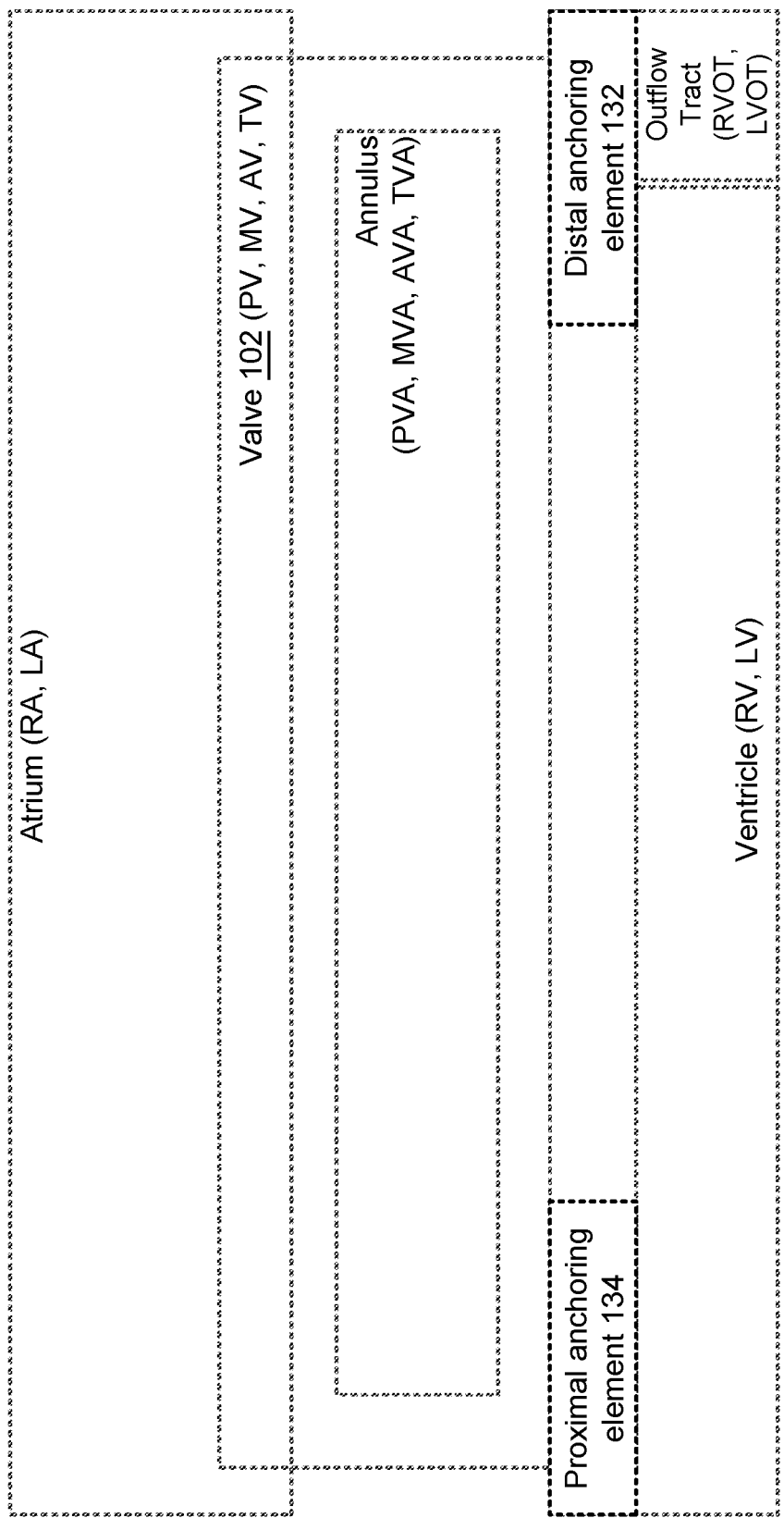

FIGS. 1A-1C are various schematic illustrations of a transcatheter prosthetic valve 102 according to an embodiment. The transcatheter prosthetic valve 102 is configured to deployed in a desired location within a body (e.g., of a human patient) and to permit blood flow in a first direction through an inflow end of the transcatheter prosthetic valve 102 and to block blood flow in a second direction, opposite the first direction, through an outflow end of the transcatheter prosthetic valve 102. For example, the transcatheter prosthetic valve 102 can be a transcatheter prosthetic heart valve configured to be deployed within the annulus of a native tricuspid valve or native mitral valve of a human heart to supplement and/or replace the functioning of the native valve.

The transcatheter prosthetic valve 102 (also referred to herein as "prosthetic valve" or simply "valve") is compressible and expandable in at least one direction relative to a long-axis 111 of the valve 102 (also referred to herein as "horizontal axis," "longitudinal axis," or "lengthwise axis"). The valve 102 is configured to compressible and expandable between an expanded configuration (FIGS. 1A and 1C) for implanting at a desired location in a body (e.g., a human heart) and a compressed configuration (FIG. 1B) for introduction into the body using a delivery catheter 172.

In some embodiments, the valve 102 can be centric, or radially symmetrical. In other embodiments, the valve 102 can be eccentric, or radially (y-axis) asymmetrical. In some eccentric embodiments, the valve 102 (or an outer frame thereof) may have a D-shape (viewed from the top) so the flat portion can be matched to the anatomy in which the valve 102 will be deployed. For example, in some instances, the valve 102 may be deployed in the tricuspid annulus and may have a complex shape determined by the anatomical structures where the valve 102 is being mounted. In the tricuspid annulus, the circumference of the tricuspid valve may be a rounded ellipse, the septal wall is known to be substantially vertical, and the tricuspid is known to enlarge in disease states along the anterior-posterior line. In other instances, the valve 102 may be deployed in the mitral annulus (e.g., near the anterior leaflet) and may have a complex shape determined by the anatomical structures where the valve 102 is being mounted. For example, in the mitral annulus, the circumference of the mitral valve may be a rounded ellipse, the septal wall is known to be substantially vertical, and the mitral is known to enlarge in disease states.

As shown, the valve 102 generally includes an annular support frame 110 and a flow control component 150. In addition, the valve 102 and/or at least the annular support frame 110 of the valve 102 includes one or more anchoring element. For example, in the embodiment shown in FIGS. 1A-1C, the annular support frame 110 includes at least a distal anchoring element 132 and a proximal anchoring element 134. In some implementations, the distal anchoring element 132 and the proximal anchoring element 134 can be lower anchoring elements and the valve 102 and/or the annular support frame 110 can include a distal upper anchoring element and a proximal upper anchoring element (not shown). In some implementations, the valve 102 and/or aspects or portions thereof can be similar to and/or substantially the same as the valves (and/or the corresponding aspects or portions thereof) described in detail in the '957 PCT incorporated by reference hereinabove. Accordingly, certain aspects, portions, and/or details of the valve 102 may not be described in further detail herein.

The annular support frame 110 (also referred to herein as "tubular frame," "valve frame," "wire frame," or "frame") can have or can define an aperture 114 that extends along a central axis 113. The aperture 114 (e.g., a central axial lumen) can be sized and configured to receive the flow control component 150 across a diameter of the aperture 114. The frame 110 may have an outer circumferential surface for engaging native annular tissue that may be tensioned against an inner aspect of the native annulus to provide structural patency to a weakened native annular ring.

The frame 110 includes a cuff or collar 120 and a tubular or transannular section 112. The cuff or collar 120 (referred to herein as "collar") can be attached to and/or can form an upper edge of the frame 110. When the valve 102 is deployed within a human heart, the collar 120 can be an atrial collar. The collar 120 can be shaped to conform to the native deployment location. In a mitral replacement, for example, the collar 120 will be configured with varying portions to conform to the native valve. In one embodiment, the collar 120 will have a distal and proximal upper collar portion. The distal collar portion can be larger than the proximal upper collar portion to account for annular geometries, supra-annular geometries, and/or subannular geometries.

The frame 110 may optionally have a separate atrial collar attached to the upper (atrial) edge of the frame 110, for deploying on the atrial floor that is used to direct blood from the atrium into the flow control component 150 and to seal against blood leakage (perivalvular leakage) around the frame 110. The frame 110 may also optionally have a separate ventricular collar attached to the lower (ventricular) edge of the frame 110, for deploying in the ventricle immediately below the native annulus that is used to prevent regurgitant leakage during systole, to prevent dislodging of the valve 102 during systole, to sandwich or compress the native annulus or adjacent tissue against the atrial collar or collar 120, and/or optionally to attach to and support the flow control component 150. Some embodiments may have both an atrial collar and a ventricular collar, whereas other embodiments either include a single atrial collar, a single ventricular collar, or have no additional collar structure.

The frame 110 can be a ring, or cylindrical or conical tube, but may also have a side profile of a flat-cone shape, an inverted flat-cone shape (narrower at top, wider at bottom), a concave cylinder (walls bent in), a convex cylinder (walls bulging out), an angular hourglass, a curved, graduated hourglass, a ring or cylinder having a flared top, flared bottom, or both. The frame 110 may have a height in the range of about 5-60 mm, may have an outer diameter dimension, R, in the range of about 20-80 mm, and may have an inner diameter dimension in the range of about 21-79 mm, accounting for the thickness of the frame 110 (e.g., a wire material forming the frame 110).

The frame 110 is compressible for delivery and when released it is configured to return to its original (uncompressed) shape. The frame 110 may be compressed for transcatheter delivery and may be expandable using a transcatheter expansion balloon. In other implementations, the frame 110 can include and/or can be formed of a shape-memory element allowing the frame 110 to be self-expanding. In some instances, suitable shape-memory materials can include metals and/or plastics that are durable and biocompatible. For example, the frame 110 can be made from super elastic metal wire, such as a Nitinol wire or other similarly functioning material. The frame 110 may be constructed as a braid, wire, or laser cut wire frame. The frame 110 may also have and/or form additional functional elements (e.g., loops, anchors, etc.) for attaching accessory components such as biocompatible covers, tissue anchors, releasable deployment and retrieval control guides, knobs, attachments, rigging, and so forth. In some implementations, the frame 110 (or aspects and/or portions thereof) can be structurally and/or functionally similar to the frames (or corresponding aspects and/or portions thereof) described in detail in the '957 PCT.

As described above, the frame 110 and/or the valve 102 can include at least a distal anchoring element 132 and a proximal anchoring element 134. The distal and proximal anchoring elements 132 and 134 can be, for example, lower anchoring elements (e.g., coupled to and/or included in a lower portion of the frame 110). In some embodiments, the frame 110 and/or the valve 102 can also optionally include one or more of a distal upper anchoring element and a proximal upper anchoring element. The anchoring elements of the valve 102 can be configured to engage a desired portion of the annular tissue to mount the frame 110 to the annulus of the native valve in which the valve 102 is deployed, as described in further detail herein. The anchoring elements of the valve 102 and/or the frame 110 can be any suitable shape, size, and/or configuration such as any of those described in detail in the '957 PCT. Moreover, certain aspects, features, and/or configurations of at least the distal and proximal anchoring elements 132 and 134 are described below reference to specific embodiments.

As shown in FIGS. 1A and 1B, the distal anchoring element 132 can include a guidewire collar 145 configured to selectively engage and/or receive a portion of a guidewire 185 or a portion of a guidewire assembly and/or can have any suitable configuration as described below with respect to specific embodiments. For example, in some embodiments, a portion of the guidewire 185 can extend through an aperture (not shown) of the guidewire collar 145, thereby allowing the valve 102 to be advanced over or along the guidewire 185. The guidewire collar 145 can be any suitable element that selectively allows the guidewire 185 to be advanced therethrough while blocking or preventing other elements and/or components such as a pusher or the like. In certain embodiments, the distal lower anchoring element 132 can form and/or can include a feature that forms the guidewire collar 145. In other implementations, the guidewire collar 145 can be attached to any suitable portion of the frame 110, to the proximal anchoring element 134, and/or to any other anchoring elements and/or features of the frame 110 (e.g., a distal or proximal upper anchoring element).

The proximal anchoring element 134 can be any suitable shape, size, and/or configuration such as any of those described herein with respect to specific embodiments. The proximal anchoring element 134 can be, for example, a proximal lower anchoring element and can be configured to engage subannular tissue of the ventricle to aid in the securement of the valve 102 in the annulus. In some implementations, the proximal anchoring element 134 can be configured to transition between a first configuration in which the proximal anchoring element 134 is maintained in a compressed, undeployed, and/or restrained state, to a second configuration in which the proximal anchoring element 134 is expanded, extended, deployed, and/or unrestrained. More specifically, the proximal anchoring element 134 when in the first configuration can be maintained in a first position that is in contact with, adjacent to, and/or otherwise near the transannular section 112 of the valve frame 110, and when in the second configuration, can be released to a second position that extends away from the transannular section 112 of the frame 110. Said another way, the second position proximal anchoring element 134 can be further from the transannular section 112 than the first position of the proximal anchoring element 134.

In some embodiments, the valve 102 and/or the frame 110 can include a feature, member, mechanism, etc. configured to at least temporarily retain the proximal anchoring element 134 in the first configuration. For example, as shown in FIGS. 1A and 1B, the valve 102 and/or the frame 110 can include a tensile member 135 configured to selectively engage the proximal anchoring element 134 to temporarily maintain the proximal anchoring element 134 in the first configuration. The tensile member 135 can be any suitable shape, size, and/or configuration. For example, the tensile member 135 can be an anchor, loop, tab, latch, hook, tether, elastomeric band, threaded coupler, ball and cup mechanism, and/or any other suitable removable attachment. The tensile member 135 can removably couple to a portion of the proximal anchoring element 134 and can exert a force (e.g., a tensile or compression force) operable in maintaining the proximal anchoring element 134 in the first configuration. The tensile member 135 can be reconfigurable allowing the tensile member 135 to be disengaged from the proximal anchoring element 134, which in turn, can allow the proximal anchoring element 134 to transition from its first configuration to its second configuration, as described in further detail herein with reference to specific embodiments.

The valve 102 can be delivered to the desired location in the body via a procedure generally including advancing a delivery catheter 172 over the guide wire 185 to place a distal end of the delivery catheter 172 at or near the desired location. The guidewire 185, therefore, may be disposed within a lumen 174 of the delivery catheter 172. The valve 102 can be disposed within the lumen 174 of the delivery catheter 172 (e.g., in the compressed configuration) such that the guidewire collar 145 is engaged with and/or receives a portion of the guidewire 185, thereby allowing the valve 102 to be advanced over and/or along the guidewire 185 through the delivery catheter 172.

The flow control component 150 can refer in a non-limiting sense to a device for controlling fluid flow therethrough. In some embodiments, the flow control component 150 can be a leaflet structure having 2-leaflets, 3-leaflets, 4-leaflets, or more, made of flexible biocompatible material such a treated or untreated pericardium. The leaflets can be sewn or joined to a support structure and/or can be sewn or joined to the frame 110. The flow control component 150 can be mounted within the frame 110 and configured to permit blood flow in a first direction through an inflow end of the valve and block blood flow in a second direction, opposite the first direction, through an outflow end of the valve. For example, the flow control component 150 can be configured such that the valve 102 functions, for example, as a heart valve, such as a tricuspid valve, mitral valve, aortic valve, or pulmonary valve, that can open to blood flowing during diastole from atrium to ventricle, and that can close from systolic ventricular pressure applied to the outer surface. Repeated opening and closing in sequence can be described as "reciprocating."

The flow control component 150 is contemplated to include a wide variety of (bio)prosthetic artificial valves, including ball valves (e.g., Starr-Edwards), bileaflet valves (St. Jude), tilting disc valves (e.g., Bjork-Shiley), stented pericardium heart-valve prosthesis' (bovine, porcine, ovine) (Edwards line of bioprostheses, St. Jude prosthetic valves), as well as homograft and autograft valves. Bioprosthetic pericardial valves can include bioprosthetic aortic valves, bioprosthetic mitral valves, bioprosthetic tricuspid valves, and bioprosthetic pulmonary valves. In some implementations, a suitable commercially available valve (flow control component 150) can be received or accepted by and/or otherwise mounted in the frame 110. Commercially available valves (flow control components 150) may include, for example, a Sapien, Sapien 3, or Sapien XT from Edwards Lifesciences, an Inspiris Resilia aortic valve from Edwards Lifesciences, a Masters HP 15 mm valve from Abbott, a Lotus Edge valve from Boston Scientific, a Crown PRT leaflet structure from Livanova/Sorin, a valve from the Carbomedics family of valves from Sorin, or other flow control component(s), or a flexible reciprocating sleeve or sleeve-valve. In some implementations, the flow control component 150 can be similar to or substantially the same as any of the flow control components described in detail in the '957 PCT.

The valve 102 is compressible and expandable between the expanded configuration and the compressed configuration. The valve 102 is compressed during delivery of the valve 102 and is configured to expand once released from the deliver catheter 172. The valve 102 is in the expanded configuration when deployed or implanted (or ready to be deployed or implanted) at the desired location in the body. When in the expanded configuration shown in FIGS. 1A and 1B, the valve 102 has an extent in any direction along or lateral to the central axis 113 that is larger than a diameter of the lumen 174 of the delivery catheter 172 used to deliver the valve 102. Said another way, the valve 102 has an extent in any direction perpendicular to the longitudinal axis 111 of the valve 102 that is larger than the diameter of the lumen 174 of the delivery catheter 172.

In some embodiments, the valve 102 can have an expanded height (y-axis) of 5-60 mm. In some embodiments, the valve 102 can have an expanded diameter length and width of about 20-80 mm and more particularly, 40-80 mm. In certain embodiments, the valve 102 can have a length and/or width including, for example, 20 mm, 25 mm, 30 mm, 35 mm, 40 mm, 45 mm, 50 mm, 55 mm, 60 mm, 65 mm, 70 mm, 75 mm, and 80 mm, and/or any size or fraction of a size therebetween.

The valve 102 is in the compressed configuration when being delivered to the desired location in the body via the delivery catheter 172. When in the compressed configuration, the valve 102 can have a size that allows the valve 102 to be disposed within the lumen 174 of the delivery catheter 172. In some implementations, the valve 102 is configured for transcatheter orthogonal delivery to the desired location in the body (e.g., the annulus of a native valve), in which the valve 102 is compressed in a lateral direction relative to the dimensions of the valve 102 in the expanded configuration (e.g., along the central axis 113) and can be elongated in a longitudinal direction (e.g., along the longitudinal axis 111). In other implementations, the valve 102 is configured to traditional transcatheter delivery to the desired location in the body, in which the central axis 113 is coaxial with the longitudinal axis 111. Aspects, features, and/or processes of traditional transcatheter delivery are not described in further detail herein.

During delivery, the longitudinal axis 111 of the valve 102 is substantially parallel to a longitudinal axis 175 of the delivery catheter 172. In orthogonal delivery, the longitudinal axis 111 is oriented at an intersecting angle between 45 and 135 degrees relative to the central axis 113 (e.g., perpendicular or at about 90 degrees). In some embodiments, the horizontal x-axis (e.g., the longitudinal axis 111) of the valve 102 is orthogonal or substantially orthogonal to (e.g., 75-105 degrees), or substantially oblique to (45-135 degrees) the central vertical y-axis (e.g., the central axis 113) when in an expanded configuration. In some embodiments, the horizontal x-axis (e.g., the longitudinal axis 111) of the valve 102 in the compressed configuration is substantially parallel to a lengthwise cylindrical axis 175 of the delivery catheter 172.

As used herein, the terms "intersecting angle" and/or "orthogonal angle" can refer to both (i) the relationship between the lengthwise cylindrical axis (e.g., the longitudinal axis 175) of the delivery catheter 174 and the long-axis 111 of the compressed valve 102, where the long-axis 111 is perpendicular to the central axis 113 of traditional valves, and (ii) the relationship between the long-axis 111 of the compressed or expanded valve 102 and the axis defined by the blood flow through the prosthetic valve 102 where the blood is flowing (e.g., from one part of the body or chamber of the heart to another downstream part of the body or chamber of the heart, such as from an atrium to a ventricle through a native annulus).

The valve 102 can have a first height or size along the central axis 113 when in the expanded configuration and can have a second height or size, less than the first height or size, along the central axis 113 when in the compressed configuration. The second height or size of the valve 102 when in the compressed configuration is smaller than the diameter of the lumen 174 of the delivery catheter 175, allowing the valve 102 to be delivered therethrough. The valve 102 can also be compressed in additional directions. For example, the valve 102 can be compressed along a lateral axis (not shown) that is perpendicular to both the longitudinal axis 111 and the central axis 113. The valve 102, when in the expanded configuration, has an extent in any direction along or parallel to the lateral axis that is larger than a diameter of the lumen 174 of the delivery catheter 172. In other words, the valve 102 can have a first width or size along the lateral axis when in the expanded configuration and can have a second width or size, less than the first width or size, along the lateral axis when in the compressed configuration, as described in detail in the '957 PCT.

The valve 102 may be compressed (as described above) and delivered in a sideways or orthogonal manner such that the longitudinal axis 111 is substantially parallel to a delivery axis (e.g., the lengthwise axis 175 of the delivery catheter 172). The shape of the expanded valve 102 can be that of a large diameter shortened cylinder with an extended collar (e.g., the collar 120). The valve 120 can be compressed, in some embodiments, where the central axis 113 of the valve 102 is roughly perpendicular to (orthogonal to) the lengthwise axis 175 of the delivery catheter 172. In some embodiments, the valve 102 can be compressed vertically (e.g., along the central axis 113) and/or can be compressed laterally (e.g., along the lateral axis, not shown). In some embodiments, the valve 102 can have a compressed height (y-axis) and/or width (z-axis) of about 6-15 mm, about 8-12 mm, or more particularly, 9-10 mm. In some embodiments, the length of the valve 102 (x-axis) does not require compression since it can extend along the length of the lumen 174 of the delivery catheter 172. In some embodiments, the length of the valve 102 (x-axis) is increased in response to compression of the height (y-axis) and/or width (z-axis). The valve 102 can be compressed by compressing, rolling, folding, and/or any other suitable manner, or combinations thereof, as described in detail in the '957 PCT.

In some implementations, a delivery system can include one or more features or components configured to deliver the valve 102 to a desired location in the body (e.g., the annulus of a native valve)—either via traditional delivery techniques or via orthogonal delivery techniques. For example, a delivery system 170 suitable for at least orthogonal delivery is shown in FIG. 1B. The delivery system 170 includes the delivery catheter 172, a secondary catheter 180, and the guidewire 185. The delivery system 170 can be configured to orthogonally deliver the compressed valve 102 and/or portions of the valve 102 (e.g., the compressed frame 110 or the compressed flow control component 150) to a desired location in the body such as, for example, the annulus of a native tricuspid valve and/or the annulus of a native mitral valve of the human heart. For example, the delivery catheter 172 can be 12-34 Fr, with any suitable corresponding internal lumen diameter and/or an internal lumen diameter sufficient to receive the prosthetic valve 102 in the compressed configuration. In some implementations, the delivery system 170 and/or aspects or portions thereof can be similar to and/or substantially the same as those described in detail in the '957 PCT.

The guidewire 185 extends or threads through the secondary catheter 180, the guidewire collar 145 of or connected to the distal anchoring element 132, and the delivery catheter 172. The guidewire 185 can be, for example, a sheathed guidewire at least partially sheathed by the secondary catheter 180. The guidewire 185 is configured to be advanced through the anatomy of the body and placed in a desired position relative to native tissue (e.g., a native valve). In some instances, the guidewire 185 can be advanced to provide a wire path (e.g., for the delivery catheter 172, the valve 102, the secondary catheter 180, etc.)

to the outflow tract of the ventricle (e.g., the RVOT or the LVOT depending on the native valve). The guidewire 185 extends through the guidewire collar 145 of the valve 102 to provide a wire path along which the valve 102 is advanced (e.g., through the delivery catheter 172 and/or at least a portion of the atrium or ventricle of the heart).

As shown in FIG. 1B, at least a portion of the secondary catheter 180 can be disposed in the lumen 174 of the delivery catheter 172. The secondary catheter 180 can be disposed over and/or advanced along the guidewire 185. The secondary catheter 180 can be a sheath, tube, annular rod or wire, and/or the like. In some embodiments, the secondary catheter 180 is a hypotube sheath disposed about a portion of the guidewire 185 (e.g., the secondary catheter 180 and the guidewire 185 collectively form a sheathed guidewire or sheathed guidewire assembly). The secondary catheter 180 can have a relatively small size allowing the secondary catheter 180 to be advanced through the delivery catheter 172 and/or at least partially disposed in or otherwise engaged with the guidewire collar 145. The secondary catheter 180 has a lumen with an internal diameter that is greater than the guidewire 185, allowing the guidewire 185 to pass therethrough.

The pusher 181 is also disposed within the secondary catheter 180 and is configured to push on a portion of the valve 102 to advance the valve 102 through and/or out of the delivery catheter 172. In some implementations, the pusher 181 is configured to push against a portion of the guidewire collar 145 and/or the distal anchoring element 132. For example, the guidewire collar 145 can allow the guidewire 185 to be advanced through the guidewire collar 145 and can block and/or substantially prevent the pusher 181 from being advanced beyond the guidewire collar 145 (or at least a portion thereof). The guidewire collar 145 can be and/or can include a feature that defines an aperture or lumen that is sufficiently large to allow the guidewire 185 to pass through but is not sufficiently large to allow other components to be advanced therethrough (e.g., the pusher 181). As such, the secondary catheter 180 and/or the pusher 181 can be stopped against the guidewire collar 145 by the larger circumference of the secondary catheter 180 and/or pusher 181 relative to the aperture or lumen of the guidewire collar 145. Such an arrangement allows the secondary catheter 180 and/or pusher 181 to push on the guidewire collar 145 and thus, the distal anchoring element 132 to which it is attached. When the guidewire collar 145 is attached to the distal anchoring element 132, the pushing on the guidewire collar 145 is operative to pull the valve 102 through and/or out of the delivery catheter 172.

While the pusher 181 is shown disposed in the secondary catheter 180, in some embodiments, the secondary catheter 180 can be used as the pusher 181. In such embodiments, the delivery system 170 need not include a separate pusher 181. Moreover, while the pusher 181 is described above as engaging, for example, the distal anchoring element 132, in other implementations, the pusher 181 can be configured to engage any suitable portion of the valve 102 such as the proximal anchoring element 134, and/or the like. Although not shown in FIGS. 1A-1C, the guidewire collar 145, the secondary catheter 180, and/or the pusher 181 can include a release mechanism or feature configured to release the guidewire 185, the secondary catheter 180, and/or the pusher 181 from the guidewire collar 145, for example, after deployment of the valve 102.

As shown in FIG. 1C, the valve 102 can be delivered, for example, to an atrium of the human heart and disposed within an annulus of a native valve such as, for example, the pulmonary valve (PV), the mitral valve (MV), the aortic valve (AV), and/or the tricuspid valve (TV). As described above, the valve 102 can be in the compressed configuration and delivered to the annulus via the delivery system 170—either via traditional delivery techniques or via orthogonal delivery techniques—and can be released from the delivery system 170 and allowed to expand to the expanded configuration. For example, the valve 102 can be delivered to the atrium of the human heart and released from the delivery catheter 172 via any of the delivery systems, devices, and/or methods described in detail in the '957 PCT.

The deployment of the valve 102 can include placing the distal anchoring element 132 (e.g., the distal lower anchoring element 132) in the ventricle (RV, LV) below the annulus while the remaining portions of the valve 102 are in the atrium (RA, LA). In some instances, the distal anchoring element 132 can be positioned in an outflow tract of the ventricle (e.g., the distal anchoring element 132 can be advanced over and/or along the guidewire 185). For example, in some implementations, the valve 102 can be delivered to the annulus of the native tricuspid valve (TV) and at least a portion of the distal anchoring element 132 can be positioned in a right ventricular outflow tract (RVOT). In other implementations, the valve 102 can be delivered to the annulus of the native mitral valve (MV) and at least a portion of the distal anchoring element 132 can be positioned in a left ventricular outflow tract (LVOT). In some instances, the distal anchoring element 134 can engage subannular tissue to at least partially secure the distal end portion of the valve 102 to the native annular tissue while the remainder of the valve 102 is maintained in a supra-annular position within the atrium side of the annulus.

In some implementations, the prosthetic valve 102 can be temporarily maintained in a partially deployed state. For example, the valve 102 can be partially inserted into the annulus and held at an angle relative to the annulus to allow blood to flow from the atrium to the ventricle partially through the native valve annulus around the valve 102, and partially through the valve 102, which can allow for assessment of the valve function.

The valve 102 can be placed or seated in the annulus (PVA, MVA, AVA, and/or TVA) of the native valve (PV, MV, AV, and/or TV) such that the transannular section 112 of the valve frame 110 extends through the annulus and into the ventricle while the collar remains in the atrium in a supra-annular position. For example, in some embodiments, the secondary catheter 180 and/or the pusher 181 can be used to push at least the proximal end portion of the valve 102 into the annulus. In some implementations, the proximal anchoring element 134 can be maintained in its first configuration as the valve 102 is seated in the annulus. For example, as described above, the proximal anchoring element 134 can be in contact with, adjacent to, and/or near the transannular section 112 of the frame 110 while in the first configuration, which in turn, can limit an overall circumference of a lower portion of the frame 110, thereby allowing the transannular section 112 of the frame 110 to be inserted through the annulus.

Once seated, the proximal anchoring element 134 can be transitioned from its first configuration to its second configuration. For example, in some implementations, a tensile force can be exerted on, along, and/or through the tensile member 135 that can be operable in maintaining the proximal anchoring element 134 in its first configuration. The tensile member 135 can be manipulated to disengage from the proximal anchoring element 135 thereby allowing the proximal anchoring element 134 to transition to its second configuration. In some implementations, the secondary catheter 180, the pusher 181, and/or any suitable member or feature of the delivery system 170 can be configured to disengage the tensile member 135 from the proximal anchoring element 134. In some implementations, a portion of the tensile member 135 can be actuated to disengage from the proximal anchoring element 134. Accordingly, once the valve 102 is seated in the annulus, the proximal anchoring element 134 can be placed in its second configuration in which the proximal anchoring element 134 contacts, engages, and/or is otherwise disposed adjacent to subannular tissue. Moreover, in some implementations, the distal anchoring element 132, the proximal anchoring element 134, and the collar 120 (or any other upper anchoring elements) can exert a compressive force on the annular tissue separating the atrium from the ventricle, thereby placing the valve 102 in a fully deployed state. While not shown in FIGS. 1A-1C, in some implementations, the valve 102 and/or the delivery system 170 can include one or more tissue anchors that can be used to anchor one or more portions of the valve 102 to the annular tissue, as described in detail in the '957 PCT.

Provided below is a discussion of certain aspects or embodiments of transcatheter prosthetic valves (e.g., prosthetic heart valves). The transcatheter prosthetic valves (or aspects or portions thereof) described below with respect to specific embodiments can be substantially similar in at least form and/or function to the valve 102 and/or corresponding aspects or portions of the valve 102 described above with reference to FIGS. 1A-1C. Similarly, the valves described below (or aspects or portions thereof) can be similar in at least form and/or function to the valves described in detail in the '957 PCT. Thus, certain aspects and/or portions of the specific embodiments may not described in further detail herein.

Figure 2:
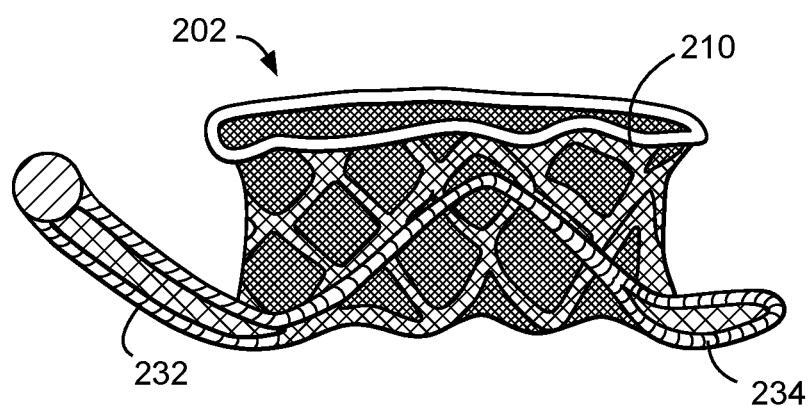
FIGS. 2-6 are side perspective view illustrations of transcatheter prosthetic valves having distal and proximal anchoring elements, each according to an embodiment.

FIG. 2 is an illustration of a side perspective view of a side delivered transcatheter prosthetic heart valve 202 according to an embodiment. The valve 202 and/or aspects or portions thereof can be substantially similar to the valve 102 shown in FIGS. 1A-1C. The valve 202 has a wire frame 210 that includes a distal anchoring element 232 and a proximal anchoring element 234. In the embodiment shown in FIG. 2, each of the distal anchoring element 232 and the proximal anchoring element 234 is formed of or from a superelastic wire loop (e.g., formed by Nitinol wire or the like).

Figure 3:
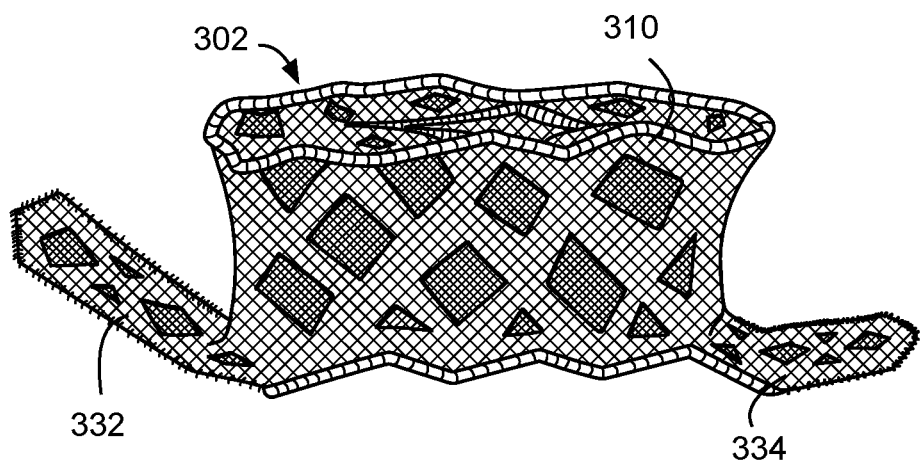

FIG. 3 is an illustration of a side perspective view of a side delivered transcatheter prosthetic heart valve 302 according to an embodiment. The valve 302 has a laser cut frame 310 with a laser cut distal anchoring element 332 and a laser cut proximal anchoring element 334.

Figure 4:
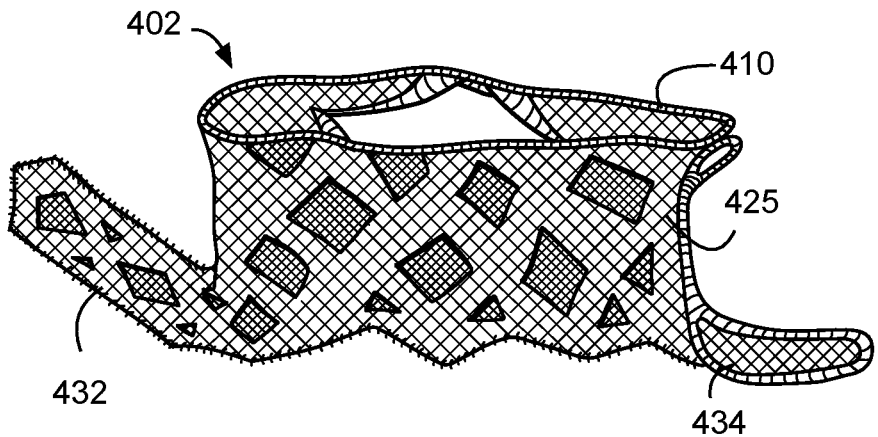

FIG. 4 is an illustration of a side perspective view of a side delivered transcatheter prosthetic heart valve 402 according to an embodiment. The valve 402 has a laser cut frame 410 with a laser cut distal anchoring element 432 and a superelastic wire loop proximal anchoring element 434.

Figure 5:
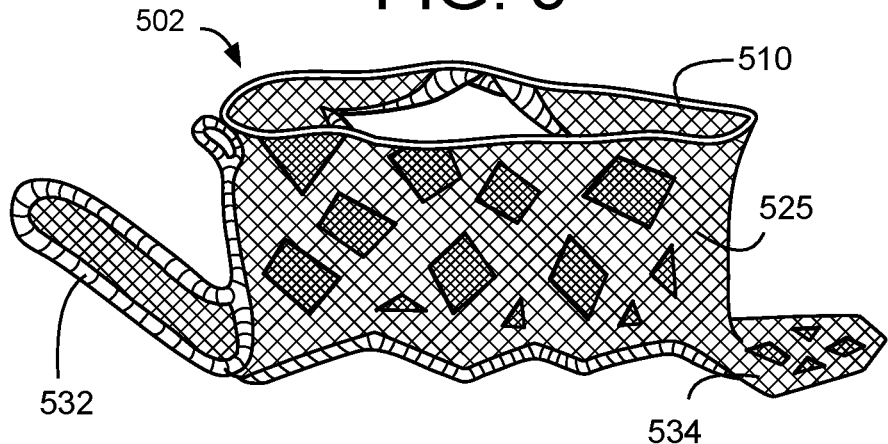

FIG. 5 is an illustration of a side perspective view of a side delivered transcatheter prosthetic heart valve 502 according to an embodiment. The valve 502 has a laser cut frame 510 with a superelastic wire loop distal anchoring element 532 and a laser cut proximal anchoring element 534.

Figure 6:
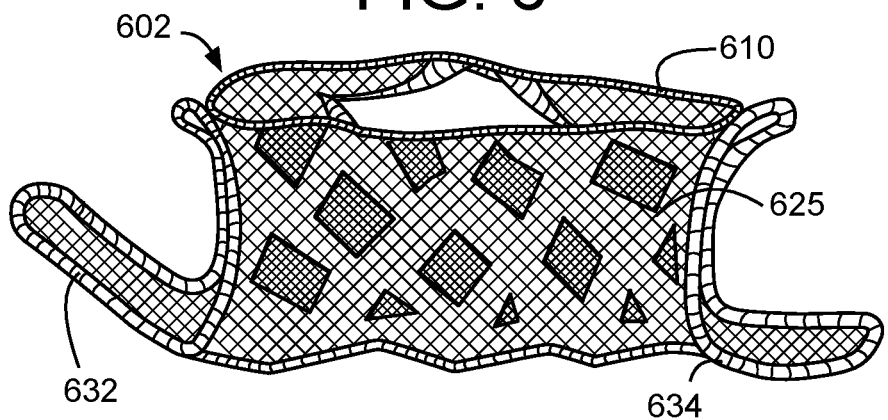

FIG. 6 is an illustration of a side perspective view of a side delivered transcatheter prosthetic heart valve 602 according to an embodiment. The valve 602 has a laser cut frame 610 with a superelastic wire loop distal anchoring element 632 and a superelastic wire loop proximal anchoring element 634.

Figure 7A:
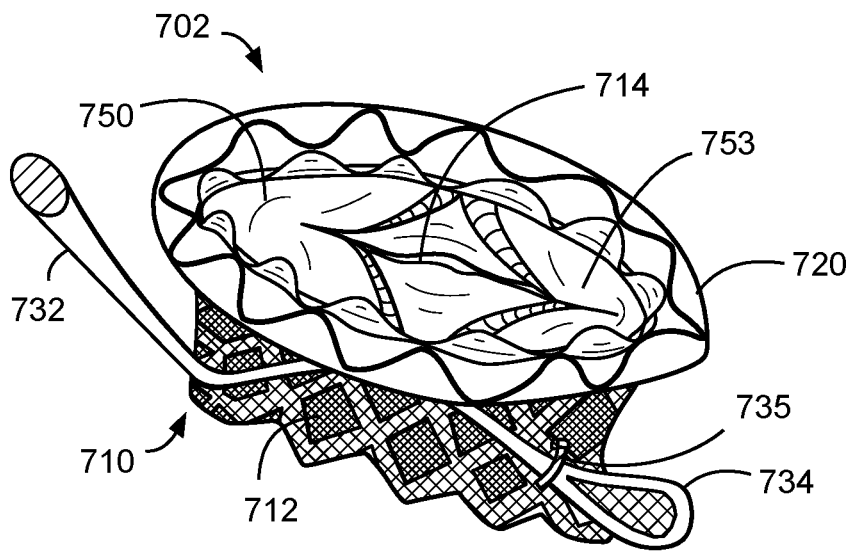
FIGS. 7A and 7B are perspective view illustrations of a transcatheter prosthetic valve having a distal and proximal anchoring element according to an embodiment, and shown in a pre-released, anchored configuration and a post-released, extended configuration, respectively.
Figure 7B:
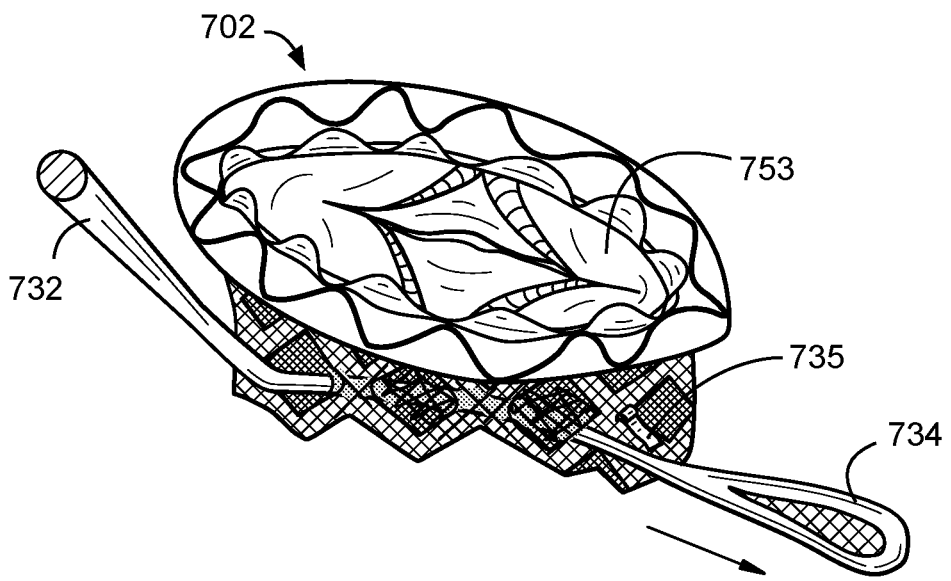

FIGS. 7A and 7B illustrate side perspective views of a side delivered transcatheter prosthetic heart valve 702 according to an embodiment. The valve 702 has a laser cut frame 710 with a superelastic wire loop distal anchoring element 732 and a superelastic wire loop proximal anchoring element 734. The valve 702 shown in FIG. 7A has a frame 710 and a flow control component 750. The frame 710 has a transannular section 712 and an atrial collar 720 disposed around and/or coupled to a top edge of the transannular section 712. The flow control component 750 is disposed within an aperture 714 of the frame 710. The flow control component 750 can have any number of prosthetic leaflets 753 (e.g., two, three, four, or more) mounted within the flow control component 750. The leaflets 753 can define a channel for blood flow in a single direction from an inflow side of the valve 702 to an outflow side of the valve 702.

FIG. 7A shows a tensile member 735 of the frame 710 and/or valve 702 in a first or initial state in which the tensile member 735 engages the proximal anchoring element 734 to maintain the proximal anchoring element 734 in its first configuration (e.g., a pre-release configuration). The proximal anchoring element 734 can be in its first configuration before and during deployment of the valve 702 and/or seating of the valve 702 in an annulus). FIG. 7B shows the tensile member 735 in a second state in which the tensile member 735 is disengaged from the proximal anchoring element 734. The proximal anchoring element 734 is allowed to transition from its first configuration to its second configuration, as indicated by the arrow in FIG. 7B. The proximal anchoring element 734 can be transitioned to the second configuration after the valve 702 is seated in the annulus.

Figure 8:
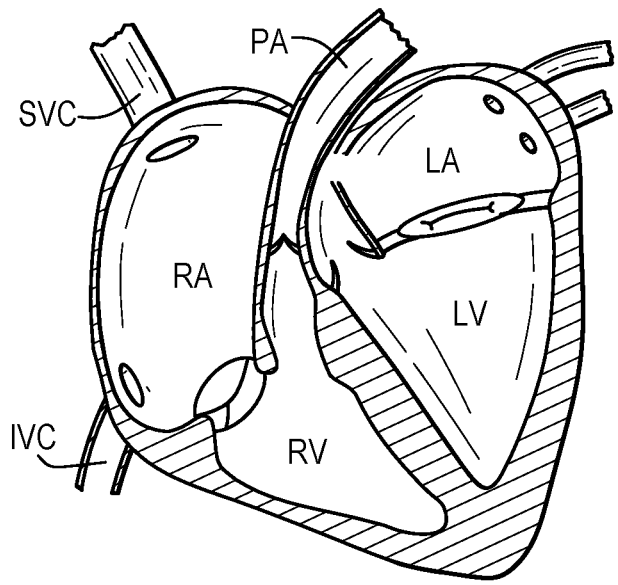
FIG. 8 is a cut-away side view illustration of the human heart anatomy.

FIG. 8 is an illustration of a side view of human heart anatomy, with an inset showing the geometric relationship between the inferior vena cava (IVC), superior vena cava (SVC), the right atrium (RA), the left atrium (LA), the right ventricle (RV), the left ventricle (LV), and the pulmonary artery (PA). A three leaflet tricuspid valve—having anterior, posterior, and septal cusps—is shown between the RA and the RV. A two leaflet mitral valve is shown between the LA and the LV.

Figure 9A:
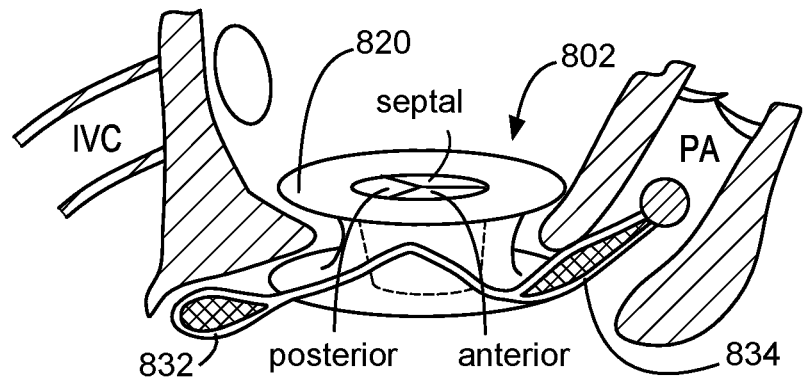
FIGS. 9A and 9B are an anterior side perspective view illustration and a septal side perspective view illustration, respectively, of a transcatheter prosthetic valve seated with the native tricuspid annulus of the human heart, according to embodiment.
Figure 9B:
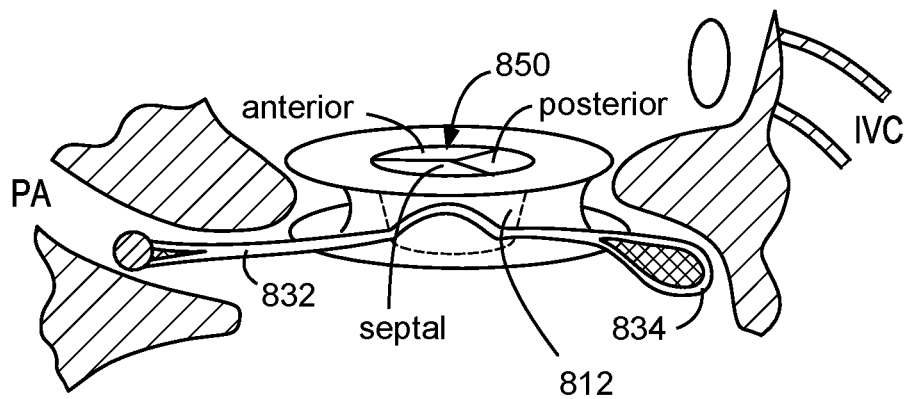

FIGS. 9A and 9B illustrate an anterior side perspective view and a posterior side perspective view, respectively, of a side delivered valve 802 seated with the native tricuspid annulus. A collar 820 of the valve 802 is laying atrially above the tricuspid annulus and leaflets, a transannular section 812 of the valve 802 extending into and through the annulus to provide corrective hemodynamic flow from the flow control component 850, a distal anchoring element 832 at least partially disposed in a right ventricular outflow tract (e.g., the pulmonary artery (PA)), and a proximal anchoring element 134 in a released configuration engaging subannular tissue.

Figure 10A:
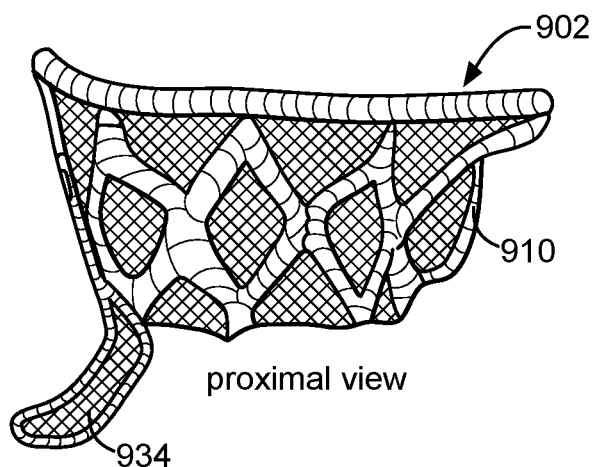
FIGS. 10A and 10B are a proximal side view illustration of a transcatheter prosthetic valve showing a proximal anchoring element thereof and a distal side view illustration of the valve showing a distal anchoring element thereof, according to an embodiment.
Figure 10B:
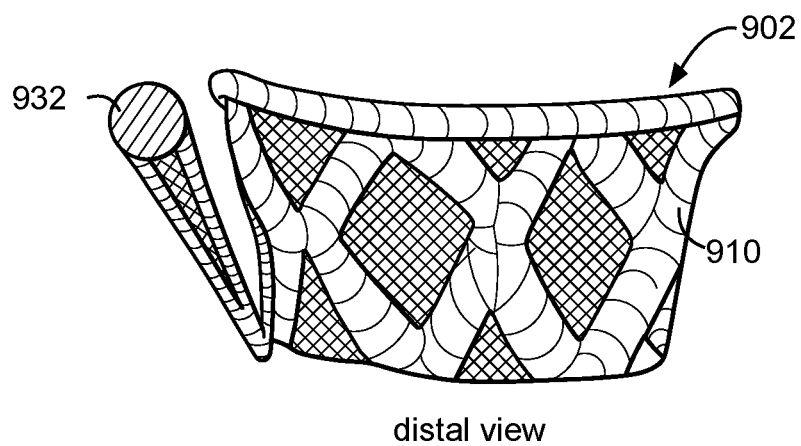

FIGS. 10A and 10B illustrate side perspective views of a side delivered transcatheter prosthetic heart valve 902 according to an embodiment. FIG. 10A is a proximal side perspective view of the valve 902 and shows a proximal anchoring element 934 extending away from a wire frame 910. FIG. 10B is a distal side perspective view of the valve 902 and shows a distal anchoring element 932 extending away from the wire frame 910.

Figure 11A:
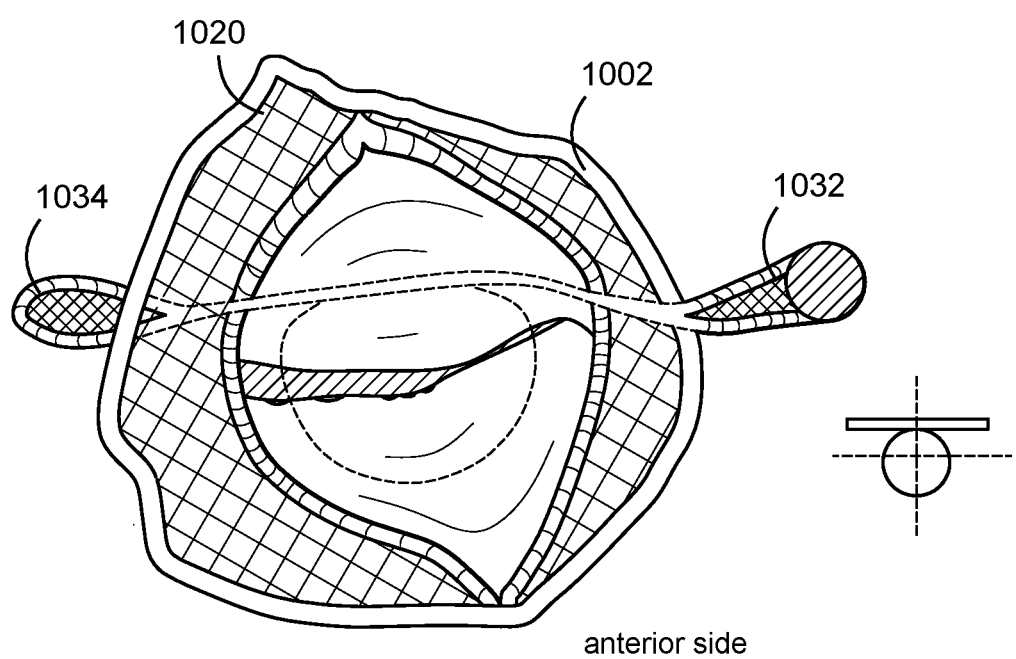
FIGS. 11A and 11B are a top anterior view illustration and a top septal view illustration, respectively, of a transcatheter prosthetic valve having a dual anchoring element mechanism according to an embodiment.
Figure 11B:
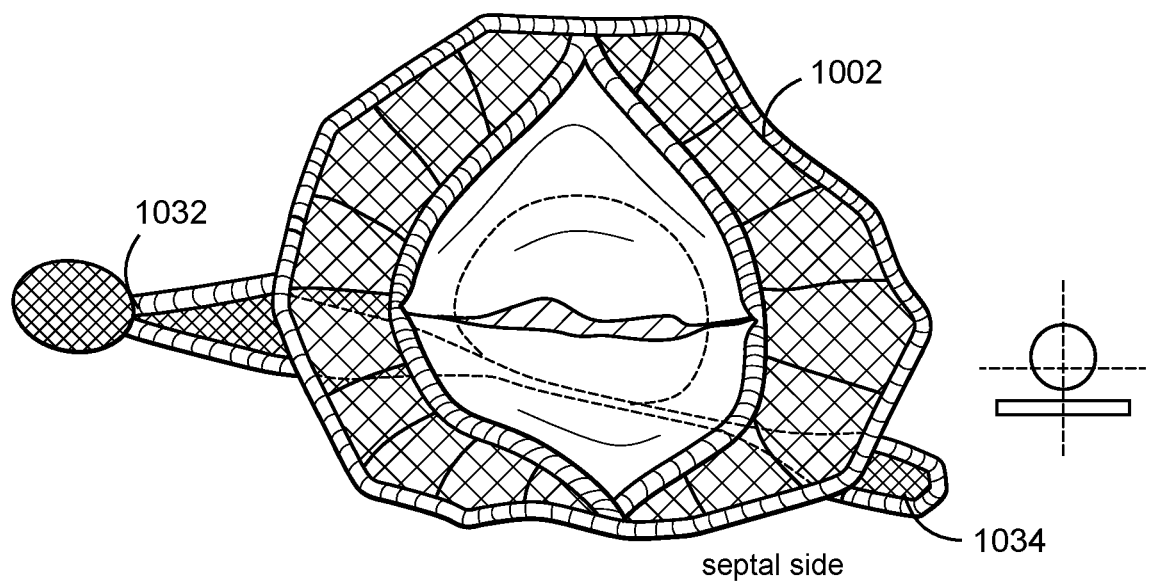

FIGS. 11A and 11B illustrate a top anterior view and a top septal view, respectively, of a side delivered transcatheter prosthetic heart valve 1002 according to an embodiment. The valve 1002 can have a wire frame that includes a wire loop distal anchoring element 1032 and a wire loop proximal anchoring element 1034 attached around the circumference of the frame, beneath a collar 1020 of the valve 1002.

Figure 12:
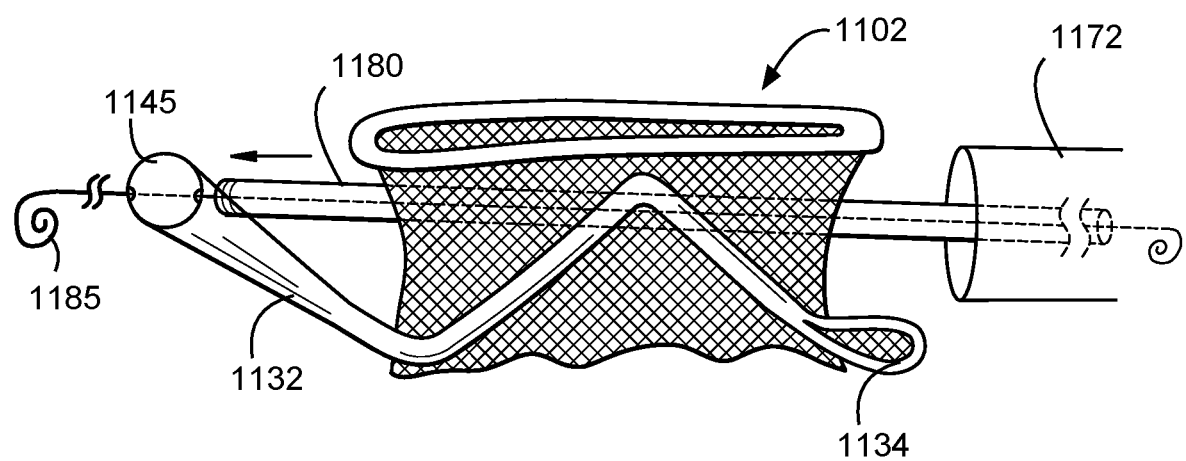
FIG. 12 is a side perspective view illustration of a transcatheter prosthetic valve according to an embodiment, and shown with guide wire coupled to a portion of a distal anchoring element for delivering the valve.

FIG. 12 is an illustration of a side perspective view of a side delivered transcatheter prosthetic heart valve 1102 according to an embodiment. The valve 1102 has a distal anchoring element 1132 and a proximal anchoring element 1134. The distal anchoring element 1132 has a guidewire collar 1145 coupled thereto. The guidewire collar 1145 can be a threaded tip element or the like that can receive a portion of a guidewire 1185. The valve 1102 can be delivered to a native annulus via a delivery catheter 1172. More particularly, the guidewire 1185 can be advanced into a human heart and through an annulus of a native valve. The delivery catheter 1172 can be advanced over the guidewire 1172 to place the distal end of the delivery catheter 1172 on an atrial side of the annulus. The guidewire collar 1145 can be threaded or otherwise positioned over the guidewire 1145. A pusher 1110 can be threaded or otherwise positioned over the guidewire 1145 proximal to the guidewire collar 1145. The guidewire collar 1145 can allow the guidewire 1180 to pass therethrough but can prevent the pusher 1180 from passing through the guidewire collar 1145, thereby providing a mechanism for pushing on the distal anchoring element 1132. The valve 1102 can be advanced through the delivery catheter 1172 with the guidewire collar 1145 being distal to the remaining portion of the valve 1102. Thus, pushing on the guidewire collar 1145 (or distal anchoring element 1132) pulls the valve 1102 through and out of the delivery catheter 1172 from the distal side to avoid damaging compressive pushing forces that may otherwise attend a process of delivering a valve.

Figure 13A:
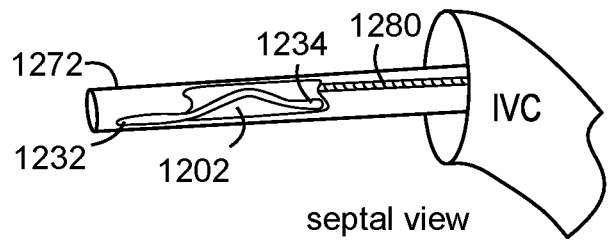
FIGS. 13A-13D, 14A-14D, 15A-15D, and 16A-16E illustrate a process of deploying a transcatheter prosthetic valve in a native annulus of the human heart each according to a different embodiment.
Figure 13B:
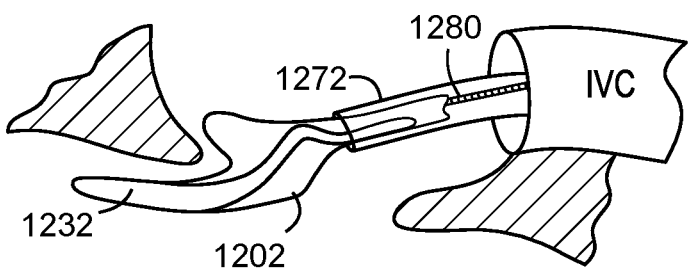
Figure 13C:
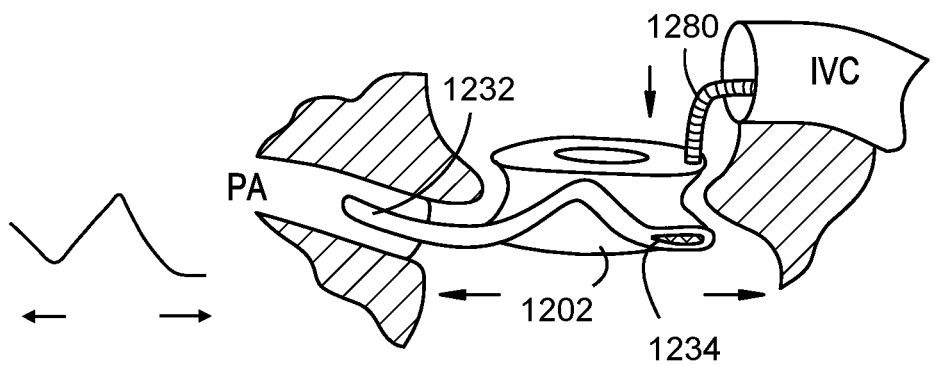
Figure 13D:
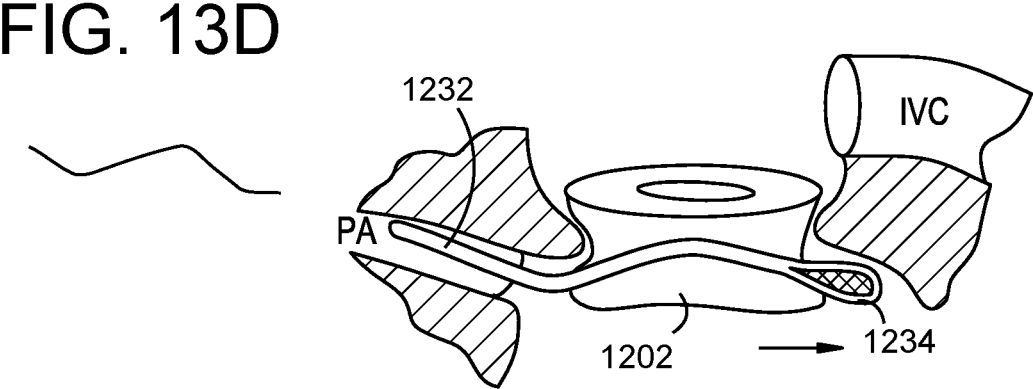

FIGS. 13A-13D illustrate septal side views of a side delivered transcatheter prosthetic heart valve 1202 showing a process of delivering the valve 1202 according to an embodiment. FIG. 13A shows the valve 1202 in a compressed configuration and disposed within a delivery catheter 1272. In some instances, the process can include extending at least a distal end of the delivery catheter 1272 into an atrium of the human heart via the inferior vena cava (IVC). A pusher 1280 or other member can be used to advance the compressed valve 1202 through the delivery catheter 1272 toward the distal end. FIG. 13B shows the valve 1202 partially ejected from the delivery catheter 1272. A distal anchoring element 1232 extends through the annulus and into a ventricular outflow tract such as the pulmonary artery (PA). FIG. 13C shows the valve 1202 ejected from the delivery catheter 1272 and in an uncompressed or expanded configuration. In some implementations, the pusher 1280 can be used to exert a force on a proximal side of the valve 1202 to seat the valve 1202 in the native annulus. A proximal anchoring element 1234 of the valve 1202 can be in a first, compressed, and/or pre-released state as the valve 1202 is seated in the annulus. FIG. 13D shows the valve 1202 seated in the annulus and the proximal anchoring element 1234 in a second, uncompressed, and/or post-released state. For example, a tensile member (not shown) can be manipulated after the valve 1202 is seated in the annulus to allow the proximal anchoring element 1234 to transition to its second state.

Figure 14A:
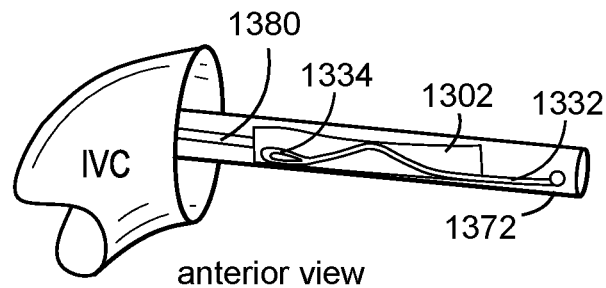
Figure 14B:
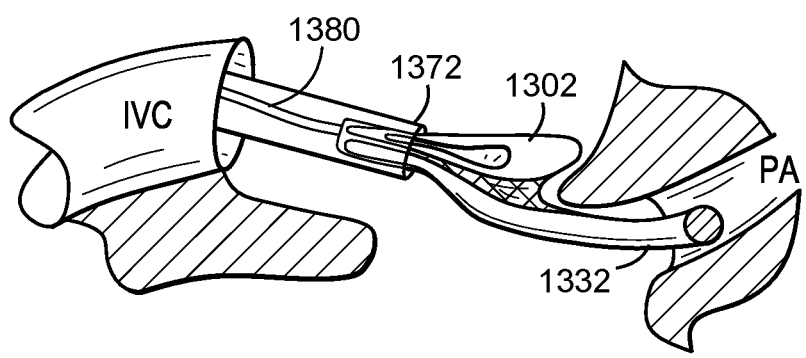
Figure 14C:
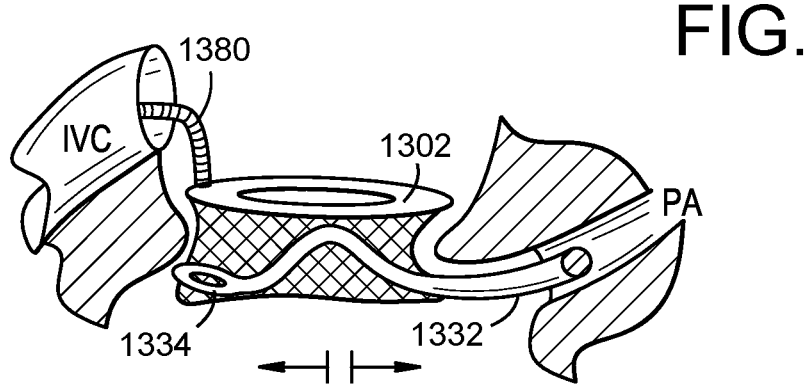
Figure 14D:
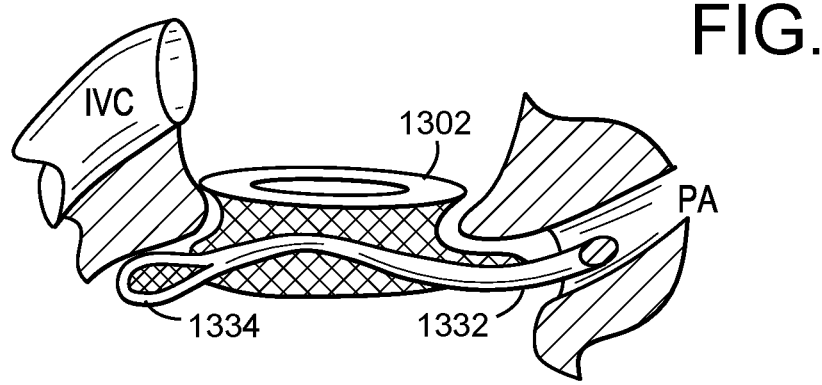

FIGS. 14A-14D illustrate anterior side views of a side delivered transcatheter prosthetic heart valve 1302 showing a process of delivering the valve 1302 according to an embodiment. The valve 1302 can have a wire frame that includes a wire loop distal anchoring element 1332 and a wire loop proximal anchoring element 1334. FIG. 14A shows a portion of a delivery catheter 1372 extending through the IVC having disposed within a lumen thereof the valve 1302 in a compressed configuration. A pusher 1380 or other member can be used to advance the compressed valve 1302 through the delivery catheter 1372. FIG. 14B shows the valve 1302 partially ejected from the delivery catheter 1372 and the distal anchoring element 1332 extending through the annulus and into a ventricular outflow tract such as the PA. FIG. 14C shows the expanded valve 1302 ejected from the delivery catheter 1372 and seated in the annulus of the native valve, while the proximal anchoring element 1334 of the valve 1302 is in a first, compressed, and/or pre-released state. FIG. 14D shows the valve 1302 seated in the annulus and the proximal anchoring element 1334 in a second, uncompressed, and/or post-released state.

Figure 15A:
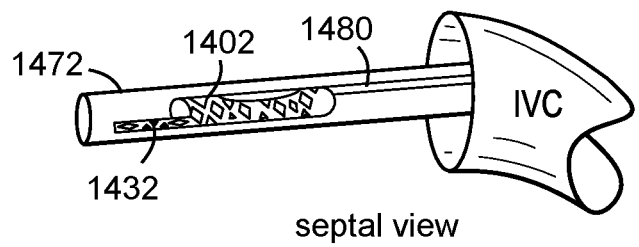
Figure 15B:
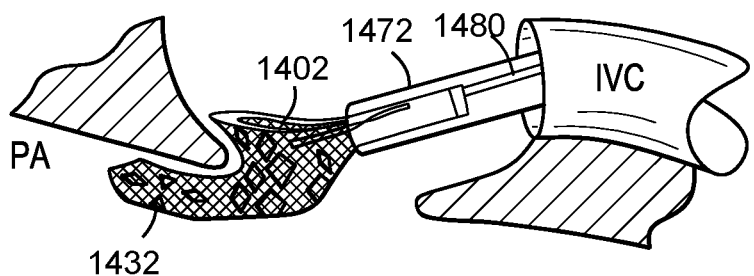
Figure 15C:
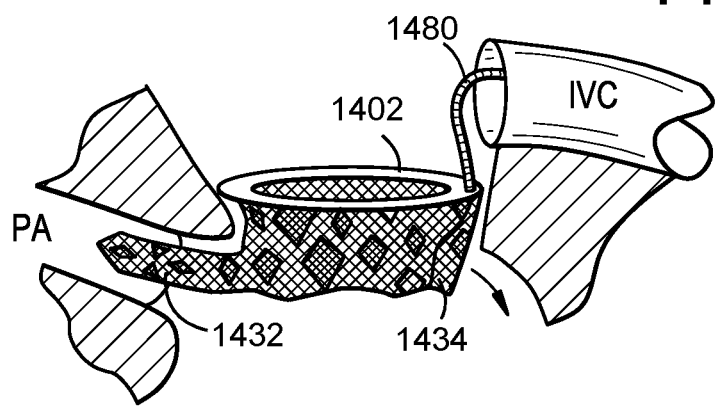
Figure 15D:
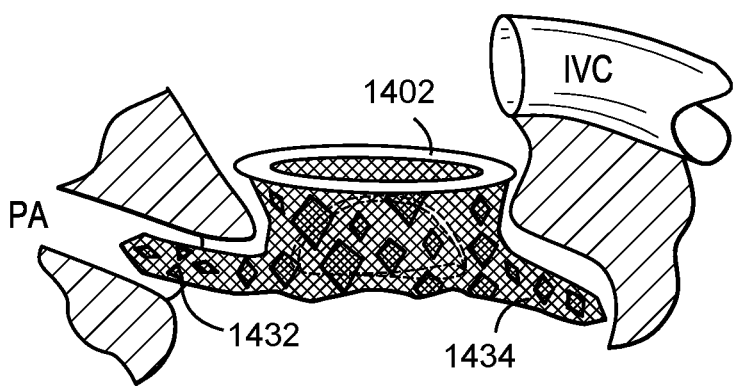

FIGS. 15A-15D illustrate septal side views of a side delivered transcatheter prosthetic heart valve 1402 showing a process of delivering the valve 1402 according to an embodiment. The valve 1402 has a laser cut frame with a laser cut distal anchoring element 1432 and a laser cut proximal anchoring element 1434. FIG. 15A shows a portion of a delivery catheter 1472 extending through the IVC having disposed within a lumen thereof the valve 1402 in a compressed configuration. A pusher 1480 or other member can be used to advance the compressed valve 1402 through the delivery catheter 1472. FIG. 15B shows the valve 1402 partially ejected from the delivery catheter 1472 and the distal anchoring element 1432 extending through the annulus and into a ventricular outflow tract such as the PA. FIG. 15C shows the expanded valve 1402 ejected from the delivery catheter 1472 and seated in the annulus of the native valve, while the proximal anchoring element 1434 of the valve 1402 is in a first, compressed, and/or pre-released state. FIG. 15D shows the valve 1402 seated in the annulus and the proximal anchoring element 1434 in a second, uncompressed, and/or post-released state. For example, the proximal anchoring element 1434 can be unhinged, unfolded, uncompressed, and/or otherwise reconfigured to the second configuration.

Figure 16A:
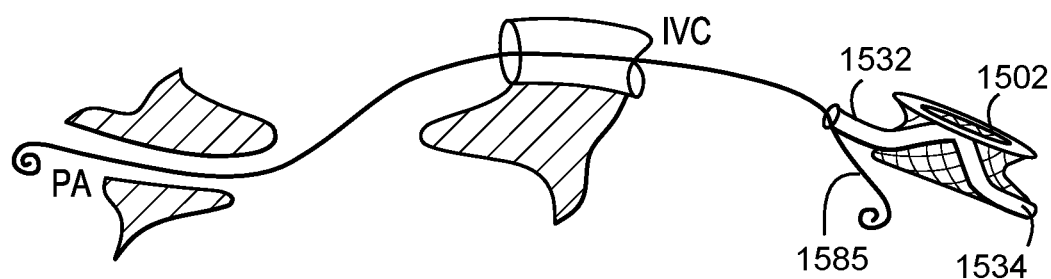
Figure 16B:
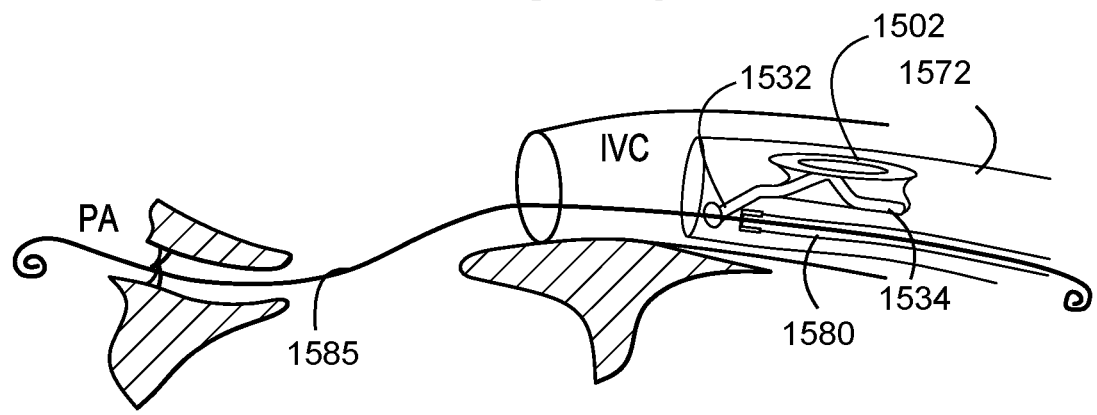
Figure 16C:
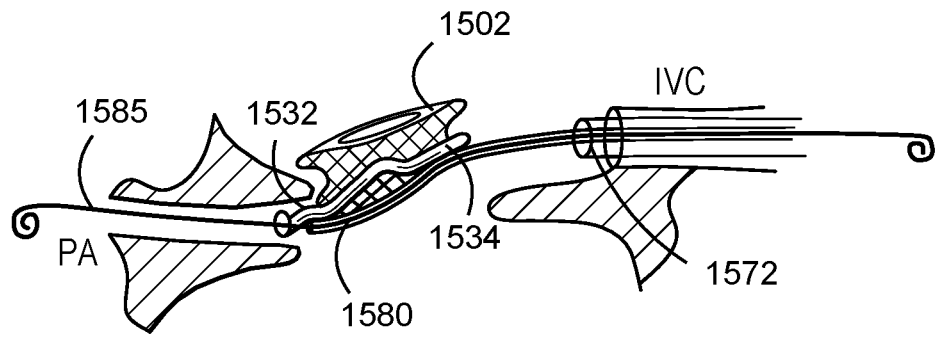
Figure 16D:
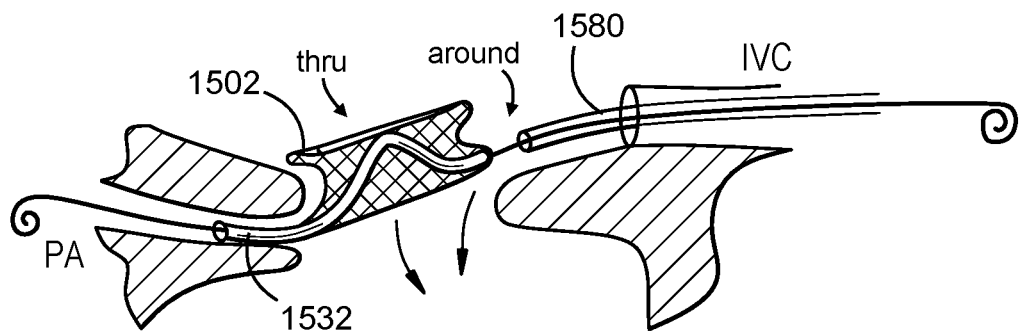
Figure 16E:
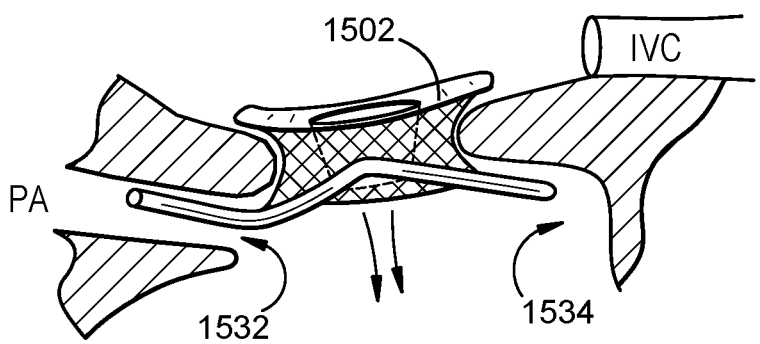

FIGS. 16A-16E illustrate septal side views of a side delivered transcatheter prosthetic heart valve 1502 showing a process of delivering the valve 1502 according to an embodiment. FIG. 16A shows a guidewire 1585 advanced through the IVC, the native annulus, and into a ventricular outflow tract such as the PA. FIG. 16B shows a delivery catheter 1572 being advanced over the guidewire 1585 and through the IVC. In addition, a distal anchoring element 1532 of the valve 1502 can receive and/or can allow the guidewire 1585 to extend through a portion thereof. A pusher 1580 can be used to push on the distal anchoring element 1532 to advance the distal anchoring element 1532 along the guidewire 1585 and through the delivery catheter 1572. FIG. 16C shows the valve 1302 ejected from the delivery catheter 1372 and partially expanded. The distal anchoring element 1332 extends through the annulus and into the PA. FIG. 16D shows the at least partially expanded valve 1502 being temporarily held at an angle relative to the native annulus to allow blood to flow through the native annulus around the valve 1502 as well as through the flow control component (not shown) of the valve 1502. FIG. 16E shows the valve 1502 seated in the annulus. A proximal anchoring element 1534 can be in a first, compressed, and/or pre-released state as the valve 1502 is seated in the annulus and can be allowed to transition to a second, uncompressed, and/or post-released state after the valve 1502 is seated.

Figure 17A:
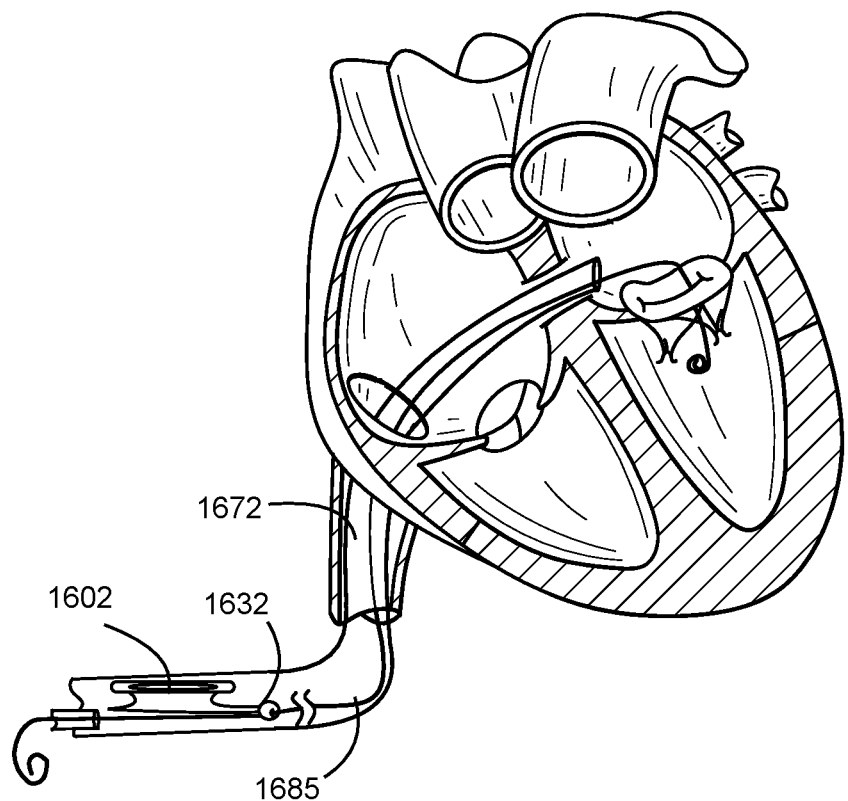
FIGS. 17A-17E illustrate a process of deploying a transcatheter prosthetic valve in a native mitral annulus of the human heart according to an embodiment.
Figure 17B:
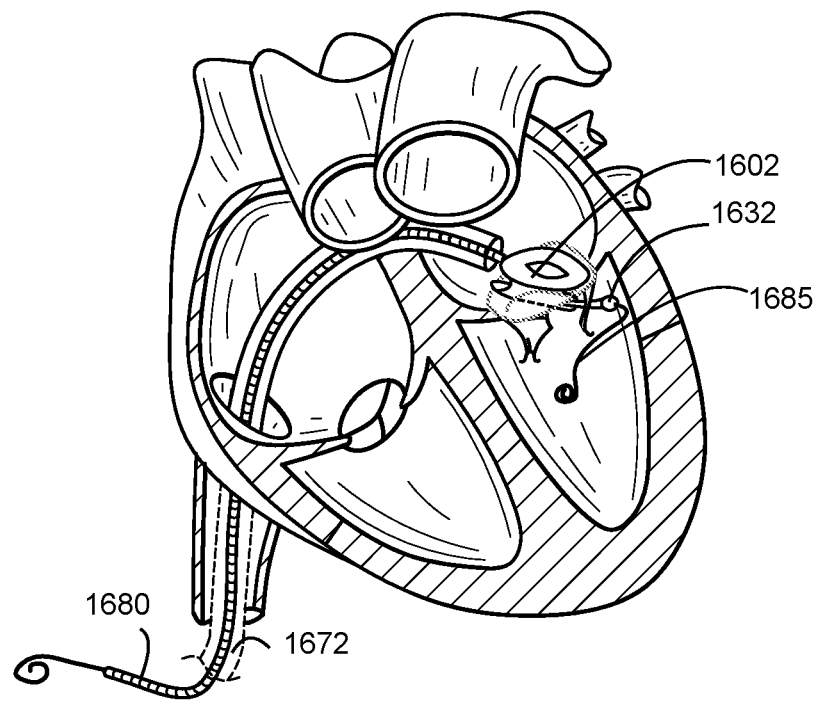
Figure 17C:
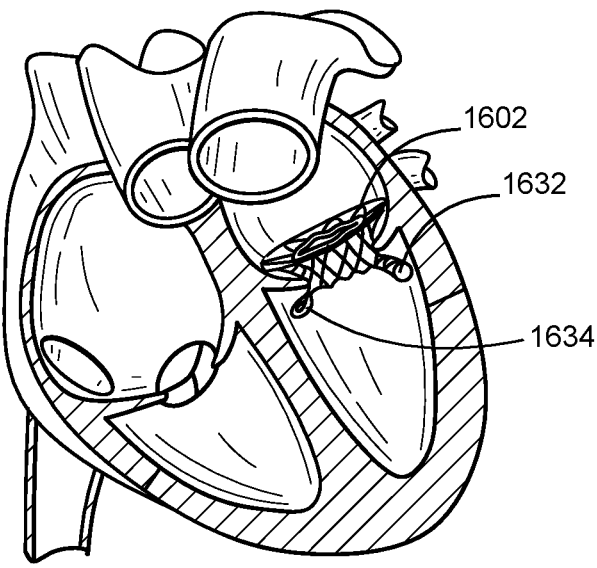
Figure 17D:
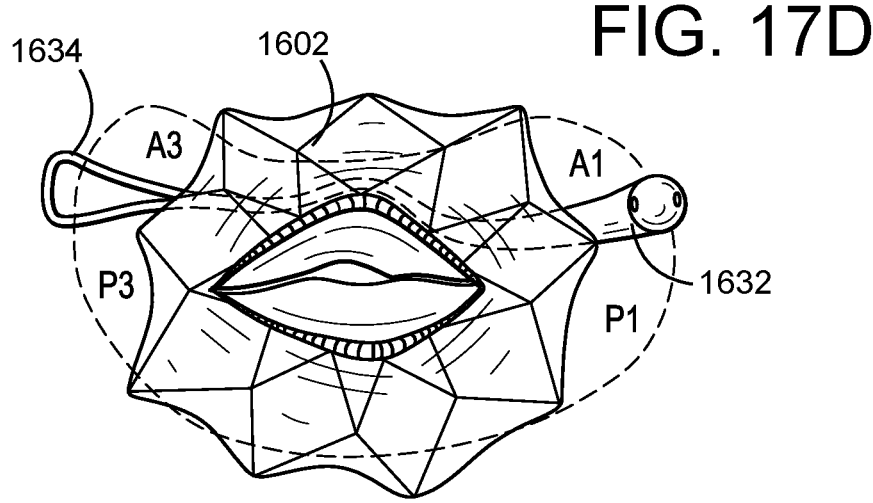
Figure 17E:
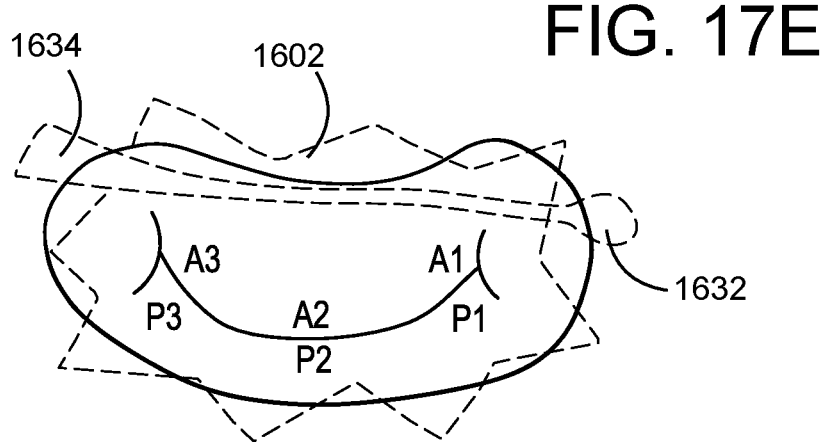

FIGS. 17A-17E illustrate side views of a side delivered transcatheter prosthetic heart valve 1602 showing a process of delivering the valve 1602 to an annulus of a native mitral valve according to an embodiment. FIG. 17A shows a delivery catheter 1672 having the compressed valve 1602 disposed therein. A distal anchoring element 1632 of the valve 1602 is threaded and/or otherwise disposed on a guidewire 1685 that can extend, for example, through the femoral vein and the IVC, transeptally from the right atrium to the left atrium, through the annulus of the mitral valve, and into the left ventricle. A pusher 1680 or other valve advancing tool can be used to advance the compressed valve 1602 through the delivery catheter 1672. FIG. 17B shows the delivery catheter 1672 extending transeptally into the left atrium from the femoral/IVC access, and the pusher 1680 expelling the valve 1602 out of the delivery catheter 1672 such that the distal anchoring element 1632 extends through the annulus and into or near a subannular mitral anterolateral commissure anchoring area. FIG. 17C shows the valve 1602 in an expanded configuration and seated in the annulus of the mitral valve. A proximal anchoring element 1634 is in a released state allowing the proximal anchoring element 1634 to engage a subannular commissure anchoring area. FIG. 17D shows a top view of the valve 1602 positioned relative to the native mitral annulus and shows how the distal anchoring element 132 and the proximal anchoring element 134 provide anchoring in the A1-P1 and A3-P3 commissural anchoring areas. FIG. 17E is a top view of the native mitral valve annulus shown in solid line and the valve 1602 seated therein shown in dashed line.

Figure 18A:
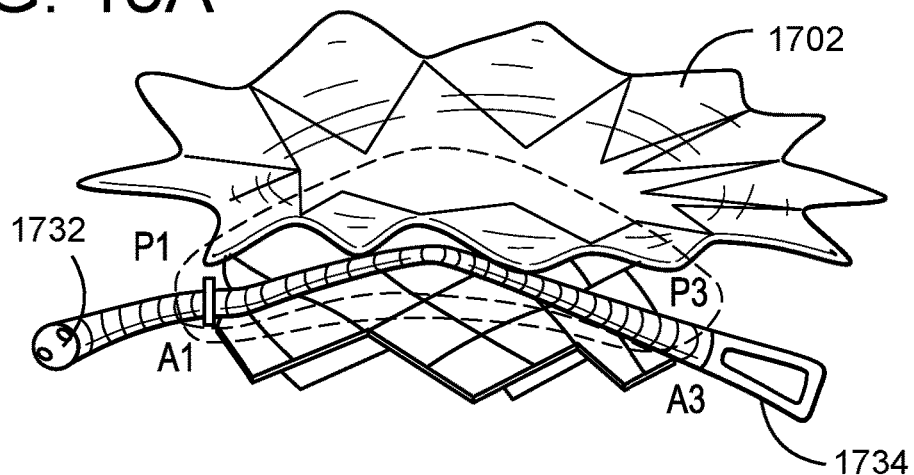
FIG. 18A is an anterior side perspective view illustration of a transcatheter prosthetic valve in a native mitral annulus of the human heart according to an embodiment.
Figure 18B:
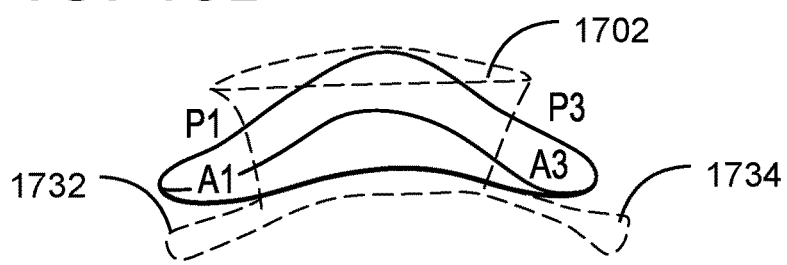
FIG. 18B is a side view illustration of the transcatheter prosthetic valve of FIG. 18A (shown in dashed line) and disposed in the native mitral annulus (shown in solid line).

FIGS. 18A and 18B illustrate anterior side views of a side delivered transcatheter prosthetic heart valve 1702 seated in an annulus of a native mitral valve according to an embodiment. FIG. 18A shows how a distal anchoring element 1732 and a proximal anchoring element 1734 provide anchoring in the A1-P1 and A3-P3 commissural anchoring areas (shown in dashed line). FIG. 18B is a side view of the native mitral valve annulus shown in solid line and the valve 1702 seated therein shown in dashed line.

Figure 19A:
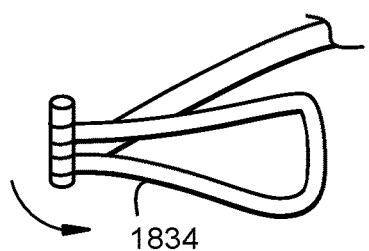
FIGS. 19A and 19B are perspective view illustrations of a proximal anchoring element in a first configuration and a second configuration, respectively, according to an embodiment.
Figure 19B:
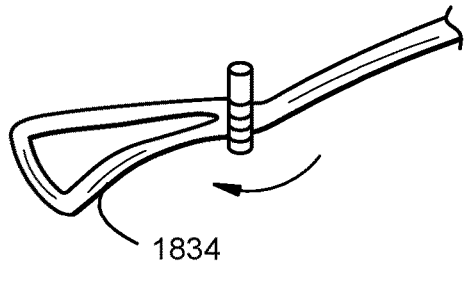

FIGS. 19A and 19B are illustrations of a proximal anchoring element 1834 included in a transcatheter prosthetic heart valve according to an embodiment and shown in a first configuration and a second configuration, respectively. The proximal anchoring element 1834 can include, for example, a mechanical hinge or similar mechanism allowing at least an end portion of the proximal anchoring element 1834 to rotate relative to the remaining portion of the proximal anchoring element 1834. Although not shown, in some implementations, the end portion of the proximal anchoring element 1834 can be engaged by a tensile member and/or the like configured to retain the proximal anchoring element 1834 in the first configuration prior to seating the valve in an annulus.

Figure 20A:
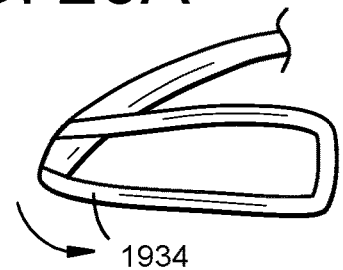
FIGS. 20A and 20B are perspective view illustrations of a proximal anchoring element in a first configuration and a second configuration, respectively, according to an embodiment.
Figure 20B:
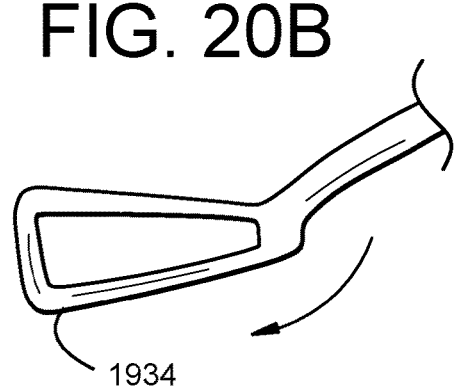

FIGS. 20A and 20B are illustrations of a proximal anchoring element 1934 included in a transcatheter prosthetic heart valve according to an embodiment and shown in a first configuration and a second configuration, respectively. The proximal anchoring element 1934 can include, for example, a fold and/or release region or mechanism formed of shape memory or superelastic material such as Nitinol. The proximal anchoring element 1934 can be in a folded state when in the first configuration and an unfolded or expanded state when in the second configuration. Although not shown, in some implementations, the end portion of the proximal anchoring element 1934 can be engaged by a tensile member and/or the like configured to retain the proximal anchoring element 1934 in the first configuration prior to seating the valve in an annulus.

Figure 21A:
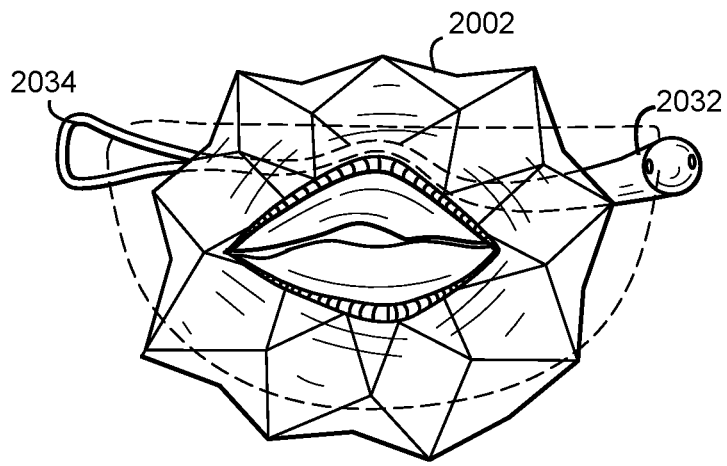
FIG. 21A is a top view illustration of a transcatheter prosthetic valve in a native tricuspid annulus of the human heart according to an embodiment.
Figure 21B:
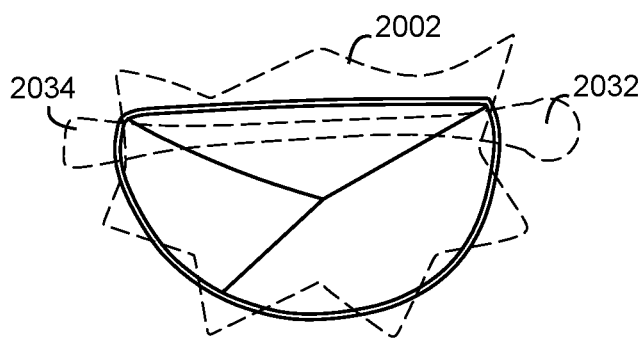
FIG. 21B is a top view illustration of the transcatheter prosthetic valve of FIG. 21A (shown in dashed line) and disposed in the native tricuspid annulus (shown in solid line).
Figure 22:
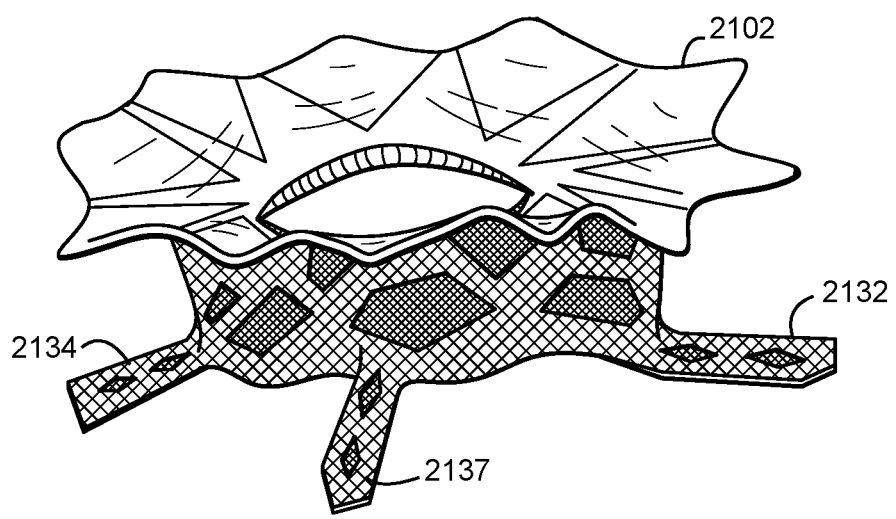
FIG. 22 is a side perspective view illustration of a transcatheter prosthetic valve having multiple subannular anchoring elements according to an embodiment.

FIGS. 21A and 21B illustrate top views of a side delivered transcatheter prosthetic heart valve 2002 seated in an annulus of a native tricuspid according to an embodiment. FIG. 21A shows how a distal anchoring element 2032 and a proximal anchoring element 2034 provide anchoring in the RVOT and proximal anchoring area (adjacent the IVC), respectively. FIG. 21B is a top view of the native valve annulus shown in solid line with the valve 1702 seated therein shown in dashed line.

Figure 24:
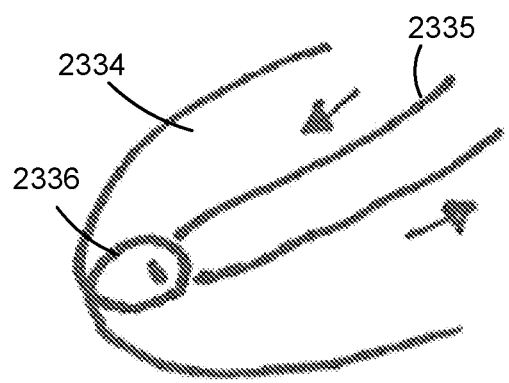
FIGS. 24 and 25 are side perspective view illustrations of a portion of a proximal anchoring element of a transcatheter prosthetic valve coupled to a tensile member, each according to a different embodiment.

FIG. 24 is an illustration of a side perspective view of a side delivered transcatheter prosthetic heart valve 2102 according to an embodiment. The valve 2102 can include a wire or laser cut frame having any suitable number of subannular anchoring elements. For example, in this embodiment, the valve 2102 includes three subannular anchoring elements, such as a distal anchoring element 2132, a proximal anchoring element 2134, and a medial anchoring element 2137.

Any of the valves described herein can include a proximal anchoring element that can be transitioned from a first state or configuration to a second state or configuration after the valve has been inserted or seated in an annulus of a native valve. For example, a proximal anchoring element can be configured to transition between a compressed, undeployed, restrained, and/or pre-released state (e.g., the first configuration) and an expanded, extended, deployed, unrestrained, and/or post-released state. When in the first configuration, a proximal anchoring element can be in contact with, adjacent to, and/or otherwise near a body or transannular section of the valve. When in the second configuration, the proximal anchoring element (or at least an end portion thereof) can extend away from the body or transannular section of the valve. That is to say, at least the end portion of the proximal anchoring element in the second configuration can be farther from the body or transannular section of the valve compared to the end portion of the proximal anchoring element in the first configuration. Such an arrangement can result in a size, circumference, and/or perimeter of at least a portion of the body or transannular section of the valve being smaller when the proximal anchoring element is in the first configuration than when the proximal anchoring element is in the second configuration, which in turn, can allow the body or transannular section of the valve (or a portion thereof) to be inserted through the annulus. Once the valve is seated and the proximal anchoring element is transitioned to its second configuration, the larger size, circumference, and/or perimeter of the body or transannular section can act to secure and/or anchor the valve in the annulus.

In some embodiments, a valve can include a feature, member, mechanism, etc. configured to at least temporarily retain a proximal anchoring element in its first configuration. For example, a valve can include a tensile member that can selectively engage a proximal anchoring element to temporarily maintain the proximal anchoring element in the first configuration. In some implementations, the tensile member can removably couple to a portion of the proximal anchoring element and can exert a force (e.g., a tensile or compression force) operable in maintaining the proximal anchoring element in the first configuration. The tensile member can be reconfigurable allowing the tensile member to be disengaged from the proximal anchoring element, which in turn, can allow the proximal anchoring element to transition from its first configuration to its second configuration, as described in further detail herein with reference to specific embodiments.

Provided below is a discussion of certain aspects, embodiments, and/or methods of removably coupling a tensile member to a proximal anchoring element of a transcatheter prosthetic valve. The proximal anchoring elements (or aspects or portions thereof) described below with respect to specific embodiments can be substantially similar in at least form and/or function to any of the proximal anchoring elements described herein. Similarly, the tensile members described below (or aspects or portions thereof) can be similar in at least form and/or function to any of the tensile members described herein. Thus, certain aspects and/or portions of the specific embodiments may not described in further detail herein.

Figure 23A:
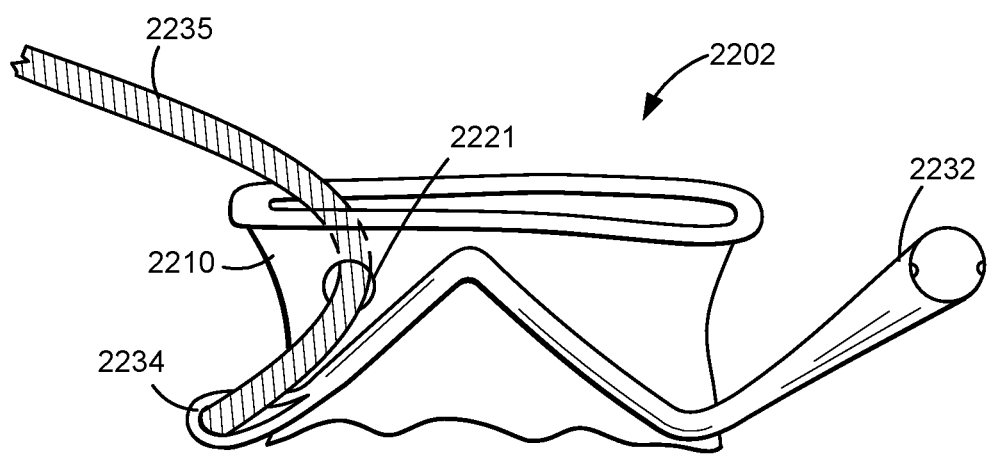
FIGS. 23A and 23B are a side perspective view illustrations of a transcatheter prosthetic valve having a proximal anchoring element being coupled to a tensile member and decoupled from the tensile member, respectively, according to an embodiment.
Figure 23B:
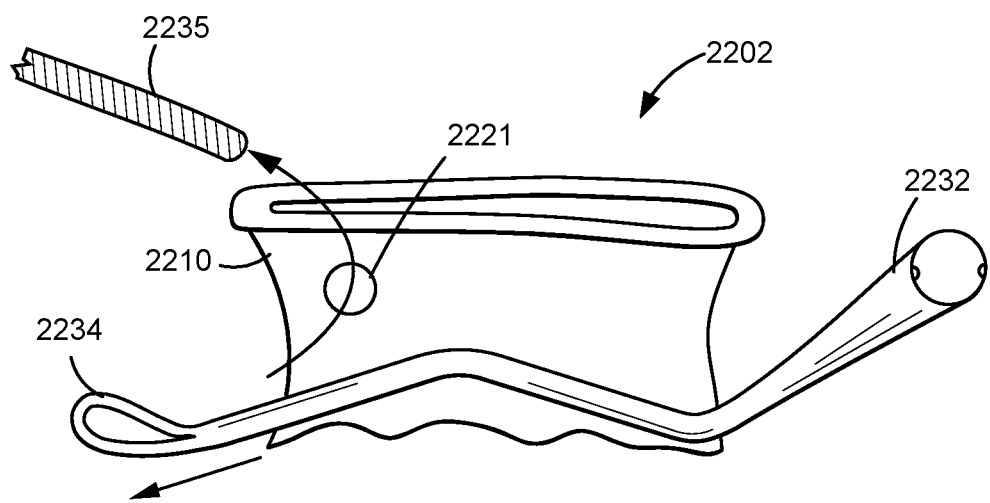

FIGS. 23A and 23B illustrate side perspective views of a side delivered transcatheter prosthetic heart valve 2202 and a tensile member 2235 according to an embodiment. The valve 2202 has a frame 2210 with a distal anchoring element 2232 and a proximal anchoring element 2234 (e.g., wire loop anchoring elements and/or any other suitable type of anchoring element). The tensile member 2235 can be and/or can include any suitable coupler, attachment device, and/or the like configured to be at least temporarily coupled to the proximal anchoring element 2234. In some embodiments, the tensile member 2235 can be a tether that can be advanced through a delivery catheter as the valve is advanced therethrough. In some embodiments, the tensile member 2235 can be and/or can include a pusher that can be used to advance the valve through the delivery catheter.

FIG. 23A shows the tensile member 2235 coupled to the proximal anchoring element 2234. Although not shown, the proximal anchoring element 2234 and/or the tensile member 2235 can include one or more features allowing tensile member 2235 to temporarily couple to the proximal anchoring element 2234. The tensile member 2235 is at least partially disposed within the valve 2202. An end portion of the tensile member 2235 is shown extending through a waypoint 2221 defined by a portion of the valve 2202 (e.g., a portion of the frame 2210). The waypoint 2221 can be, for example, an opening, an aperture, a slot, a cut, self-healing port, etc. Such an arrangement can result in the end portion of the tensile member 2235 substantially forming a U-bend, where a distal end surface of the tensile member 2235 is oriented and/or faces a proximal direction. Accordingly, applying a tensile force along the tensile member 2235 can act to pull the proximal anchoring element 2234 toward a body or transannular section of the valve 2202. Said another way, a user can pull on a proximal end portion of the tensile member 2235 (e.g., an end disposed outside of the body) to place the tensile member 2235 in tension that pulls the proximal anchoring element 2234 toward the body of the valve 2202—i.e., its first configuration.

FIG. 23B shows the tensile member 2235 decoupled from the proximal anchoring element 2234 and withdrawn through the waypoint 2201 and the valve 2202. Although not shown, the tensile member 2235, the proximal anchoring element 2234, and/or any suitable member or element of a delivery system can include a release mechanism that can release the proximal anchoring element 2234 from the tensile member 2235. Once decoupled, the tensile member 2235 can be retracted from the valve 2202. The decoupling allows the proximal anchoring element 2234 to transition from its first configuration to its second configuration. In some implementations, the tensile member 2235 can remain coupled to the proximal anchoring element 2234 as the valve 2202 is placed in the annulus of the native valve and can be released or decoupled after the valve 2202 is placed or seated. As described above, the proximal anchoring element 2234 is configured to engage subannular tissue such as, for example, the septal-posterior and/or anterior-septal commissures bridging the posterior and anterior leaflets of the native valve.

FIG. 24 is an illustration of a side perspective view of a portion of a proximal anchoring element 2334 included in a transcatheter prosthetic heart valve and a tensile member 2335 according to an embodiment. The proximal anchoring element 2334 includes an attachment point 2336 (e.g., an eyelet, hole, loop, hook, aperture, etc.) to which the tensile member 2335 is removably coupled. The tensile member 2335 is shown, for example, as a continuous tether, cable, suture, wire, and/or the like. A portion of the tensile member 2335 is threaded through a delivery system, a portion of the valve (e.g., a waypoint thereof), looped around or through the attachment point 2336 of the proximal anchoring element 2334, and threaded back through the delivery system. Pulling on both ends of the tensile member 2335 places the tensile member 2335 in tension, which in turn, maintains the proximal anchoring element 2334 in its first configuration. After the valve has been deployed, one end of the tensile member 2335 is pulled to remove the tensile member 2335 from the attachment point 2336 of the proximal anchoring element 2334.

Figure 25:
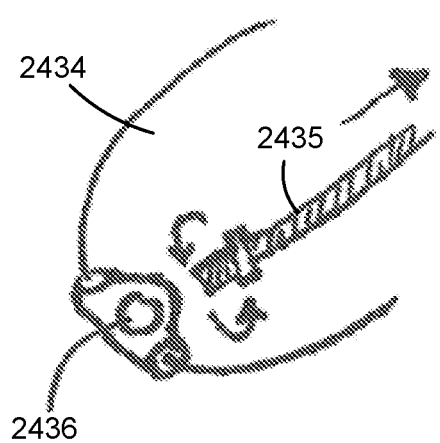

FIG. 25 is an illustration of a side perspective view of a portion of a proximal anchoring element 2434 included in a transcatheter prosthetic heart valve and a tensile member 2435 according to an embodiment. The proximal anchoring element 2434 includes an attachment point 2436 (e.g., a threaded eyelet, opening, or coupler) to which the tensile member 2435 is removably coupled. The tensile member 2435 is shown, for example, as a continuous cable with a threaded distal end portion. The tensile member 2435 can extend through a delivery system and a portion of the valve (e.g., a waypoint thereof), and can form a threaded coupling with the attachment point 2436 of the proximal anchoring element 2434. Pulling on an end of the tensile member 2435 places the tensile member 2435 in tension, which in turn, maintains the proximal anchoring element 2434 in its first configuration. After the valve has been deployed, the tensile member 2435 is twisted to unthread the threaded distal end portion from attachment point 2436 and removed from the delivery system.

Figure 26:
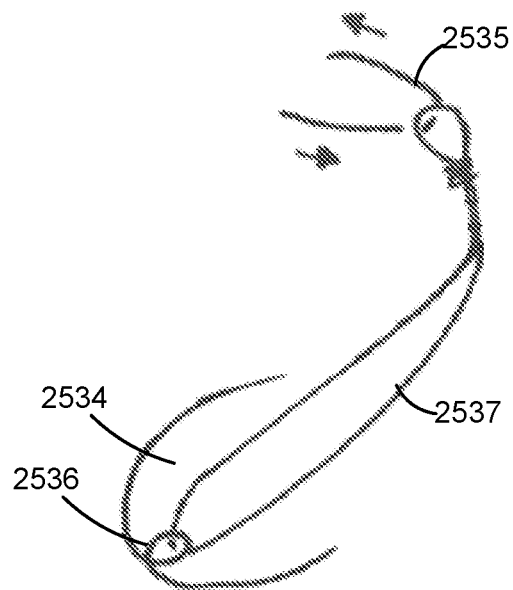
FIGS. 26 and 27 are side perspective view illustrations of a portion of a proximal anchoring element of a transcatheter prosthetic valve and a tensile member, each according to a different embodiment.

FIG. 26 is an illustration of a side perspective view of a portion of a proximal anchoring element 2534 included in a transcatheter prosthetic heart valve and a tensile member 2535 according to an embodiment. The proximal anchoring element 2534 includes an attachment point 2536 such as an eyelet or loop to which a lead 2537 of the tensile member 2535 is coupled. The lead 2537 can be configured to remain coupled to the valve after deployment. In some implementations, a first end of the lead 2537 can be coupled to the attachment point 2536 and a second end of the lead 2537 opposite the first end can extend through a portion of the valve (e.g., the waypoint and any other suitable portion). Such an arrangement can result in the second end of the lead 2537 being disposed, for example, outside of and/or above a collar of the valve, which can be more accessible than the attachment point 2536 of the proximal anchoring element 2334.

The tensile member 2535 is shown, for example, as a continuous tether, cable, suture, wire, and/or the like that can be threaded through a delivery system, looped around or through the second end of the lead 2537, and threaded back through the delivery system. Pulling on both ends of the tensile member 2535 places the tensile member 2535 in tension, which in turn, places the lead 2537 in tension. Thus, the lead 2537 maintains the proximal anchoring element 2534 in its first configuration. After the valve has been deployed, one end of the tensile member 2535 is pulled to remove the tensile member 2535 from the second end of the lead 2536. The tensile member 2535 is removed from the delivery system while the lead 2537 remains coupled to the proximal anchoring element 2534.

Figure 27:
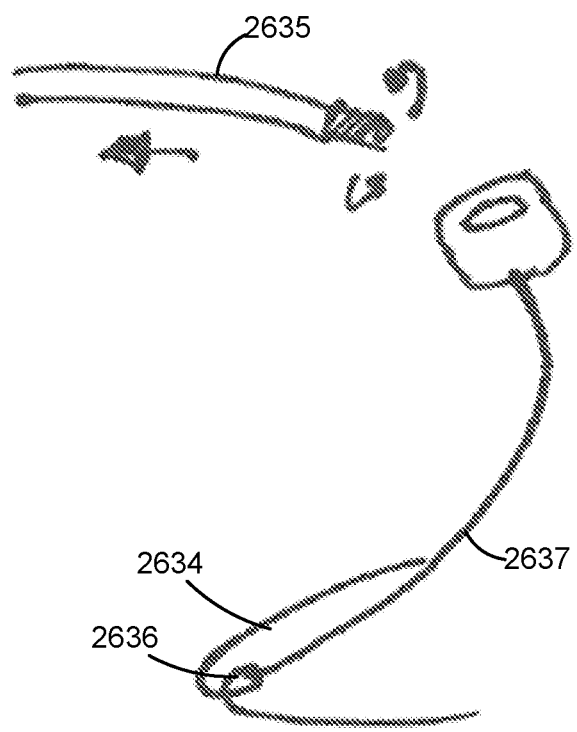

FIG. 27 is an illustration of a side perspective view of a portion of a proximal anchoring element 2634 included in a transcatheter prosthetic heart valve and a tensile member 2635 according to an embodiment. The proximal anchoring element 2634 includes an attachment point 2636 to which a lead 2637 of the tensile member 2635 is coupled. A first end of the lead 2637 can be coupled to the attachment point 2636 and a second end of the lead 2637 opposite the first end can extend through a portion of the valve (e.g., the waypoint and any other suitable portion). The tensile member 2635 is shown, for example, as a continuous cable with a threaded distal end portion, which can form a removable threaded coupling with the second end of the lead 2637. Pulling on an end of the tensile member 2635 places the tensile member 2635 in tension, which in turn, places the lead 2637 in tension. Thus, the lead 2637 maintains the proximal anchoring element 2634 in its first configuration. After the valve has been deployed, the tensile member 2635 is twisted to unthread the threaded distal end portion from the second end of the lead 2637 and removed from the delivery system while the lead 2637 remains coupled to the proximal anchoring element 2634.

Figure 28A:
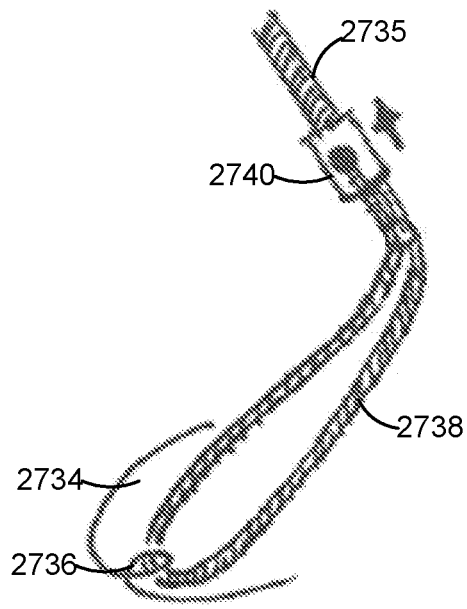
FIGS. 28A and 28B are side perspective view illustrations of a portion of a proximal anchoring element of a transcatheter prosthetic valve coupled to a tensile member according to an embodiment, and shown with the tensile member in a first configuration and a second configuration, respectively.
Figure 28B:
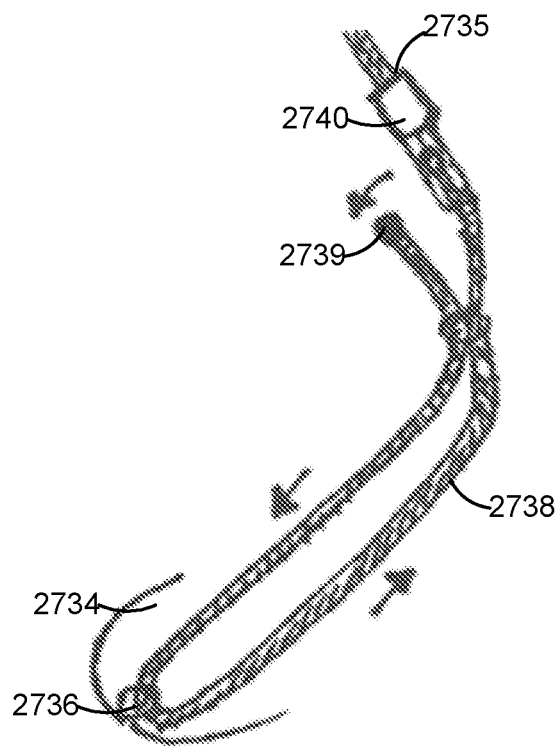

FIGS. 28A and 28B illustrate a side perspective view of a portion of a proximal anchoring element 2734 included in a transcatheter prosthetic heart valve and a tensile member 2735 according to an embodiment. The proximal anchoring element 2734 includes an attachment point 2736 to which an end portion 2738 of the tensile member 2735 is removably coupled. The tensile member 2735 is shown, for example, as a continuous tether, cable, suture, wire, and/or the like with a coupling feature 2739 (e.g., a ball, knob, protrusion, etc.) included in and/or formed at the distal end. The tensile member 2735 includes a receiving member 2740 (e.g., a cup or the like) configured to removably receive the end of the tensile member 2735 (e.g., the coupling feature 2739). For example, the coupling feature 2739 can be disposed or snapped into a recessed feature of the receiving member 2740, which can be coaxial with an outer sleeve member. The outer sleeve member can be slid (e.g., in a distal direction) to cover the coupling feature 2739 and to form a friction fit that maintains the coupling feature 279 in the recessed feature of the receiving member 2740 while covered by the sleeve member.

FIG. 28A shows the end portion 2738 of the tensile member 2735 threaded through a portion of the valve (e.g., a waypoint thereof), looped around or through the attachment point 2736 of the proximal anchoring element 2734, and threaded back through the portion of the valve (e.g., back through the waypoint) to allow the coupling feature 2739 at the end of the tensile member 2735 to be coupled to the receiving member 2740. Pulling on a proximal end of the tensile member 2735 places the tensile member 2735 in tension, which in turn, maintains the proximal anchoring element 2734 in its first configuration. FIG. 28B shows the sleeve member in a position that allows the coupling feature 2739 at the end of the tensile member 2735 to be removed from the receiving member 2740. After the valve has been deployed and the coupling feature 2739 is released from the receiving member 2740, the tensile member 2735 is pulled to remove the tensile member 2735 from the attachment point 2736 of the proximal anchoring element 2734 and the delivery system.

FIGS. 29A-29D illustrate a side perspective view of a portion proximal anchoring element 2834 included in a transcatheter prosthetic heart valve and one or more portions of a tensile member 2835 according to an embodiment. The proximal anchoring element 2834 includes an attachment point 2836 to which a lead 2841 of the tensile member 2835 is coupled. Each end of the lead 2841 includes a coupling feature 2842 (e.g., a ball or the like) and is configured to at least temporarily couple to a receiving member 2843 of the tensile member 2835.

Figure 29A:
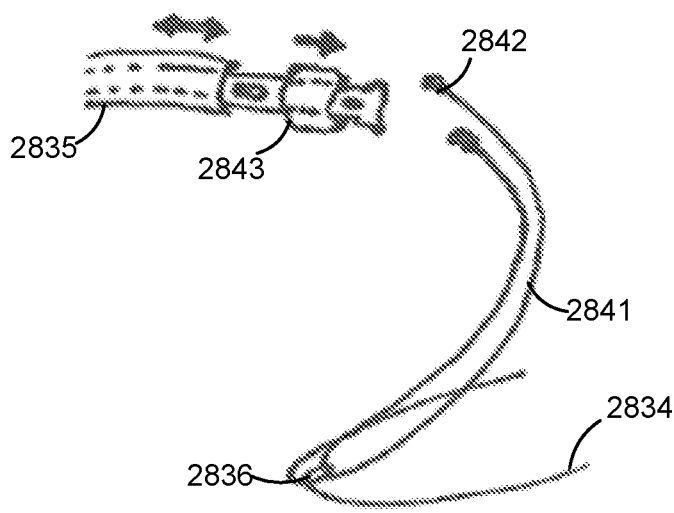
FIGS. 29A-29D are side perspective view illustrations of a portion of a proximal anchoring element of a transcatheter prosthetic valve being coupled to and decoupled from a tensile member according to an embodiment.
Figure 29B:
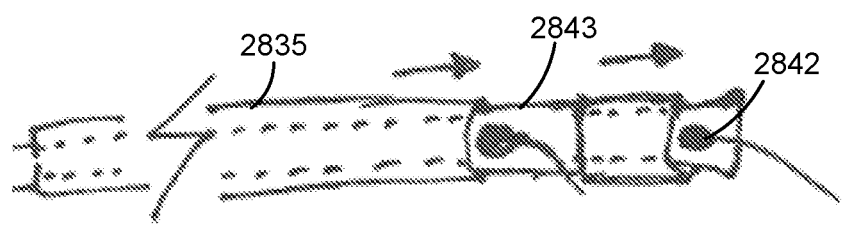
Figure 29C:
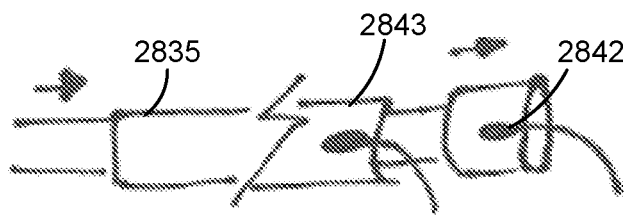

FIG. 29A shows the lead 2841 threaded through a portion of the valve (e.g., a waypoint thereof), looped around or through the attachment point 2836 of the proximal anchoring element 2834, and threaded back through the portion of the valve (e.g., back through the waypoint) such that each end of the lead 2841 is outside of the valve. FIGS. 29B and 29C show the coupling features 2842 disposed at each end of the lead 2841 being coupled to the receiving member 2843 of the tension member 2835. For example, the receiving member 2843 can define two recessed features and two sleeve members. Each coupling feature 2842 can be disposed in a corresponding recessed feature and each sleeve member can be transitioned to cover each coupling feature 2842, thereby coupling the lead 2841 to the tensile member 2835. Pulling on an end of the tensile member 2835 places the tensile member 2835 in tension, which in turn, places the lead 2841 in tension. Thus, the lead 2841 maintains the proximal anchoring element 2834 in its first configuration.

Figure 29D:
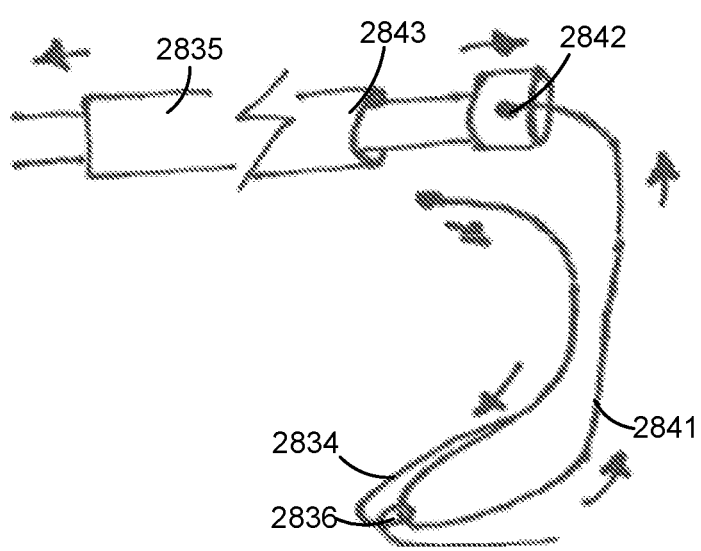

FIG. 29D shows one of the sleeve members of the receiving member 2843 (e.g., a proximal sleeve member) transitioned to a position that allows the corresponding coupling feature 2842 to be removed from the corresponding recessed feature of the receiving member 2843. After the valve has been deployed and the coupling feature 2842 is released from the receiving member 2843, the tensile member 2835 is pulled to remove the tensile member 2835. Moreover, one of the coupling features 2842 can remain coupled to the receiving member 2843 such that the lead 2841 is removed from the attachment point 2836 of the proximal anchoring element 2834, allowing the tensile member 2835 and the lead 2841 to be removed from the delivery system.

Figure 30:
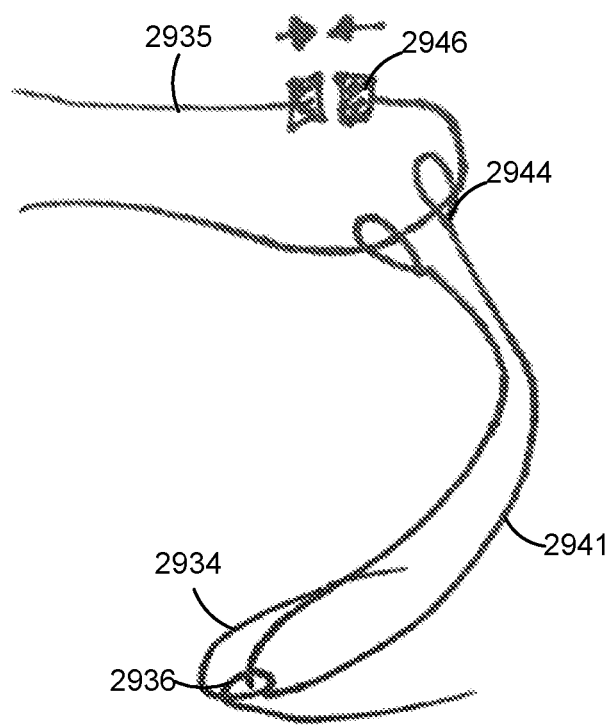
FIG. 30 is a side perspective view illustration of a portion of a portion of a proximal anchoring element of a transcatheter prosthetic valve coupled to a tensile member according to an embodiment.

FIG. 30 is an illustration of a side perspective view of a portion of a proximal anchoring element 2934 included in a transcatheter prosthetic heart valve and a tensile member 2935 according to an embodiment. The proximal anchoring element 2934 includes an attachment point 2936 to which a lead 2941 of the tensile member 2935 is coupled. Each end of the lead 2941 includes a coupling feature 2942 (e.g., a loop or the like) and is configured to at least temporarily couple to the tensile member 2835. An end of the lead 2941 is threaded through a portion of the valve (e.g., a waypoint thereof), looped around or through the attachment point 2936 of the proximal anchoring element 2934, and threaded back through the portion of the valve (e.g., back through the waypoint) such that the coupling feature 2944 at each end of the lead 2941 is outside of the valve.

The tensile member 2935 is shown, for example, as a continuous suture and/or the like that can be threaded through the coupling features 2944 at each end of the lead 2941, thereby coupling the tensile member 2935 to the lead 2941. Pulling on both ends of the tensile member 2935 places the tensile member 2935 in tension, which in turn, places the lead 2941 in tension. Thus, the lead 2941 maintains the proximal anchoring element 2934 in its first configuration. After the valve has been deployed, a portion of the tensile member 2935 can be severed allowing at least the tensile member 2935 to be removed from the delivery system. In some implementations, the severing of the tensile member 2935 can include cutting the tensile member 2935 and/or otherwise breaking apart a portion of the tensile member 2935 at a breakpoint 2946. For example, the breakpoint 2946 can include and/or can form a frangible portion of the tensile member 2935, a magnetic coupler, a threaded coupler, a ball and cup coupler, and/or any other suitable coupler. Moreover, the severing of the tensile member 2935 can result in one end portion of the lead 2941 remaining coupled to the tensile member 2935, which in turn, can allow the lead 2941 to be removed within the tensile member 2935.

Figure 31A:
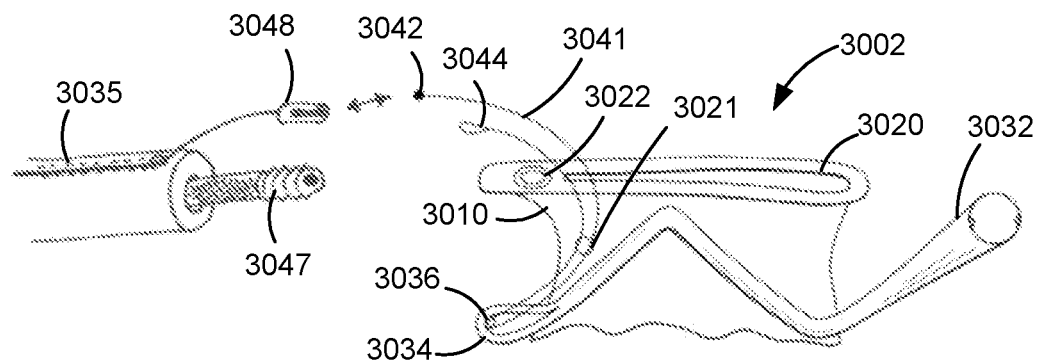
FIGS. 31A-31C are side perspective view illustrations of a portion of a proximal anchoring element of a transcatheter prosthetic valve being coupled to and decoupled from a tensile member according to an embodiment.
Figure 31B:
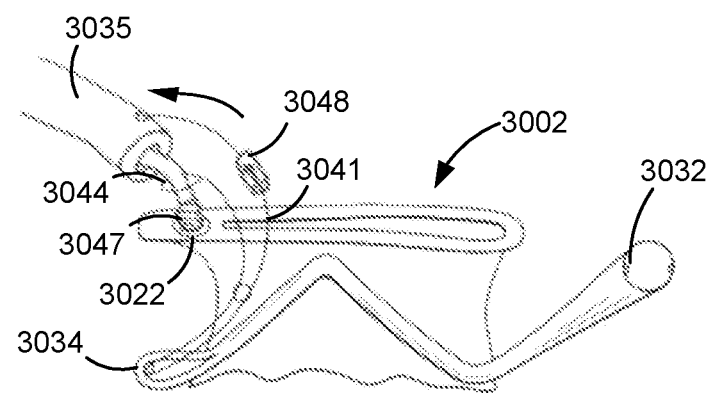
Figure 31C:
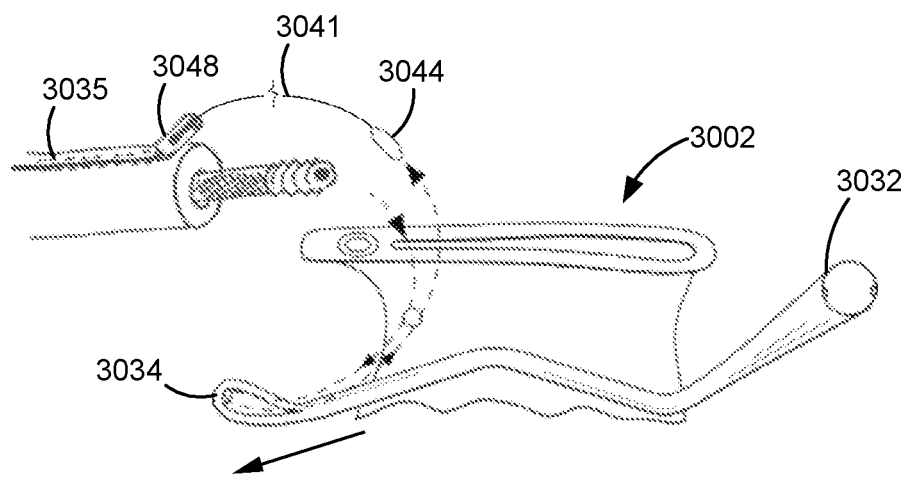

FIGS. 31A-31C illustrate side perspective views of a side delivered transcatheter prosthetic heart valve 3002 and a tensile member 3035 according to an embodiment. The valve 3002 has a frame 3010 with a collar 3020, a distal anchoring element 3032, and a proximal anchoring element 3034 (e.g., wire loop anchoring elements and/or any other suitable type of anchoring element). The frame 3010 defines a waypoint 3021. The collar 3020 includes and/or forms a coupler 3022. While the waypoint 3021 is shown along a body of the frame 3010, in other embodiments, the collar 3020 and/or any other suitable portion of the valve 3002 can form and/or define the waypoint 3021. Similarly, while the coupler 3022 is shown along the collar 3020, in other embodiments, the body of the frame 3010 and/or any other suitable portion of the valve 3020 can include the coupler 3022.

The tensile member 3035 includes a lead 3041 configured to be coupled to and/or threaded through an attachment point 3036 of the proximal anchoring element 3034. The lead 3041 includes a first end that has and/or forms a first coupling feature 3044 and a second end that has and/or forms a second coupling feature 3044. The coupling features can be any suitable configuration. For example, in this embodiment, the first coupling feature 3044 is and/or forms a loop, eyelet, opening, and/or the like, and the second coupling feature 3042 is and/or forms a ball, protrusion, knob, knot, and/or the like. The tensile member 3035 can be and/or can include any suitable cable, tether, wire, catheter, conduit, etc. In some implementations, the tensile member 3035 can be used, for example, as a pusher or the like configured to push and/or otherwise advance the valve 3002 through a delivery system.

In this embodiment, the tensile member 3035 includes a first cable 3047 with an end portion that forms a threaded coupler configured to engage and/or couple to the coupler 3022 formed by the collar (e.g., a threaded nut or the like). The tensile member 3035 includes a second cable 3048 with an end portion that forms a receiving member configured to receive and/or removably couple to the second end of the lead 3041. For example, the receiving member of the second cable 3048 and the coupling feature 3042 formed by the second end of the lead 3041 can be a ball and cup coupling mechanism as described above with reference to the tensile members 2735 and 2835. Moreover, the tensile member 3035 can include and/or can form an outer sheath or catheter configured to at least partially house the first cable 3047 and the second cable 3048.

FIG. 31A shows the tensile member 3035 prior to coupling to the valve 3002 and/or the lead 3041. The lead 3041 is shown threaded through a portion of the valve 3002 and the waypoint 3021, looped around or through the attachment point 3036 of the proximal anchoring element 3034, and threaded back through the waypoint 3021 and portion of the valve 3002 such that the first end 3044 and the second end 3042 are each outside of the valve 3002 and/or above or proximal to the collar 3020.

FIG. 31B shows, the end portion of the first cable 3047 of the tensile member 3035 coupled to the coupler 3022 of the collar 3020, for example, via a threaded coupling. The first coupling feature 3044 of the lead 3041 is coupled to the first cable 3047 (e.g., the first coupling feature 3044 can be a loop that is disposed on or about the first cable 3047). In some implementations, the tensile member 3035 can be used as a proximal pusher by virtue of the first cable 3047 being coupled to the coupler 3022 formed by the collar 3020. For example, a substantially fixed portion of the first cable 3047 can extend from the tensile member 3035 (e.g., the outer sheath) such that a distal or pushing force applied to the tensile member 3035, via the first cable 3047, pushes the valve 3002. With the first coupling feature 3044 coupled to the first cable 3047, the first end of the lead 3041 is maintained in a relatively fixed position relative to the valve 3002. The second cable 3048 of the tensile member 3035 is shown coupled to the second coupling feature 3042 of the lead 3041 (e.g., via a ball and cup coupling mechanism and/or the like). Thus, while the tensile member 3035 and/or the first cable 3047 can be used to push the valve 3002, a tensile or pulling force can be applied to the second cable 3048, which can pull the second end of the lead 3041 in a proximal direction, thereby placing the lead in tension. Accordingly, the lead 3041 can maintain the proximal anchoring element 3034 in its first configuration during deployment.

FIG. 31C shows the first cable 3047 decoupled from the coupler 3022 of the collar 3020 and the first coupling feature 3044 at the first end of the lead 3041. The second coupling feature 3042 at the second end of the lead 3041 can remain coupled to the second cable 3048. After the valve has been deployed, the tensile member 3035 is pulled to remove the tensile member 3035 and the lead 3041 from the valve 3002 and the delivery system. With the tensile member 3035 removed, the proximal anchoring element 3034 is allowed to transition to its second configuration.

Figure 32:
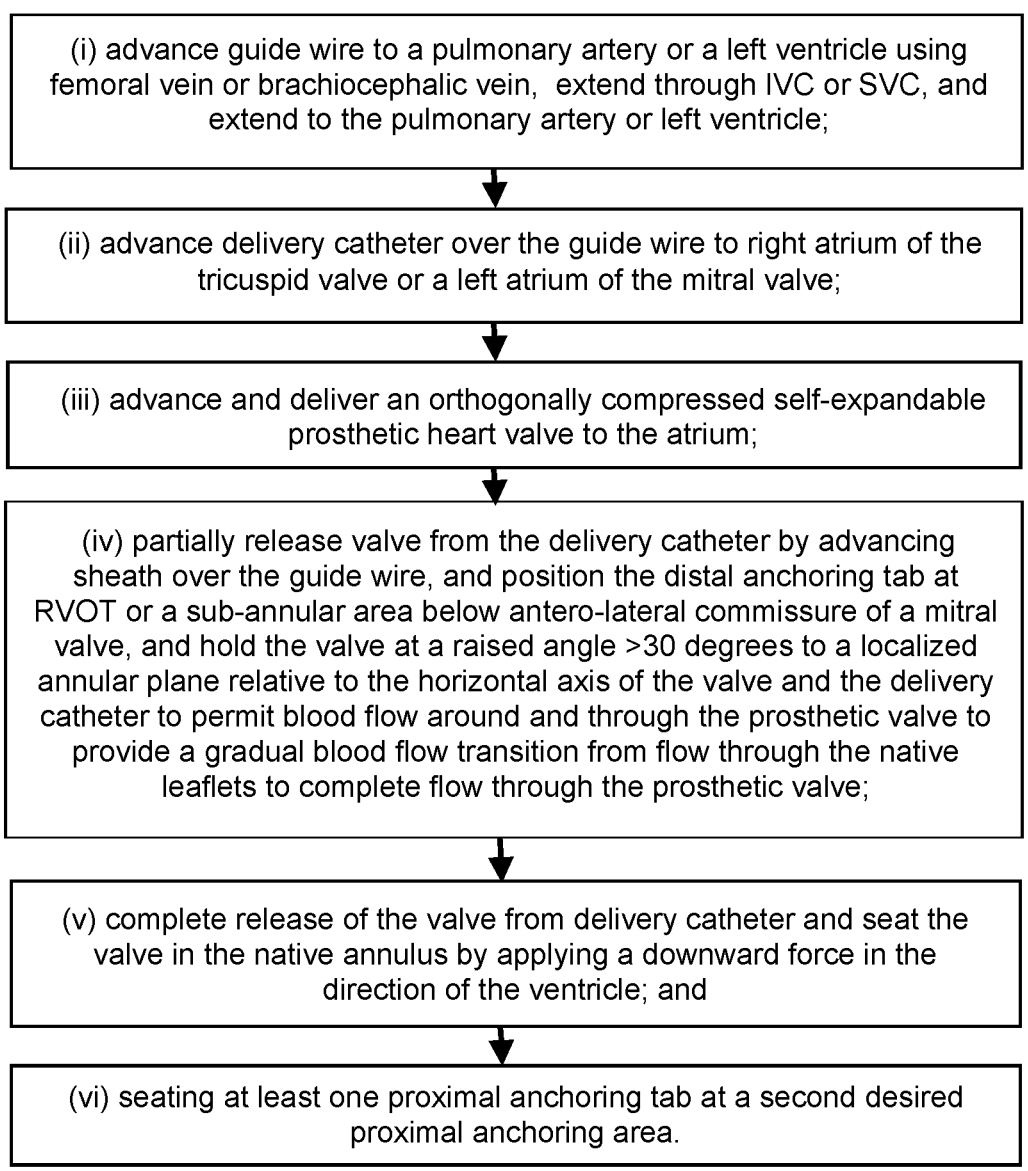
FIG. 32 is a flowchart illustrating a method of delivering a transcatheter prosthetic valve according to an embodiment.

FIG. 32 is a flowchart illustrating a method of delivering a transcatheter prosthetic valve according to an embodiment. In some instances, the method for delivery can include the steps of: (i) advance a guidewire through a femoral vein or brachiocephalic vein, an inferior vena cava (IVC) or superior vena cava (SVC), and into a pulmonary artery or left ventricle; (ii) advance a delivery catheter over the guide wire to a right atrium proximate to a native tricuspid valve or a left atrium proximate to a native mitral valve; (iii) advance and deliver an orthogonally compressed prosthetic heart valve to the right atrium or the left atrium, where the delivering includes partially releasing the valve from the delivery catheter, positioning a distal anchoring element of the valve in the pulmonary artery (e.g., a right ventricular outflow tract (RVOT)) or a subannular area below an anterolateral commissure of a mitral valve, and holding the valve at a raised angle of about 30 degrees or more relative to a localized horizontal annular plane of the native valve to permit blood flow around and through the prosthetic valve, allowing a gradual blood flow transition from a flow through native leaflets to a complete flow through the prosthetic valve; (iv) completely release of the valve from delivery catheter and seat the valve in the native annulus by applying a downward force in the direction of the ventricle (e.g., on a proximal side of the prosthetic valve); and (v) transition at least one proximal anchoring element to a second configuration in which the proximal anchoring element engages a subannular proximal anchoring area.

FIG. 33 is a flowchart illustrating a method 10 of delivering a transcatheter prosthetic valve according to an embodiment. The method 10 includes disposing adjacent to an annulus of a native valve of the heart, a distal portion of a delivery catheter having disposed in a lumen thereof the prosthetic valve in a compressed configuration, at 11. The prosthetic valve can be any of the valves disclosed herein. For example, the valve can be a valve having (i) a frame with at least a distal anchoring element and a proximal anchoring element, and (ii) a flow control component mounted within the frame configured to permit blood flow in a single direction through an inflow end of the valve and to block blood flow in an opposite direction through an outflow end of the valve. The valve can be delivered via a traditional delivery process or an orthogonal delivery process. For example, the valve can be delivered via any of the processes and/or methods described in detail herein and/or in the '957 PCT.

The valve is released from the lumen of the delivery catheter such that the valve transitions from the compressed configuration to an expanded configuration, at 12. As described in detail above with respect to specific embodiments, releasing the valve from the delivery catheter allows the prosthetic valve to expanded from the compressed configuration within the delivery catheter to the expanded configuration outside of the delivery catheter and suitable for deployment into the annulus of the native valve.

A portion of the distal anchoring element is placed on a ventricle side of the annulus of the native valve, at 13. In some implementations, the distal anchoring element can be a distal lower anchoring element that can be placed on the ventricle side of the annulus while the rest of the valve remains on the atrium side of the annulus. In some implementations, the distal anchoring element can be placed within a ventricular outflow tract. For example, the distal anchoring element can be placed within a right ventricular outflow tract (e.g., the pulmonary artery) when the native valve is a native tricuspid valve. In some instances, the distal anchoring element can engage subannular tissue to at least partially secure a distal end portion of the valve to the annular tissue while the remainder of the valve is maintained in a supra-annular position within the atrium side of the heart.

In some implementations, the method 10 optionally may include holding the prosthetic valve at an angle relative to the annulus of the native valve. The angle can be, for example, an oblique angle relative to the annulus. In some instances, holding the valve at an angle relative to the annulus can allow blood to flow from the atrium to the ventricle partially through the native valve annulus and around the prosthetic valve, as well as partially through the prosthetic valve, which can allow for assessment of the prosthetic valve function.

The prosthetic valve is seated in the annulus of the native valve while the proximal anchoring element is in a first configuration, at 14. The proximal anchoring element can have a first configuration and a second configuration. As described in detail above with reference to specific embodiments, the proximal anchoring element can be maintained in a compressed, restrained, tethered, and/or otherwise pre-released state when in the first configuration (e.g., via a tensile member or the like). When the proximal anchoring element is in the first configuration, a lower portion of the valve (e.g., a subannular portion) can have a size that allows the valve to extend through the annulus of the native valve.

After seating the prosthetic valve in the annulus, the proximal anchoring element is transitioned from its first configuration to its second configuration, at 15. As described in detail above with reference to specific embodiments, the proximal anchoring element can extend away from a body or transannular section of the valve. The proximal anchoring element can engage subannular tissue on a proximal side of the annulus that can at least partially secure the proximal side of the prosthetic valve to the proximal annular tissue. In some implementations, an atrial collar or the like of the valve and the distal and proximal anchoring elements can exert opposing forces on the annular tissue that can secure the prosthetic valve the annulus of the native valve. In some implementations, the valve can include one or more additional anchors or the like that can provide additional securement, as described in the '957 PCT.

Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations. The embodiments described herein can include various combinations and/or sub-combinations of the functions, components, and/or features of the different embodiments described.

What is claimed is:

1. A prosthetic heart valve, comprising:
    a valve frame having a central axis and defining an aperture extending along the central axis, the valve frame including a distal anchoring element and a proximal anchoring element; and
    a flow control component mounted within the aperture and configured to permit blood flow in a first direction approximately parallel to the central axis from an inflow end to an outflow end of the flow control component and block blood flow in a second direction, opposite the first direction,
    the valve frame having a compressed configuration to allow the prosthetic heart valve to be delivered to a heart of a patient via a delivery catheter, the valve frame configured to transition from the compressed configuration to an expanded configuration when the prosthetic heart valve is released from the delivery catheter, the valve frame in the expanded configuration having a first height along the central axis, a first lateral width along a lateral axis perpendicular to the central axis, and a longitudinal length along a longitudinal axis perpendicular to the central axis and the lateral axis, the valve frame in the compressed configuration having a second height along the central axis less than the first height and a second lateral width along the lateral axis less than the first lateral width, the flow control component configured to be seated in an annulus of a native valve of the heart when the valve frame is in the expanded configuration, the distal anchoring element and the proximal anchoring element configured to be inserted through the annulus of the native valve prior to the flow control component being seated therein, the proximal anchoring element configured to be transitioned from a first configuration to a second configuration after the flow control component is seated in the annulus of the native valve.

2. The prosthetic heart valve of claim 1, wherein the distal anchoring element is configured such that the distal anchoring element is positioned in a ventricular outflow tract before the flow control component is seated in the annulus of the native valve.

3. The prosthetic heart valve of claim 1, wherein each of the distal anchoring element and the proximal anchoring element is at least one of a wire loop, a wire frame, an integrated frame section, or a stent.

4. The prosthetic heart valve of claim 1, wherein the proximal anchoring element is configured such that the proximal anchoring element is in the first configuration as the flow control component is seated in the annulus of the native valve.

5. The prosthetic heart valve of claim 1, wherein the distal anchoring element is configured to be temporarily coupled to a guidewire.

6. The prosthetic heart valve of claim 1, wherein the valve frame is configured to at least temporarily couple to a tensile member, the tensile member having a first configuration in which the tensile member is engaged with the proximal anchoring element to maintain the proximal anchoring element in the first configuration and a second configuration in which the tensile member is disengaged from the proximal anchoring element to allow the proximal anchoring element to transition to the second configuration.

7. The prosthetic heart valve of claim 6, wherein a waypoint defined by the valve frame is configured to receive at least a portion of the tensile member.

8. The prosthetic heart valve of claim 6, wherein the proximal anchoring element is removably coupleable to the tensile member.

9. A prosthetic heart valve, comprising:
a valve frame having a transannular section and an atrial collar attached around a top edge of the transannular section;
a distal anchoring element coupled to the transannular section of the valve frame;
a proximal anchoring element coupled to the transannular section of the valve frame; and
a flow control component mounted within the valve frame and configured to permit blood flow in a first direction through an inflow end of the prosthetic heart valve and block blood flow in a second direction, opposite the first direction, through an outflow end of the prosthetic heart valve,
the prosthetic heart valve having a compressed configuration for introduction into a heart of a patient via a delivery catheter and an expanded configuration when the prosthetic heart valve is released from the delivery catheter within an atrium of the heart,
the transannular section of the valve frame configured to be seated in an annulus of a native valve of the heart when the prosthetic heart valve is in the expanded configuration, the distal anchoring element configured to be disposed in a ventricular outflow tract when the transannular section is seated in the annulus of the native valve, the proximal anchoring element configured to be transitioned from a first configuration to a second configuration after the transannular section is seated in the annulus of the native valve, a proximal end portion of the proximal anchoring element is disposed in a first position relative to the transannular section when in the first configuration and a second position relative to the transannular section when in the second configuration, the second position being farther from the transannular section than the first position.

10. The prosthetic heart valve of claim 9, wherein the native valve is a native tricuspid valve and the ventricular outflow tract is a right ventricular outflow track (RVOT).

11. The prosthetic heart valve of claim 9, wherein the proximal anchoring element is in the first configuration as the transannular section of the prosthetic heart valve frame is seated in the annulus of the native valve.

12. The prosthetic heart valve of claim 9, wherein the proximal anchoring element when in the second configuration is configured to contact sub-annular tissue on a proximal side of the annulus of the native valve.

13. The prosthetic heart valve of claim 9, wherein the valve frame is configured to at least temporarily couple to a tensile member, the tensile member having a first configuration in which the tensile member is engaged with the proximal anchoring element to maintain the proximal anchoring element in the first configuration, and a second configuration in which the tensile member is disengaged from the proximal anchoring element to allow the proximal anchoring element to transition to the second configuration.

14. The prosthetic heart valve of claim 13, wherein a waypoint defined by the valve frame is configured to receive at least a portion of the tensile member.

15. The prosthetic heart valve of claim 13, wherein the proximal anchoring element is removably coupleable to the tensile member.

16. A prosthetic heart valve, comprising:
a valve frame having a central axis and defining an aperture extending along the central axis, the valve frame including a distal anchoring element and a proximal anchoring element; and
a flow control component mounted within the aperture and configured to permit blood flow in a first direction approximately parallel to the central axis from an inflow end to an outflow end of the flow control component and block blood flow in a second direction, opposite the first direction,
the valve frame having a compressed configuration to allow the prosthetic heart valve to be delivered to a heart of a patient via a delivery catheter, the valve frame configured to transition from the compressed configuration to an expanded configuration when the prosthetic heart valve is released from the delivery catheter,
the flow control component configured to be seated in an annulus of a native valve of the heart when the valve frame is in the expanded configuration, the distal anchoring element configured to be inserted through the annulus of the native valve and positioned in a ventricular outflow tract prior to the flow control component being seated therein, the proximal anchoring element configured to be in a first configuration and inserted through the annulus of the native valve prior to the flow control component being seated therein, the proximal anchoring element configured to be transitioned from the first configuration to a second configuration after the flow control component is seated in the annulus of the native valve.

17. The prosthetic heart valve of claim 16, wherein the valve frame, when in the expanded configuration, has a first height along the central axis, a first lateral width along a lateral axis perpendicular to the central axis, and a longitudinal length along a longitudinal axis perpendicular to the central axis and the lateral axis, and when in the compressed configuration, the valve frame has a second height along the central axis less than the first height and a second lateral width along the lateral axis less than the first lateral width.

18. The prosthetic heart valve of claim 16, wherein each of the distal anchoring element and the proximal anchoring element is at least one of a wire loop, a wire frame, an integrated frame section, or a stent.

19. The prosthetic heart valve of claim 16, wherein the distal anchoring element is configured to be temporarily coupled to a guidewire.

20. The prosthetic heart valve of claim 16, wherein the valve frame is configured to at least temporarily couple to a tensile member, the tensile member having a first configuration in which the tensile member is engaged with the proximal anchoring element to maintain the proximal anchoring element in the first configuration and a second configuration in which the tensile member is disengaged from the proximal anchoring element to allow the proximal anchoring element to transition to the second configuration.

21. The prosthetic heart valve of claim 20, wherein a waypoint defined by the valve frame receives at least a portion of the tensile member.

22. The prosthetic heart valve of claim 20, wherein the proximal anchoring element is removably coupleable to the tensile member.

* * * * *